United States Patent
Takahashi et al.

(10) Patent No.: US 6,258,829 B1
(45) Date of Patent: Jul. 10, 2001

(54) CYCLOALKA[B]PYRIDINE-3-CARBONYLGUANIDINE DERIVATIVES, PROCESS FOR PRODUCING THE SAME, AND DRUGS CONTAINING THE SAME

(75) Inventors: Atsuo Takahashi; Kaoru Genkyou; Sachiko Yoneyama; Kazuyuki Aihara; Takashi Satoh; Fumiya Yoneyama; Jun Sasamori; Shin-ichi Yamada; Tetsuo Kimura; Kentaro Kogi, all of Fukushima (JP)

(73) Assignee: Toa Eiyo Ltd., Tokyo (JP)

( * ) Notice: Subject to any disclaimer, the term of this patent is extended or adjusted under 35 U.S.C. 154(b) by 0 days.

(21) Appl. No.: 09/367,873
(22) PCT Filed: Mar. 3, 1998
(86) PCT No.: PCT/JP98/00877
  § 371 Date: Sep. 3, 1999
  § 102(e) Date: Sep. 3, 1999
(87) PCT Pub. No.: WO98/39300
  PCT Pub. Date: Sep. 11, 1998

(30) Foreign Application Priority Data
  Mar. 6, 1997 (JP) .................................................. 9-067529

(51) Int. Cl.[7] ...................... A61K 31/435; C07D 221/04; C07D 471/04
(52) U.S. Cl. .......................... 514/335; 546/112; 546/113; 546/183
(58) Field of Search ............................. 514/335; 546/112, 546/113, 183

(56) References Cited

U.S. PATENT DOCUMENTS

| 5,373,024 | 12/1994 | Lang et al. |
| 5,824,691 | * 10/1998 | Kuno et al. ........................ 514/335.5 |

FOREIGN PATENT DOCUMENTS

| 0 556 674 | 8/1993 | (EP) . |
| 44-11893 | 5/1969 | (JP) . |
| 59-106993 | 6/1984 | (JP) . |
| 5-339228 | 12/1993 | (JP) . |
| 6-41049 | 2/1994 | (JP) . |
| 6-116230 | 4/1994 | (JP) . |
| 7-206823 | 8/1995 | (JP) . |
| 8-41028 | 2/1996 | (JP) . |
| 8-73427 | 3/1996 | (JP) . |
| 8-208602 | 8/1996 | (JP) . |
| 8-277269 | 10/1996 | (JP) . |
| 8-511243 | 11/1996 | (JP) . |
| 97/11055 | * 3/1997 | (WO) . |

OTHER PUBLICATIONS

Caplus 79:132812, Hawes Edward et al, RN #10345–93–2, 1973.*

* cited by examiner

Primary Examiner—Alan L. Rotman
Assistant Examiner—Rita Desai
(74) Attorney, Agent, or Firm—Arent Fox Plotkin & Kahn, PLLC

(57) ABSTRACT

This invention relates to a cycloalka[b]pyridine-3-carbonylguanidine derivative represented by the following general formula (1):

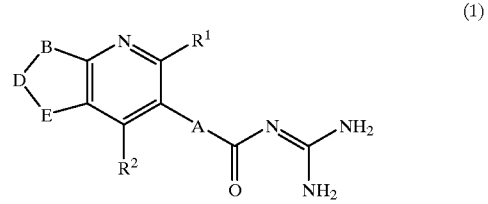

and a salt thereof, which can provide a drug having sodium/proton ($Na^+/H^+$) exchange transport inhibitory action.

7 Claims, No Drawings

CYCLOALKA[B]PYRIDINE-3-CARBONYLGUANIDINE DERIVATIVES, PROCESS FOR PRODUCING THE SAME, AND DRUGS CONTAINING THE SAME

TECHNICAL FIELD

This invention relates to a novel cycloalka[b]pyridine-3-carbonylguanidine derivative or a salt thereof, a process for producing the same, and a drug containing the same.

BACKGROUND ART

It has been reported that a pyrazine derivative having an acylguanidine, namely amiloride represented by the following formula, has a $Na^+/H^+$ exchange transport inhibitory action and shows anti-arrhythmic action [*Circulation*, 79, 1257 (1989)]. However, anti-arrhythmic action of amiloride is weak and it accompanies hypotensive action and salt excretion action, so that this compound is not desirable for the treatment of arrhythmia.

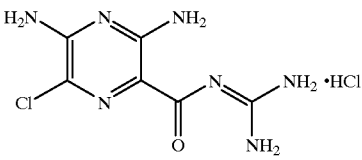

Recently, benzoylguanidine derivatives have been disclosed in *J. Mol. Cell. Cardiol.*, 24, Suppl. I, S. 92 (1992), JP-A-5-33922 (the term "JP-A" as used herein means an "unexamined published Japanese patent application") and JP-A-8-73427, and also an indoloylguanidine derivative in JP-A-8-208602, all as derivatives which have $Na^+/H^+$ exchange transport inhibitory action and show anti-arrhythmic action.

The object of the present invention is to find a novel cycloalka[b]pyridine-3-carbonylguanidine derivative which has $Na^+/H^+$ exchange transport inhibitory action and is useful as a therapeutic or preventive drug for diseases caused by the acceleration of $Na^+/H^+$ exchange transport system, such as hypertension, arrhythmia, angina pectoris, cardiac hypertrophy, diabetes, organ disorders due to ischemia or ischemia reperfusion, cerebral ischemic disorders, diseases due to excess proliferation of cells and diseases due to endothelial cell damage.

DISCLOSURE OF THE INVENTION

As a result of extensive investigation to achieve the just described object, the inventors of the present invention have found that a novel cycloalka[b]pyridine-3-carbonylguanidine derivative has excellent $Na^+/H^+$ exchange transport inhibitory action. Accordingly, the present invention relates to a cycloalka[b]pyridine-3-carbonylguanidine derivative represented by the following general formula (1):

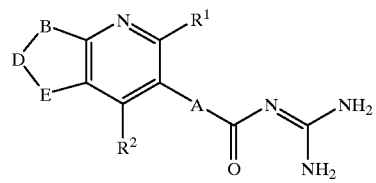

(1)

[wherein $R^1$ represents a hydrogen atom, a halogen atom, a lower alkyl group, a lower alkoxy group, an amino lower alkyl group, a lower alkoxyalkyl group, an aryl group, a heterocyclic group, an aralkyl group, a phenoxy lower alkyl group or an aralkyloxy lower alkyl group; $R^2$ represents a hydrogen atom, a halogen atom, a lower alkoxy group or a nitro group; A represents a single bond or a vinylene group; B represents a vinylene group or

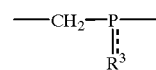

(wherein $R^3$ represents a hydrogen atom, a halogen atom, a hydroxy group, a lower alkyl group, a lower alkylidene group, a lower alkoxy group, a hydroxyower alkyl group, an aralkyl group, an aralkylidene group, a phenoxy lower alkyl group, a hydroxyimino group, a lower alkoxyimino group, an oxo group or a $(CH_2)_nONO_2$ group (n is 0 or an integer of 1), and P represents a methine group or a carbon atom); D represents a single bond, a methylene group or an ethylene group; and E represents a vinylene group,

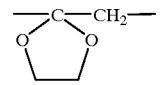

or

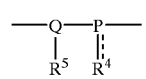

(wherein $R^4$ represents a hydrogen atom, a halogen atom, a hydroxy group which may be protected or an oxo group, $R^5$ represents unsubstitution, a hydrogen atom or a lower alkyl group, P represents a methine group or a carbon atom, and Q represents a methine group or an oxygen atom), provided that when A and D are a single bond, B and E are not a vinylene group at the same time]or a salt thereof, a process for the production thereof, and its use as a $Na^+/H^+$ exchange transport inhibitor.

Examples of the halogen atom of the substituent group $R^1$, $R^2$, $R^3$ or $R^4$ of the cycloalka[b]pyridine-3-carbonylguanidine derivative represented by the general formula (1) include fluorine atom, chlorine atom, bromine atom and iodine atom. Examples of the lower alkyl group of $R^1$, $R^3$ or $R^5$ include straight, branched or halogen atom-substituted lower alkyl groups having 1 to 4 carbon atoms, such as methyl, ethyl, propyl, isopropyl, n-butyl, sec-butyl and tert-butyl groups. Examples of the lower alkylidene group of $R^3$ include lower alkylidene groups having 1 to 4 carbon atoms, methylene, ethylidene and propylidene groups. Examples of the lower alkoxy group of $R^1$, $R^2$ or $R^3$ include straight or branched lower alkoxy group having 1 to 4 carbon atoms, such as methoxy, ethoxy, propoxy, isopropoxy, n-butoxy and sec-butoxy groups. The hydroxy group of $R^4$ may be protected with a protecting group such as trimethylsilyl group or tert-butyldimethylsilyl group. Examples of the amino lower alkyl group of $R^1$ include aminomethyl, methylaminomethyl, dimethylaminomethyl, ethylaminomethyl, diethylaminomethyl and benzylaminomethyl. Examples of the lower alkoxyalkyl group of $R^1$ include methoxymethyl, methoxyethyl, methoxypropyl and methoxybutyl. Examples of the hydroxyower alkyl group of $R^3$ include hydroxymethyl, 1-hydroxyethyl and 1-hydroxypropyl. Examples of the aryl group of $R^1$ include phenyl, biphenyl and naphthyl. Examples of the heterocyclic group of $R^1$ include pyridyl, pyrimidinyl and thienyl. Examples of the aralkyl group of $R^1$ or $R^3$ include those in which the cyclic moiety is not only an aromatic ring but also a heterocyclic ring, such as benzyl, 1-methylpyrrolinylmethyl and pyridinylmethyl. Examples of the aralkylidene group of $R^3$ include those in which the cyclic moiety is not only an aromatic ring but also a heterocyclic ring, such as benzylidene, pyridylmethylene and thienylmethylene. Examples of the phenoxy lower alkyl group of $R^1$ or $R^3$ include phenoxymethyl which may be substituted, and examples of the substituent group include N-[2-(dimethylamino)ethyl]aminocarbonyl and N-[2-(diethylamino)ethyl]aminocarbonyl. Examples of the aralkyloxy lower alkyl group of $R^1$ include 3-pyridylmethyloxymethyl and 1-imidazolylmethyloxymethyl. Examples of the lower alkoxyimino group of $R^3$ include methoxyimino, ethoxyimino and propoxyimino.

Stereoisomers such as geometrical isomers and enantiomers based on asymmetric carbon atoms are also included in the cycloalka[b]pyridine-3-carbonylguanidine derivative represented by the general formula (1).

In general, cycloalka[b]pyridine-3-carbonylguanidine derivative (1) is weak basic and therefore is bonded to an acid to form a salt. All of pharmacologically acceptable acid addition salts can be used, and their examples include acid addition salts with mineral acids such as hydrochloric acid, sulfuric acid, nitric acid and phosphoric acid, acid addition salts with organic sulfonic acids such as methanesulfonic acid, benzenesulfonic acid and toluenesulfonic acid and acid addition salts with organic carboxylic acids such as acetic acid, tartaric acid, maleic acid, fumaric acid, oxalic acid, lactic acid and citric acid.

EMBODIMENT OF THE INVENTION

The compound of the present invention represented by the aforementioned general formula (1) can be produced by a production method described by the following reaction formula.

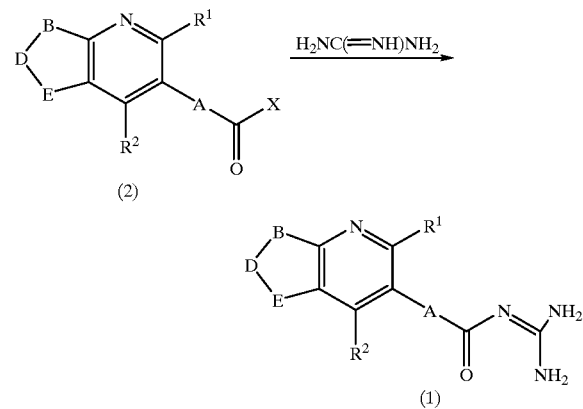

(In the above formula, X is a hydroxy group or a leaving group which can be substituted easily by nucleophilic reaction, and $R^1$, $R^2$, A, B, D and E are as defined in the foregoing.)

Examples of the leaving group which can be substituted easily by nucleophilic reaction include a halogen atom, an alkoxy group, a p-nitrophenoxy group and a pentafluorophenoxy group.

When X is a hydroxy group, the compound (1) can be produced by allowing a cycloalka[b]pyridine-3-carboxylic acid represented by the general formula (2) to react with guanidine in an inert solvent in the presence of a condensing agent.

Examples of the condensing agent to be used in the reaction include dicyclohexylcarbodiimide (DCC), diisopropylcarbodiimide (DIPC), 1-ethyl-3-(3-dimethylaminopropyl)carbodiimide (EDC), benzotriazol-1-yltris(dimethylamino)phosphonium hexafluorophosphide salt (BOP), diphenylphosphonyl azide (DPPA) and N,N-carbonyldiimidazole (CDI).

Guanidine is used in an amount of from 1 to 50 equivalents, preferably from 3 to 20 equivalents, based on the compound (2).

Examples of the solvent to be used in the reaction include benzene, toluene, xylene, tetrahydrofuran, 1,2-dimethoxyethane, 1,4-dioxane, dichloromethane, chloroform, 1,2-dichloroethane, ethyl acetate, dimethylformamide, dimethylacetamide and pyridine, or mixed solvents thereof. The reaction temperature is from –30° C. to about boiling point of the solvent used, preferably from –10° C. to 150° C. The reaction time is generally from 30 minutes to 72 hours, preferably from 30 minutes to 48 hours. In this case, it is desirable to carry out the reaction in an atmosphere of inert gas such as argon gas or nitrogen gas in the presence, if necessary, of an additive agent such as N-hydroxysuccinimide, 1-hydroxybenzotriazole or 3-hydroxy-4-oxo-3,4-dihydro-1,2,3-benzotriazine.

When X is a leaving group which can be substituted easily by nucleophilic reaction, the compound (1) can be produced by allowing a reactive derivative of the cycloalka[b]pyridine-3-carboxylic acid represented by the general formula (2) to react with guanidine in an inert solvent.

Examples of the reactive derivative of carboxylic acid include an acid halide and an ester derivative. Illustratively, the acid halide include acid chloride and acid bromide, and the ester derivative include active esters such as p-nitrophenyl ester, N-hydroxysuccinimide ester and pentafluorophenyl ester and general esters such as methyl ester and ethyl ester. Such reactive derivatives of carboxylic acid can be obtained easily from corresponding carboxylic acid in accordance with a generally used synthetic method.

When the compound (1) is produced by allowing an acid halide to react with guanidine, guanidine is used in an amount of from 1 to 50 equivalents, preferably from 1 to 30 equivalents, based on the compound (2). Examples of the solvent to be used in the reaction include methanol, ethanol, propanol, secondary propanol, butanol, tertiary butanol, benzene, toluene, xylene, tetrahydrofuran, 1,2-dimethoxyethane, 1,4-dioxane, dichloromethane, chloroform, 1,2-dichloroethane, ethyl acetate, dimethylformamide, dimethylacetamide and dimethyl sulfoxide, or mixed solvents thereof. The reaction temperature is from –30° C. to about boiling point of the solvent used, preferably from –20° C. to 150° C. The reaction time is generally from 30 minutes to 72 hours, preferably from 30 minutes to 48 hours. In this case, it is desirable to carry out the reaction in an atmosphere of inert gas such as argon gas or nitrogen gas.

When the compound (1) is produced by allowing an ester derivative to react with guanidine, guanidine is used in an amount of from 1 to 50 equivalents, preferably from 5 to 20 equivalents, based on the compound (2). Examples of the solvent to be used in the reaction include methanol, ethanol, propanol, secondary propanol, butanol, tertiary butanol, benzene, toluene, xylene, tetrahydrofuran, 1,2-dimethoxyethane, 1,4-dioxane, dichloromethane, chloroform, 1,2-dichloroethane, ethyl acetate, dimethylformamide, dimethylacetamide and dimethyl sulfoxide, or mixed solvents thereof. The reaction temperature is from 0° C. to about boiling point of the solvent used, preferably from 0° C. to 150° C. The reaction time is generally from 30 minutes to 96 hours, preferably from 30 minutes to 72 hours. In this case, it is desirable to carry out the reaction in an atmosphere of inert gas such as argon gas or nitrogen gas.

The compound of the present invention represented by the aforementioned general formula (1) can be produced by a production method described by the following reaction formulae.

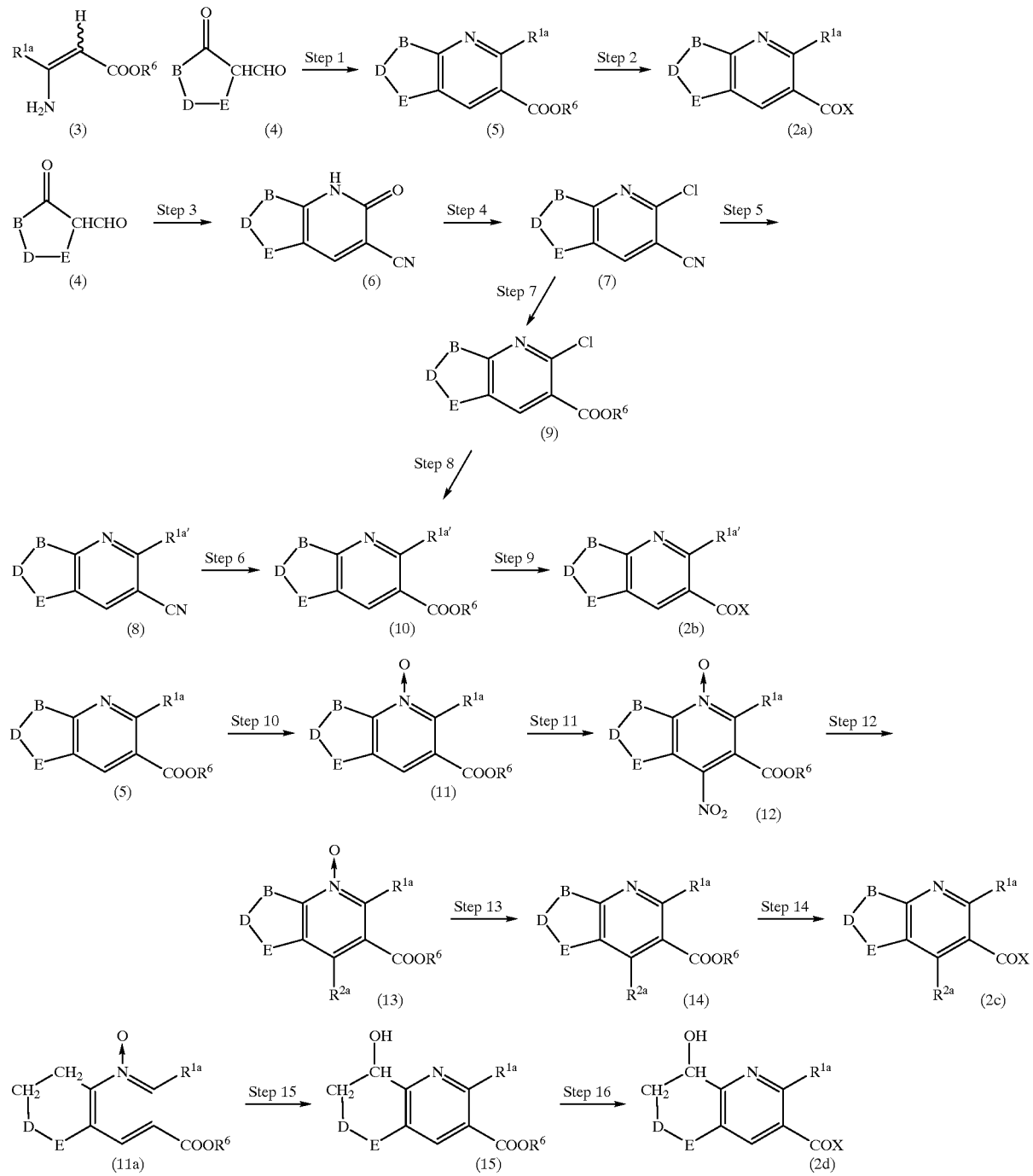

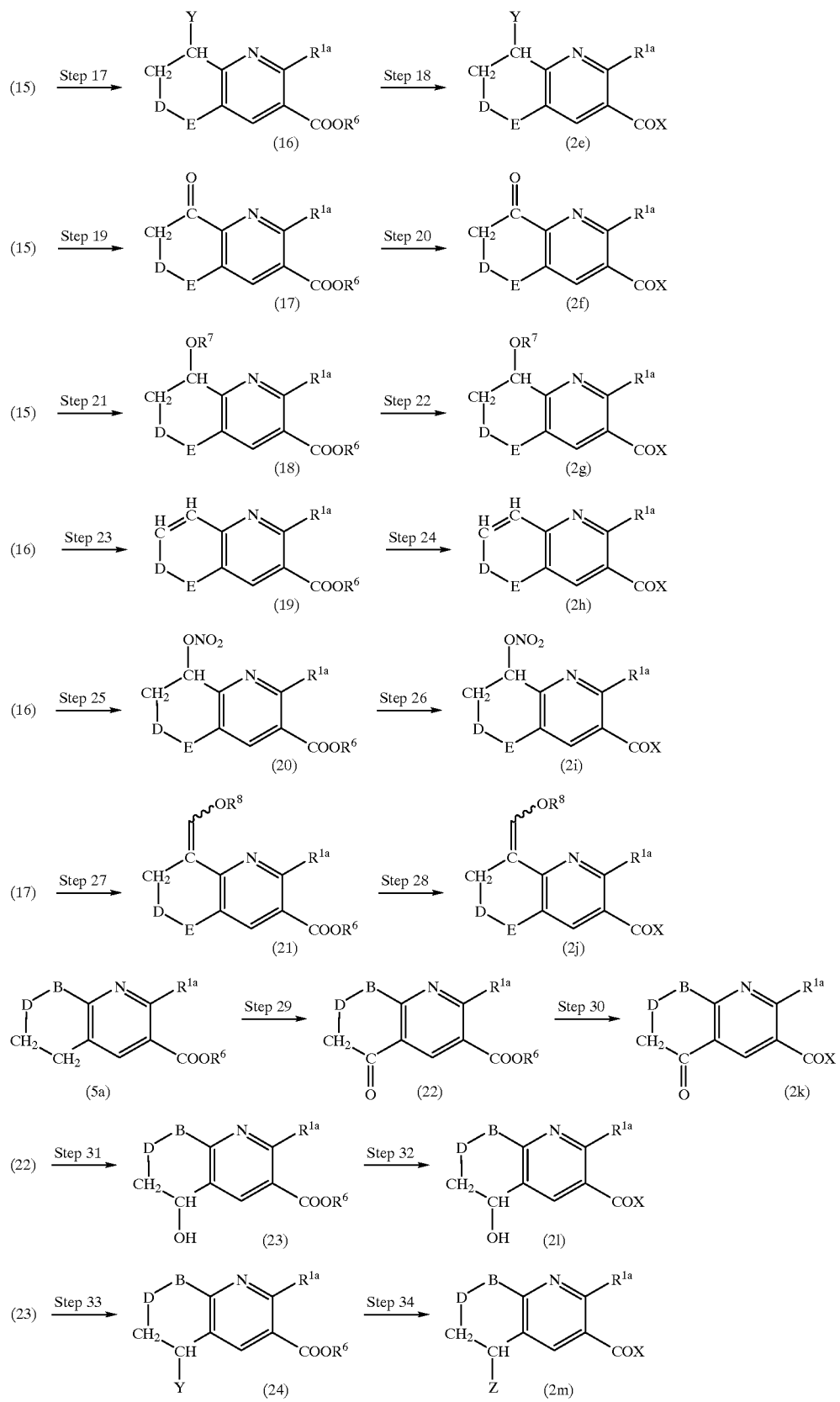

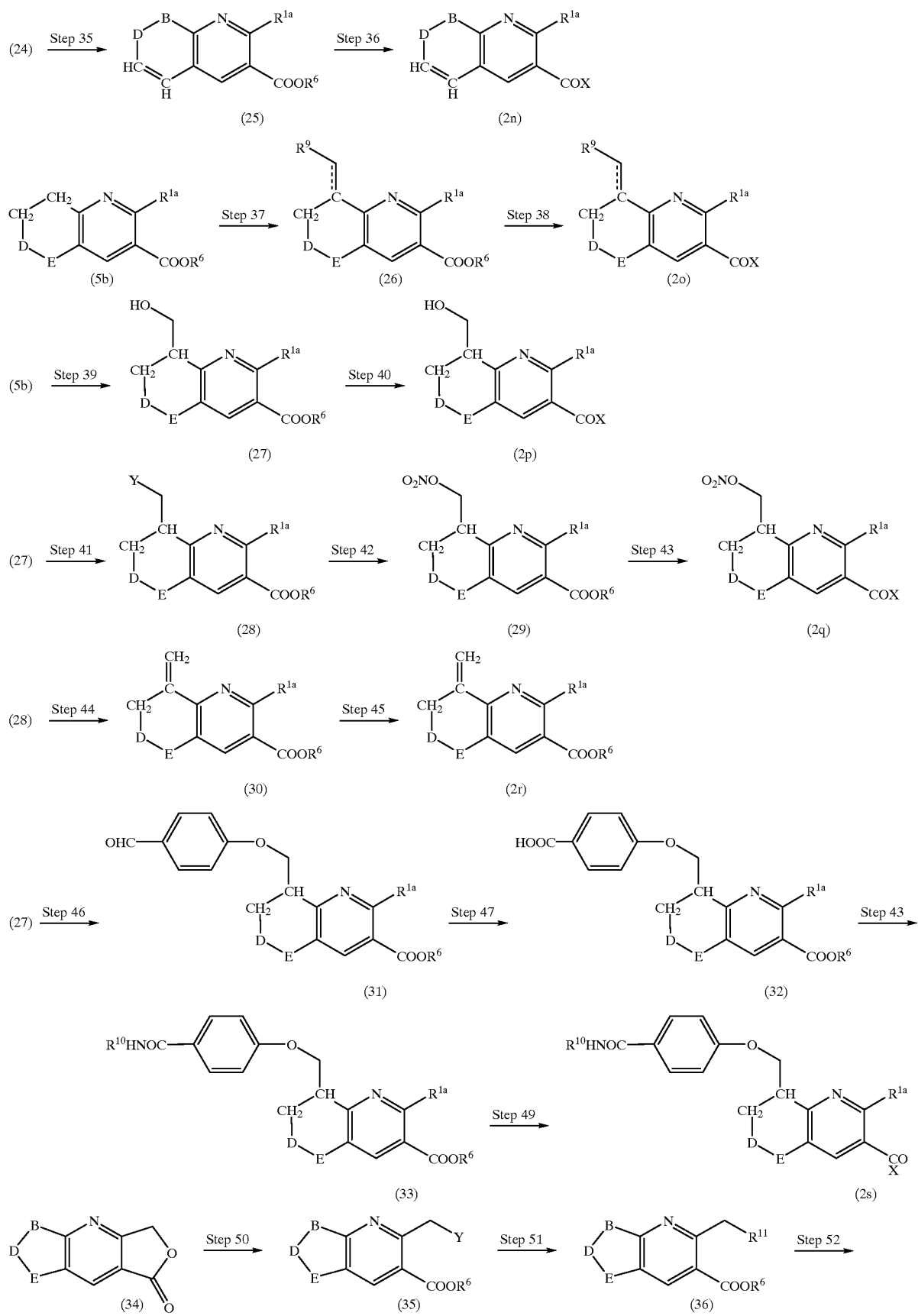

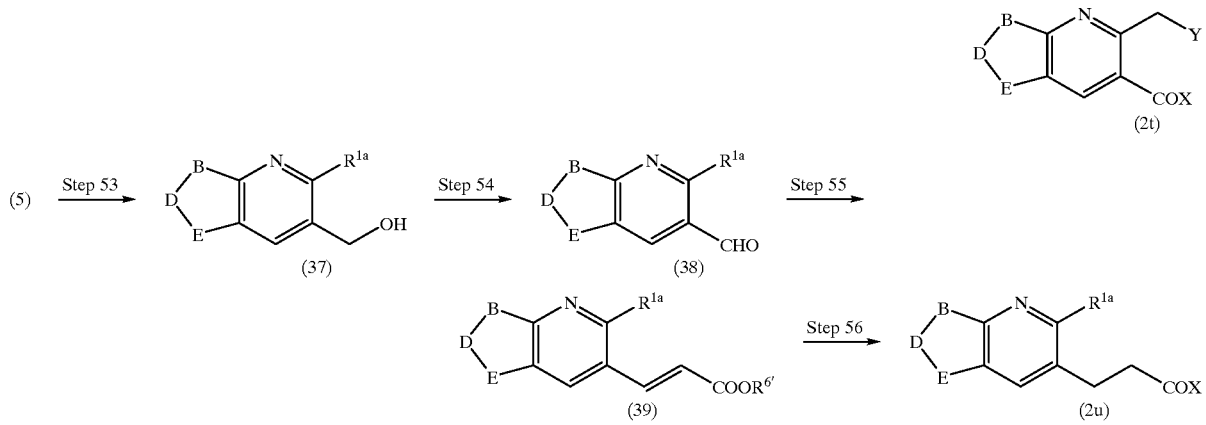

(In the above formulae, each of $R^6$ and $R^7$ is a lower alkyl group, $R^8$ is a hydrogen atom or a lower alkyl group, $R^9$ is an aryl group or a heterocyclic group, $R^{10}$ is an amino lower alkyl group, $R^{11}$ is an amino group, an aralkyloxy group or a substituted phenoxy group, $R^{1a}$ is a lower alkyl group, a lower alkoxyalkyl group, an aryl group, a heterocyclic group or an aralkyl group, $R^{1a'}$ is a hydrogen atom, a halogen atom or a lower alkoxy group, $R^{2a}$ is a halogen atom, a lower alkoxy group or a nitro group, and Y is a halogen atom.)

The compound (2a) can be produced from compounds (3) and (4) in the following manner. That is, a reactive derivative of carboxylic acid (2a) can be produced by synthesizing a compound (5) under the conditions described in the literature [Step 1: Roczniki. Chem., 44, 431 (1970)] from a compound (3) synthesized in accordance with the method described in the literature [J. Org. Chem., 48, 3883 (1983)] and a compound (4) synthesized in accordance with the method described in the literature [Org. Syn., Coll. Vol. 4, 536 (1963)] and then carrying out a generally used synthetic method [Step 2].

Regarding the compound (2b), a reactive derivative of carboxylic acid (2b) can be produced from the compound (4) in accordance with the methods described in the literature [Step 3: J. Am. Chem. Soc., 79, 1402 (1957), Steps 4, 5, 6, 7 and 8: J. Am. Chem. Soc., 82, 557 (1960)] and then carrying out a generally used synthetic method.

Regarding the compound (2c), a reactive derivative of carboxylic acid (2c) can be produced by subjecting an N-oxide compound (11) synthesized by oxidation reaction of the compound (5) to nitration with fuming nitric acid or nitric acid and then, as occasion demands, to a substitution reaction, thereby synthesizing a compound (13) which is subsequently reduced with Raney nickel or phosphorus tribromide to synthesize a compound (14), and then carrying out a generally used synthetic method.

Regarding the compound (2d), a reactive derivative of carboxylic acid (2d) can be produced by carrying out rearrangement reaction of a compound (11a) under heating in acetic anhydride, subjecting the thus obtained compound to alkali hydrolysis to synthesize a compound (15) and then carrying out a generally used synthetic method.

Regarding the compound (2e), a reactive derivative of carboxylic acid (2e) can be produced by subjecting the compound (15) to halogenation with a halogenating agent such as thionyl chloride or triphenylphosphine-carbon tetrabromide to synthesize a compound (16) and then carrying out a generally used synthetic method.

Regarding the compound (2f), a reactive derivative of carboxylic acid (2f) can be produced by oxidizing the compound (15) with activated manganese dioxide, pyridinium dichromate or pyridinium chlorochromate to synthesize a compound (17) and then carrying out a generally used synthetic method.

Regarding the compound (2g), a reactive derivative of carboxylic acid (2g) can be produced by subjecting the compound (15) to alkylation with an alkyl halide in the presence of a base such as sodium hydride or potassium carbonate to synthesize a compound (18) and then carrying out a generally used synthetic method.

Regarding the compound (2h), a reactive derivative of carboxylic acid (2h) can be produced by subjecting the compound (16) to dehydrohalogenation reaction using an agent such as 1,8-diazabicyclo[4.3.0]-7-undecene to synthesize a compound (19) and then carrying out a generally used synthetic method.

Regarding the compound (2i), a reactive derivative of carboxylic acid (2i) can be produced by allowing the compound (16) to react with silver nitrate to synthesize a nitric ester compound (20) and then carrying out a generally used synthetic method.

Regarding the compound (2j), a reactive derivative of carboxylic acid (2j) can be produced by allowing the compound (17) to react with hydroxyamine, further carrying out its alkylation as occasion demands, to synthesize a compound (21) and then carrying out a generally used synthetic method.

Regarding the compound (2k), a reactive derivative of carboxylic acid (2k) can be produced by synthesizing a compound (22) from a compound (5a) in accordance with the method described in the literature [Step 29: Yakugaku Zasshi (Pharmacy Journal), 95, 1439 (1975)] and then carrying out a generally used synthetic method.

Regarding the compound (2l), a reactive derivative of carboxylic acid (2l) can be produced by reducing the compound (22) using a reducing agent such as sodium borohydride to synthesize a compound (23) and then carrying out a generally used synthetic method.

The compound (2m) can be produced from the compound (23) by almost the same method for the production of the compound (2e).

The compound (2n) can be produced from a compound (24) by almost the same method for the production of the compound (2h).

Regarding the compound (2o), a reactive derivative of carboxylic acid (2o) can be produced by synthesizing a compound (26) from a compound (5b) through its condensation reaction in accordance with the method described in the literature [Step 37: *J. Med. Chem.*, 38, 1473 (1995)] and subsequent catalytic reduction to reduce the double bond as occasion demands, and then carrying out a generally used synthetic method.

Regarding the compound (2p), a reactive derivative of carboxylic acid (2p) can be produced by synthesizing a compound (27) from the compound (5b) in accordance with the method described in the literature [Step 39: *Roczniki. Chem.*, 37, 395 (1963)] and then carrying out a generally used synthetic method.

Regarding the compound (2q), a reactive derivative of carboxylic acid (2q) can be produced by synthesizing a compound (28) from the compound (27) through its halogenation using a halogenating agent such as thionyl chloride or triphenylphosphine-carbon tetrabromide and then carrying out almost the same method for the production of the compound (2i).

Regarding the compound (2r), a reactive derivative of carboxylic acid (2r) can be produced by synthesizing a compound (30) from the compound (28) through its dehydrohalogenation reaction using a proper agent such as 1,8-diazabicyclo[4.3.0]-7-undecene and then carrying out a generally used synthetic method.

Regarding the compound (2s), a reactive derivative of carboxylic acid (2s) can be produced by condensing the compound (27) with p-hydroxybenzaldehyde through Mitsunobu reaction to obtain a compound (31), oxidizing the thus obtained compound (31) to synthesize a compound (32), carrying out amidation of the thus obtained compound (32) through its reaction with an amine using a condensing agent such as DCC or EDC, thereby obtaining a compound (33), and then carrying out a generally used synthetic method.

Regarding the compound (2t), a reactive derivative of carboxylic acid (2t) can be produced by allowing a compound (34) to react with an alcohol under an acidic condition, carrying out halogenation of the resulting compound using a halogenating agent such as thionyl chloride or triphenylphosphine-carbon tetrabromide to obtain a compound (35), synthesizing a compound (36) therefrom through its substitution reaction and then carrying out a generally used synthetic method.

Regarding the compound (2u), a reactive derivative of carboxylic acid (2u) can be produced by synthesizing a compound (37) from the compound (5) through its reduction with a reducing agent such as lithium aluminum hydride or diisobutyl aluminum hydride, oxidizing the thus obtained compound (37) with an oxidizing agent such as sodium chlorite to obtain a compound (38), synthesizing a compound (39) therefrom by Wittig reaction and then carrying out a generally used synthetic method.

ACTIONS AND EFFECTS OF THE INVENTION

The $Na^+/H^+$ exchange transport inhibitory action of typical examples of the compound (1) of the present invention shown below is described in the following in detail.

[Test compounds]
8-Hydroxy-2-methyl-5,6,7,8-tetrahydrocyclohexa[b]pyridine-3-carbonylguanidine (compound A)
2,6-Dimethyl-5,6,7,8-tetrahydrocyclohexa[b]pyridine-3-carbonylguanidine (compound B)
2-Ethyl-6,7,8,9-tetrahydro-5H-cyclohepta[b]pyridine-3-carbonylguanidine (compound C)
5-Hydroxy-2-methyl-6,7,8,9-tetrahydro-5H-cyclohepta[b]pyridine-3-carbonylguanidine (compound D)
2,9-Dimethyl-6,7,8,9-tetrahydro-5H-cyclohepta[b]pyridine-3-carbonylguanidine (compound E)
9-Methoxy-2-methyl-6,7,8,9-tetrahydro-5H-cyclohepta[b]pyridine-3-carbonylguanidine (compound F)
2-Trifluoromethyl-6,7,8,9-tetrahydro-5H-cyclohepta[b]pyridine-3-carbonylguanidine (compound G)
2-Chloro-6,7,8,9-tetrahydro-5H-cyclohepta[b]pyridine-3-carbonylguanidine (compound H)
2-Methoxy-6,7,8,9-tetrahydro-5H-cyclohepta[b]pyridine-3-carbonylguanidine (compound I)
2-(3-Pyridyl)-6,7,8,9-tetrahydro-5H-cyclohepta[b]pyridine-3-carbonylguanidine (compound J)
2-Methyl-6,7-dihydro-5H-cyclohepta[b]pyridine-3-carbonylguanidine (compound K)
Amiloride (control drug)

[Inhibition studies on $Na^+/H^+$ exchange transport]

The $Na^+/H^+$ exchange transport inhibitory activity was measured in accordance with the method of Scholz et al. [*Br. J. Pharmacol.*, 109, 562 (1993)], using the swelling of rat platelets induced by sodium propionate as an index.

Under ether anesthesia, blood sample (8 ml) was collected from the abdominal aorta of Wistar rat and mixed with 1 ml of acid citrate dextrose as an anticoagulant. The resulting mixture was immediately centrifuged at 90×g for 10 minutes, and the thus collected supernatant was used as platelet rich plasma. Next, the thus prepared platelet rich plasma ($10 \times 10^6$ platelets/50 $\mu$l) was added to 250 $\mu$l of 140 mM sodium propionate buffer (pH 6.7, 1% dimethyl sulfoxide in final concentration) containing each test compound dissolved in dimethyl sulfoxide, and the decrease in absorbance caused by the swelling of platelets was periodically measured using Hema-Tracer (manufactured by Nk).

The decreased absorbance ratio 20 seconds after the addition of platelet rich plasma was measured as the $Na^+/H^+$ exchange activity, and the inhibitory activity of each test compound was expressed as relative activity when the action of 300 $\mu$M amiloride was defined as 100% inhibition.

In this case, each test result was evaluated from 50% inhibition concentration ($IC_{50}$ value) by using probit methods. $IC_{50}$ of these test compounds on $Na^+/H^+$ exchange transport are summarized in Table 1. In the table, + means an $IC_{50}$ value of $1.0 \times 10^{-6}$ M or more, ++ means an $IC_{50}$ value of from $9.9 \times 10^{-7}$ M to $1.0 \times 10^{-7}$ M and +++ means an $IC_{50}$ value of $9.9 \times 10^{-8}$ M or less.

TABLE 1

Inhibitory actions of test compounds on $Na^+/H^+$ exchange transport

| Compound | IC50 value |
|---|---|
| A | ++ |
| B | +++ |
| C | +++ |
| D | ++ |
| E | +++ |
| F | +++ |
| G | ++ |
| H | +++ |
| I | + |
| J | + |
| K | +++ |

[Toxicity test]

When maleic acid salt of the compound (K) was dissolved in physiological saline containing 50% propylene glycol and administered intravenously in a single dose of 100 mg/kg to male SD rats of 6 weeks of age, no death cases were found and no toxic changes attributable to the compound (K) were observed on the animals for 5 days after the administration. Also, when the same compound was dissolved in physiological saline and administered intravenously in a daily dose of 10 mg/kg to male SD rats at 8 weeks of age, no death cases were found and no toxic changes attributable to the compound (K) were observed on the animals for 12 days.

Since the novel cycloalka[b]pyridine-3-carbonylguanidine derivatives represented by the general formula (1) and salts thereof have strong $Na^+/H^+$ exchange transport inhibitory action, they are useful as therapeutic or preventive drugs for diseases caused by the accelerated $Na^+/H^+$ exchange transport system, such as hypertension, arrhythmia, angina pectoris, cardiac hypertrophy, diabetes, organ disorders due to ischemia or ischemia reperfusion [e.g., disorders caused by myocardial ischemia reperfusion, acute renal failure, organ transplantation and percutaneous transluminal coronary angioplasty (PTCA)], cerebral ischemic disorders [e.g., disorders accompanied by cerebral infarction, disorders occurred as secondary diseases after cerebral apoplexy and brain edema], diseases caused by excess proliferation of cells (e.g., proliferation of fibroblasts, smooth muscle cells and mesangial cells) [e.g., atherosclerosis, pulmonary fibrosis, hepatic fibrosis, renal fibrosis, renal glomerulosclerosis, organ hypertrophy, prostatic hypertrophy, diabetic complication and restenosis after PTCA] or diseases due to endothelial cell damages.

When the compound of the present invention or a salt thereof is used as a medicament, it can be administered orally or parenterally. That is, it can be administered by the usually used administration methods including oral administration in suitable dosage forms such as tablets, granules and capsules. Alternatively, it can be administered parenterally in the form of injections as solutions, emulsions or suspensions. It can also be used by rectal administration in the form of suppositories. When the compound is made into oral preparations, they are produced in the usual way by optionally blending with various additives such as fillers (e.g., lactose), disintegrators (e.g., starches), binders (e.g., hydroxypropylmethylcellulose) and lubricants (e.g., metal stearate). When made into injections, they are produced in the usual way by optionally blending with various additives such as a buffer (e.g., phosphate) and a tonicity agent (e.g., sodium chloride). When used as suppositories, they can be produced by dissolving or dispersing the compound in an oleaginous base (e.g., cacao butter), an emulsifying base (e.g., hard fat) or a water-soluble base (e.g., macrogol) and then solidifying the mixture by spontaneous cooling in a mold to form it into appropriate shape.

Dosage and the number of times of administration vary depending on the disease to be treated, symptoms, age and weight of each patient and administration method, but the compound may be administered in an amount of generally from 0.1 mg to 3,000 mg, preferably from 1 mg to 1,000 mg, per day per adult, once a day or by dividing the daily dose into several doses per day.

BEST MODE OF CARRYING OUT THE INVENTION

Examples of the compound of the present invention are given below by way of illustration and not by way of limitation.

REFERENCE EXAMPLE 1

Ethyl 3-amino-3-(3-pyridyl)acrylate

In an atmosphere of argon, activated zinc powder (4.88 g, 0.07 g atom) was suspended in anhydrous tetrahydrofuran (THF) (25.0 ml) to which was subsequently added dropwise several drops of ethyl bromoacetate while heating under reflux. When color of the reaction solution became green, 3-cyanopyridine (1.59 g, 15.0 mmol) was added to the solution, ethyl bromoacetate (6.0 ml, 51.4 mmol) was added dropwise thereto spending 50 minutes and then the mixture was heated under reflux for 15 minutes. After cooling, the reaction solution was diluted with THF, mixed with 50% potassium carbonate aqueous solution (15.0 ml) and then stirred for 30 minutes. After standing, the organic layer was collected and extracted three times with THF in the same manner and then the thus obtained organic layer was dried over anhydrous magnesium sulfate. The solvent was evaporated under reduced pressure, and the resulting residue was purified by a silica gel column chromatography (ethyl acetate:hexane=2:1–4:1) to obtain the title compound (2.26 g, 72.3%) as pale yellow oil.

IR (neat) $\nu_{max}$: 3432, 3324, 2980, 1736, 1668, 1624, 1594, 1560, 1476, 1364, 1312, 1246, 1176, 1096, 1044, 1024, 788, 710, 632 $cm^{-1}$. $^1$H-NMR (CDCl$_3$) δ: 1.30 (3 H, t, J=7.0 Hz), 4.19 (2 H, q, J=7.0 Hz), 4.96 (1 H, s), 6.38–6.52 (2 H, br-s), 7.33 (1 H, dd, J=6.2, 4.8 Hz), 7.83 (1 H, dd, J=6.2, 1.8 Hz), 8.67 (1 H, dd, J=4.8, 1.3 Hz), 8.80 (1 H, d, J=1.8 Hz).

REFERENCE EXAMPLE 2

Ethyl 3-amino-3-(1-methylpyrrolylmethyl-2-yl)acrylate

In the same manner as described in Reference Example 1, the title compound (2.62 g, 84.0%) was obtained as pale yellow oil from 1-methyl-2-pyrrole-acetonitrile (1.83 ml, 15.0 mmol) and ethyl bromoacetate (7.0 ml, 60.0 mmol).

IR (neat) $\nu_{max}$: 3464, 3336, 2980, 1742, 1718, 1666, 1620, 1562, 1494, 1446, 1420, 1364, 1316, 1294, 1270, 1160, 1092, 1040, 786, 714 $cm^{-1}$. $^1$H-NMR (CDCl$_3$) δ: 1.26 (3 H, t, J=7.3 Hz), 2.27 (1 H, s), 3.43 (1 H, s), 3.50 (3 H, s), 4.11 (2 H, q, J=7.3 Hz), 4.61 (1 H, s), 6.04–6.06 (2 H, m), 6.57–6.60 (1 H, m).

REFERENCE EXAMPLE 3

Ethyl 3-amino-3-(2-thienyl)acrylate

In the same manner as described in Reference Example 1, the title compound (3.23 g, quantitative) was obtained as pale yellow oil from thiophene-2-carbonitrile (1.41 ml, 15.0 mmol) and ethyl bromoacetate (7.0 ml, 60.0 mmol).

IR (neat) $\nu_{max}$: 3456, 3332, 2980, 1738, 1716, 1664, 1612, 1562, 1514, 1422, 1366, 1232, 1228, 1174, 1094, 1074, 1048, 1024, 854, 788, 710 at $cm^{-1}$. $^1$H-NMR (CDCl$_3$) δ: 1.29 (3 H, t, J=7.0 Hz), 4.17 (2 H, q, J=7.0 Hz), 5.11 (1 H, s), 6.38–6.49 (2 H, br-s), 7.06 (1 H, dd, J=4.4, 4.2 Hz), 7.33–7.38 (2 H, m).

REFERENCE EXAMPLE 4

Ethyl 2-methyl-6,7,8,9-tetrahydro-5H-cyclohepta[b]pyridine-3-carboxylate

2-Formylcycloheptanone (1.70 g, 12.1 mmol) and ethyl 3-aminocrotonate (1.58 g, 12.1 mmol) were stirred at 100° C. for 15 hours. After cooling, the reaction solution was purified by a silica gel column chromatography (ether/hexane=1:3) to obtain the title compound (1.35 g, 46.1%) as pale yellow powder.

Melting point: 53–54° C. IR (KBr) $\nu_{max}$: 2980, 2928, 2852, 1728, 1600, 1444, 1282, 1254, 1198, 1146 $cm^{-1}$. $^1$H-NMR (CDCl$_3$) δ: 1.39 (3 H, t, J=7.0 Hz), 1.40–2.02 (6 H, m), 2.76 (3 H, s), 2.55–2.85 (2 H, m), 2.85–3.13 (2 H, m), 4.36 (2 H, q, J=7.0 Hz), 7.87 (1 H, s).

REFERENCE EXAMPLE 5

Ethyl 2-methyl-5,6,7,8-tetrahydrocyclohexa[b]pyridine-3-carboxylate

In the same manner as described in Reference Example 4, the title compound (2.81 g, 51.3%) was obtained as pale yellow oil from 2-formylcyclohexanone (3.15 g, 25.0 mmol) and ethyl 3-aminocrotonate (3.26 g, 25.0 mmol).

IR (neat) $v_{max}$: 2980, 2936, 1860, 1722, 1600, 1556, 1450, 1410, 1312, 1270, 1250, 1236, 1154, 1060, 782 cm$^{-1}$. $^1$H-NMR (CDCl$_3$) δ: 1.39 (3 H, t, J=7.0 Hz), 1.71–1.88 (4 H, m), 2.76 (3 H, s), 2.76–2.90 (4 H, m), 4.36 (2 H, q, J=7.0 Hz), 7.86 (1 H, s).

REFERENCE EXAMPLE 6

Ethyl 2-methyl-5,6,7,8,9,10-hexahydrocycloocta[b]pyridine-3-carboxylate

In the same manner as described in Reference Example 4, the title compound (2.27 g, 46.0%) was obtained as pale yellow powder from 2-formylcyclooctanone (3.08 g, 20.0 mmol) and ethyl 3-aminocrotonate (2.71 g, 21.0 mmol).

Melting point: 40–42° C. IR (KBr) $v_{max}$: 2968, 2852, 1722, 1596, 1554, 1452, 1398, 1360, 1262, 1200, 1136, 1070 cm$^{-1}$. $^1$H-NMR (CDCl$_3$) δ: 1.20–2.20 (8 H, m), 1.40 (3 H, t, J=7.3 Hz), 2.78 (3 H, s), 2.56–2.85 (2 H, m), 2.85–3.10 (2 H, m), 4.37 (2 H, q, J=7.3 Hz), 7.88 (1 H, s).

REFERENCE EXAMPLE 7

Ethyl 2-phenyl-6,7,8,9-tetrahydro- 5H-cyclohepta[b]pyridine-3-carboxylate

In the same manner as described in Reference Example 4, the title compound (1.35 g, 56.3%) was obtained as white powder from 2-formylcycloheptanone (1.13 g, 8.09 mmol) and ethyl 3-amino-3-phenylacrylate (1.54 g, 8.06 mmol).

Melting point: 94–95° C. IR (KBr) $v_{max}$: 3916, 1708, 1452, 1430, 1414, 1322, 1296, 1282, 1250, 1226, 1206, 1150, 1110, 1014, 774, 704, 698 cm$^{-1}$. $^1$H-NMR (CDCl$_3$) δ: 1.03 (3 H, t, J=7.0 Hz), 1.72–1.81 (6 H, m), 2.81–2.91 (2 H, m), 3.08–3.18 (2 H, m), 4.12 (2 H, q, J=7.0 Hz), 7.38–7.46 (5 H, m), 7.80 (1 H, s).

REFERENCE EXAMPLE 8

Ethyl 2-isopropyl-6,7,8,9-tetrahydro-5H-cyclohepta[b]pyridine-3-carboxylate

In the same manner as described in Reference Example 4, the title compound (722.2 mg, 23.5%) was obtained as pale orange amorphous from 2-formylcycloheptanone (3.29 g, 22.9 mmol) and ethyl 3-amino-3-isopropylacrylate (1.85 g, 11.7 mmol).

IR (KBr) $v_{max}$: 2960, 2924, 2852, 1722, 1554, 1444, 1280, 1262, 1236, 1196, 1144, 1124, 1098, 1040 cm$^{-1}$. $^1$H-NMR (CDCl$_3$) δ: 1.27 (6 H, d, J=6.8 Hz), 1.38 (3 H, t, J=7.0 Hz), 1.65–1.93 (6 H, m), 2.70–2.81 (2 H, m), 2.99–3.04 (2 H, m), 3.69–3.77 (1 H, m), 4.35 (2 H, q, J=7.0 Hz), 7.70 (1 H, s).

REFERENCE EXAMPLE 9

Ethyl 2-ethyl-6,7,8,9-tetrahydro-5H-cyclohepta[b]pyridine-3-carboxylate

In the same manner as described in Reference Example 4, the title compound (689.4 mg, 26.5%) was obtained as colorless oil from 2-formylcycloheptanone (1.47 g, 10.5 mmol) and ethyl 3-amino-3-ethylacrylate (1.50 g, 10.5 mmol).

IR (neat) $v_{max}$: 2976, 2928, 2852, 1720, 1596, 1556, 1442, 1278, 1252, 1232, 1198, 1144, 1120, 1064, 1048 cm$^{-1}$. $^1$H-NMR (CDCl$_3$) δ: 1.27 (3 H, t, J=7.5 Hz), 1.39 (3 H, t, J=7.0 Hz), 1.70–1.87 (6 H, m), 2.73–2.83 (2 H, m), 2.98–3.10 (2 H, m), 3.10 (2 H, q, J=7.5 Hz), 4.36 (2 H, q, J=7.0 Hz), 7.83 (1 H, s).

REFERENCE EXAMPLE 10

Ethyl 2-trifluoromethyl-6,7,8,9-tetrahydro-5H-cyclohepta[b]pyridine-3-carboxylate In the same manner as described in Reference Example 4, the title compound (1.14 g, 32.2%) was obtained as yellow oil from 2-formylcycloheptanone (2.58 g, 18.4 mmol) and ethyl 3-amino-4-trifluorocrotonate (2.35 g, 12.3 mmol).

IR (neat) $v_{max}$: 2932, 2856, 1736, 1598, 1460, 1446, 1370, 1338, 1314, 1284, 1260, 1206, 1176, 1144, 1118, 1032, 1018 cm$^{-1}$. $^1$H-NMR (CDCl$_3$) δ: 1.38 (3 H, t, J=7.0 Hz), 1.70–1.90 (6H, m), 2.81–2.92 (2 H, m), 3.07–3.19 (2 H, m), 4.39 (2 H, q, J=7.0 Hz), 7.74 (1 H, s).

REFERENCE EXAMPLE 11

Methyl 2-methoxymethyl-6,7,8,9-tetrahydro-5H-cyclohepta[b]pyridine-3-carboxylatl In the same manner as described in Reference Example 4, the title compound (953.2 mg, 50.9%) was obtained as yellow oil from 2-formylcycloheptanone (1.07 g, 7.60 mmol) and methyl 3-amino-3-methoxymethylacrylate (1.10 g, 7.51 mmol).

IR (neat) $v_{max}$: 2924, 2852, 1728, 1678, 1650, 1592, 1436, 1280, 1270, 1244, 1200, 1162, 1148, 1114, 1052, 940 cm$^{-1}$. $^1$H-NMR (CDCl$_3$) δ: 1.56–1.71 (6 H, m), 2.75–2.86 (2 H, m), 3.05–3.16 (2 H, m), 3.46 (3 H, s), 3.90 (3 H, s), 4.85 (2 H, s), 7.87 (1 H, s).

REFERENCE EXAMPLE 12

Ethyl 2-(3-pyridyl)-6,7,8,9-tetrahydro-5H-cyclohepta[b]pyridine-3-carboxylate In the same manner as described in Reference Example 4, the title compound (2.22 g, 62.7%) was obtained as brown oil from 2-formylcycloheptanone (2.54 g, 18.0 mmol) and ethyl 3-amino-3-(3-pyridyl acrylate (2.29 g, 11.9 mmol).

IR (neat) $v^{max}$: 2824, 2852, 1720, 1692, 1588, 1432, 1414, 1364, 1296, 1272, 1250, 1200, 1148, 1110, 1044, 1028, 706 cm$^{-1}$. $^1$H-NMR (CDCl$_3$) δ: 1.08 (3 H, t, J=7.0 Hz), 1.73–1.93 (6 H, m), 2.83–2.94 (2 H, m), 3.08–3.19 (2 H, m), 4.16 (2 H, q, J=7.0 Hz), 7.26–7.41 (2 H, m), 7.80 7.91 (1 H, m), 7.91 (1 H, s), 8.58–8.75 (2 H, m).

REFERENCE EXAMPLE 13

Ethyl 2-(1-methylpyrrolylmethyl-2-yl)-6,7,8,9-tetrahydro-5H-cyclohepta[b]pyridine-3-carboxylate In the same manner as described in Reference Example 4, the title compound (642.6 mg, 20.8%) was obtained as brown oil from 2-formylcycloheptanone (2.08 g, 14.9 mmol) and ethyl 3-amino-3-(1-methylpyrrolylmethyl-2-yl) acrylate (2.05 g, 9.89 mmol).

IR (neat) $v_{max}$: 2980, 2924, 2852, 1720, 1596, 1492, 1444, 1414, 1366, 1266, 1200, 1146, 1114, 1052, 704 cm$^{-1}$.

¹H-NMR (CDCl₃) δ: 1.32 (3 H, t, J=7.0 Hz), 1.60–1.87 (6 H, m), 2.73–2.83 (2 H, m), 2.98–3.09 (2 H, m), 3.64 (3 H, s), 4.30 (2 H, q, J=7.0 Hz), 4.46 (2 H, s), 5.92–5.99 (2 H, m), 6.47–6.52 (1 H, m), 7.83 (1 H, s).

REFERENCE EXAMPLE 14

Ethyl 2-(2-thienyl)-6,7,8,9-tetrahydro-5H-cyclohepta[b]pyridine-3-carboxylate

In the same manner as described in Reference Example 4, the title compound (2.47 g, 50.1%) was obtained as pale yellow oil from 2-formylcycloheptanone (3.45 g, 24.6 mmol) and ethyl 3-amino-3-(2-thienyl)acrylate (3.24 g, 16.4 mmol).

IR (neat) $v_{max}$: 2924, 2852, 1724, 1592, 1550, 1454, 1440, 1406, 1288, 1244, 1222, 1200, 1146, 1116, 1098, 1070, 704 cm⁻¹. ¹H-NMR (CDCl₃) δ: 1.25 (3 H, t, J=7.0 Hz), 1.70–1.92 (6 H, m), 2.76–2.87 (2 H, m), 3.04–3.14 (2 H, m), 4.29 (2 H, q, J=7.0 Hz), 7.03 (1 H, dd, J=4.6, 4.0 Hz), 7.26–7.41 (2 H, m), 7.63 (1 H, s).

REFERENCE EXAMPLE 15

Ethyl 2-fluoromethyl-6,7,8,9-tetrahydro-5H-cyclohepta[b]pyridine-3-carboxylate

In the same manner as described in Reference Example 4, the title compound (1.54 g, 30.6%) was obtained as yellow oil from 2-formylcycloheptanone (2.80 g, 20.0 mmol) and ethyl 3-amino-3-fluoromethylacrylate (3.58 g, 24.3 mmol).

IR (neat) $v_{max}$: 2928, 2852, 1720, 1594, 1562, 1444, 1372, 1320, 1270, 1246, 1200, 1146, 1118, 1096, 1056, 1030, 992, 960 cm⁻¹. ¹H-NMR (CDCl₃) δ: 1.40 (3 H, t, J=7.0 Hz), 1.69–1.79 (6 H, m), 2.79–2.89 (2 H, m), 3.07–3.18 (2 H, m), 4.38 (2 H, q, J=7.0 Hz), 5.51 (1 H, s), 6.04 (1 H, s), 7.95 (1 H, s).

REFERENCE EXAMPLE 16

Ethyl 2,8-dimethyl-5,6,7,8-tetrahydrocyclohexa[b]pyridine-3-carboxylate

In the same manner as described in Reference Example 4, the title compound (1.93 g, 44.1%) was obtained as yellow oil from 2-formyl-6-methylcyclohexanone (2.63 g, 18.7 mmol) and ethyl 3-aminocrotonate (2.43 g, 18.9 mmol).

IR (neat) $v_{max}$: 2932, 2864, 1724, 1598, 1554, 1446, 1268, 1234, 1154, 1066 cm⁻¹. ¹H-NMR (CDCl₃) δ: 1.35 (3 H, d, J=6.8 Hz), 1.39 (3 H, t, J=7.0 Hz), 1.68–2.05 (4 H, m), 2.76 (3 H, s), 2.76–2.95 (3 H, m), 4.35 (2 H, q, J=7.0 Hz), 7.84 (1 H, s).

REFERENCE EXAMPLE 17

Ethyl 2,6-dimethyl-5,6,7,8-tetrahydrocyclohexa[b]pyridine-3-carboxylate

In the same manner as described in Reference Example 4, the title compound (1.28 g, 23.2%) was obtained as yellow oil from 2-formyl-4-methylcyclohexanone (3.32 g, 23.7 mmol) and ethyl 3-aminocrotonate (3.06 g, 23.7 mmol).

IR (neat) $v_{max}$: 2952, 2928, 2872, 1720, 1598, 1558, 1448, 1410, 1366, 1268, 1234, 1216, 1158, 1094, 1074, 1052, 782 cm⁻¹. ¹H-NMR (CDCl₃) δ: 1.08 (3 H, d, J=6.2 Hz), 1.21–2.27 (4 H, m), 1.39 (3 H, t, J=7.0 Hz), 2.42–2.53 (1 H, m), 2.76 (3 H, s), 2.86–3.43 (2 H, m), 4.36 (2 H, q, J=7.0 Hz), 7.85 (1 H, s).

REFERENCE EXAMPLE 18

Ethyl 8-methoxy-2-methyl-5,6,7,8-tetrahydrocyclohexa[b]pyridine-3-carboxylate

In the same manner as described in Reference Example 4, the title compound (1.22 g, 58.8%) was obtained as yellow oil from 2-formyl-6-methoxycyclohexanone (1.30 g, 8.32 mmol) and ethyl 3-aminocrotonate (1.08 g, 8.37 mmol).

IR (neat) $v_{max}$: 2976, 2940, 2824, 1724, 1598, 1558, 1446, 1414, 1304, 1266, 1234, 1172, 1144, 1092, 1056, 902, 792, 754 cm⁻¹. ¹H-NMR (CDCl₃) δ: 1.39 (3 H, t, J=7.3 Hz), 1.78–2.26 (4 H, m), 2.27–3.42 (2 H, m), 2.80 (3 H, s), 3.54 (3 H, s), 4.36 (2 H, q, J=7.3 Hz), 7.92 (1 H, s).

REFERENCE EXAMPLE 19

Ethyl 6-ethylenedioxy-2-methyl-5,6,7,8-tetrahydrocyclohexa[b]pyridine-3-carboxylate In the same manner as described in Reference Example 4, the title compound (4.00 g, 50.2%) was obtained as yellowish brown powder from 3-formyl-1,4-cyclohexadione monoethylene ketal (5.29 g, 28.7 mmol) and ethyl 3-aminocrotonate (3.94 g, 30.2 mmol).

Melting point: 59–65° C. IR (KBr) $v_{max}$: 2974, 2902, 1716, 1499, 1296, 1272, 1257, 1242, 1173, 1155, 1101, 1059 cm⁻¹. ¹H-NMR (CDCl₃) δ: 1.38 (3 H, t, J=7.0 Hz), 2.05 (2 H, t, J=6.8 Hz), 2.77 (3 H, s), 2.89–3.25 (2 H, m), 3.13 (2 H, t, J=6.8 Hz), 4.03 (3 H, s), 4.35 (2 H, q, J=7.0 Hz), 7.86 (1 H, br-s).

REFERENCE EXAMPLE 20

Ethyl 2-methyl-6-oxa-7,8-dihydrocyclohexa[b]pyridine-3-carboxylate

In the same manner as described in Reference Example 4, the title compound (758.0 mg, 24.8%) was obtained as yellow powder from 3-formyl-tetrahydropyran-4-one (1.77 g, 13.8 mmol) and ethyl 3-aminocrotonate (1.89 g, 14.5 mmol).

Melting point: 61–65° C. IR (KBr) $v_{max}$: 2968, 2932, 2872, 1725, 1563, 1290, 1269, 1239, 1158, 1056, 1020 cm⁻¹. ¹H-NMR (CDCl₃) δ: 1.39 (3 H, t, J=7.0 Hz), 2.79 (3 H, s), 3.00 (2 H, t, J=5.7 Hz), 4.07 (2 H, t, J=5.7 Hz), 4.36 (2 H, q, J=7.0 Hz), 4.76 (2 H, s), 7.83 (1 H, br-s).

REFERENCE EXAMPLE 21

Ethyl 2,9-dimethyl-6,7,8,9-tetrahydro-5H-cyclohepta[b]pyridine-3-carboxylate

In the same manner as described in Reference Example 4, the title compound (1.06 g, 42.1%) was obtained as pale yellow oil from 2-formyl-7-methylcycloheptanone (1.56 g, 10.2 mmol) and ethyl 3-aminocrotonate (1.29 g, 10.2 mmol).

IR (neat) $v_{max}$: 2972, 2928, 2852, 1722, 1656, 1598, 1554, 1442, 1410, 1376, 1364, 1278, 1246, 1194, 1152, 1132, 1072, 1046, 786 cm⁻¹. ¹H-NMR (CDCl₃) δ: 1.35 (3 H, d, J=6.8 Hz), 1.41 (3 H, t, J=7.0 Hz), 1.47–1.98 (6 H, m), 2.76 (3 H, s), 2.76–2.86 (2 H, m), 3.04–3.33 (1 H, m), 4.35 (2 H, q, J=7.0 Hz), 7.83 (1 H, s).

REFERENCE EXAMPLE 22

Ethyl 2,8,8-trimethyl-5,6,7,8-tetrahydrocyclohexa[b]pyridine-3-carboxylate

In the same manner as described in Reference Example 4, the title compound (748.0 mg, 45.8%) was obtained as yellow oil from 2-formyl-6,6-dimethylcyclohexanone (1.02 g, 6.61 mmol) and ethyl 3-aminocrotonate (935.7 mg, 7.17 mmol).

IR (neat) $v_{max}$: 2936, 2868, 1724, 1600, 1552, 1474, 1446, 1410, 1378, 1296, 1270, 1236, 1206, 1166, 1112, 1062 cm⁻¹.

$^1$H-NMR (CDCl$_3$) δ: 1.31 (6 H, s), 1.38 (3 H, t, J=7.0 Hz), 1.74–1.82 (4 H, m), 2.74 (3 H, s), 2.74–2.82 (2 H, m), 4.34 (2 H, q, J=7.0 Hz), 7.80 (1 H, s).

REFERENCE EXAMPLE 23

Ethyl 2-methyl-6,7,8,9-tetrahydro-5H-cyclohepta[b]pyridine-3-carboxylate N-oxide In an atmosphere of argon, ethyl 2-methyl-6,7,8,9-tetrahydro-5H-cyclohepta[b]pyridine-3-carboxylate (13.50 g, 57.9 mmol) was dissolved in methylene chloride (300.0 ml) to which was subsequently added metachloroperbenzoic acid (87.9%, 14.79 g, 75.3 mmol) in small portions at 0° C., and the resulting mixture was stirred at the same temperature for 2 hours and then at room temperature for 10 hours. The reaction solution was mixed with saturated sodium bicarbonate aqueous solution at 0° C. and extracted with methylene chloride, and the thus obtained organic layer was washed with saturated sodium bicarbonate aqueous solution, water and saturated brine in that order and then dried over anhydrous sodium sulfate. The solvent was evaporated under reduced pressure, and the resulting residue was purified by a silica gel column chromatography (ethyl acetate:hexane=5:1—ethyl acetate) to obtain the title compound (10.80 g, 74.9%) as white powder.

Melting point: 67–69° C. IR (KBr) ν$_{max}$: 2996, 2848, 1710, 1479, 1383, 1320, 1248, 1140, 1050, 975 cm$^{-1}$. $^1$H-NMR (CDCl$_3$) δ: 1.40 (3 H, t, J=7.0 Hz), 1.50–2.10 (6 H, m), 2.77 (3 H, s), 2.60–2.90 (2 H, m), 3.30–3.56 (2 H, m), 4.38 (2 H, q, J=7.0 Hz), 7.42 (1 H, s).

REFERENCE EXAMPLE 24

2-Methyl-6,7,8,9-tetrahydro-5H-cyclohepta[b]pyridine-3-carboxylic acid

Ethyl 2-methyl-6,7,8,9-tetrahydro-5H-cyclohepta[b]pyridine-3-carboxylate (3.05 g, 13.1 mmol) was suspended in 5% sodium hydroxide aqueous solution (20.0 ml) and heated under reflux for 1 hour. After cooling to room temperature, this was adjusted to pH 4 by adding concentrated hydrochloric acid and extracted with chloroform-methanol (4:1) mixed solvent. The thus obtained organic layer was washed with saturated brine and then dried over anhydrous sodium sulfate. By evaporating the solvent under reduced pressure, the title compound (1.95 g, 72.7%) was obtained as pale brown powder.

Melting point: 167–169° C. IR (KBr) ν$_{max}$: 2920, 2852, 1704, 1570, 1446, 1284, 1260, 1202, 1190, 1148, 1122, 1042, 962, 766 cm$^{-1}$. $^1$H-NMR (CDCl$_3$-CD$_3$OD) δ: 1.67–1.89 (6 H, m), 2.68–2.76 (2 H, m), 2.83 (3 H, s), 3.05–3.16 (2 H, m), 8.04 (1 H, s).

REFERENCE EXAMPLE 25

Ethyl 9-acetoxy-2-methyl-6,7,8,9-tetrahydro-5H-cyclohepta[b]pyridine-3-carboxylate Ethyl 2-methyl-6,7,8,9-tetrahydro-5H-cyclohepta[b]pyridine-3-carboxylate N-oxide (1.00 g, 4.02 mmol) was dissolved in acetic anhydride (7.0 ml) and heated under reflux for 1.5 hours. After cooling, excess acetic anhydride was evaporated under reduced pressure, the thus obtained residue was mixed with ice water and saturated sodium bicarbonate aqueous solution and extracted with ethyl acetate, and the resulting organic layer was washed with water and saturated brine in that order and dried over anhydrous sodium sulfate. The solvent was evaporated under reduced pressure, and the resulting residue was purified by a silica gel column chromatography (ether:hexane=1:1) to obtain the title compound (482.5 mg, 45.8%) as pale brown oil.

IR (neat) ν$_{max}$: 2928, 2856, 1742, 1722, 1596, 1562, 1444, 1366, 1238, 1146, 1058 cm$^{-1}$. $^1$H-NMR (CDCl$_3$) δ: 1.38 (3 H, t, J=7.0 Hz), 1.50–2.05 (6 H, m), 2.18 (3 H, s), 3.00–3.18 (2 H, m), 4.35 (2 H, q, J=7.0 Hz), 5.70–6.00 (1 H, m), 7.89 (1 H, s).

REFERENCE EXAMPLE 26

2-Chloro-3-cyano-6,7,8,9-tetrahydro-5H-cyclohepta[b]pyridine

In an atmosphere of argon, metallic sodium (9.57 g, 0.41 g atom) was suspended in ether (300.0 ml) to which was subsequently added dropwise a mixed solution of cycloheptanone (45.30 g, 402.0 mmol) and ethyl formate (30.00 g, 402.0 mmol) at 0° C. This was stirred at room temperature for 1.5 hours, ether was evaporated under reduced pressure, and then an aqueous solution (230.0 ml) of cyanoacetamide (95%, 36.30 g, 411.0 mmol) was added dropwise to the thus obtained reaction mixture. After dropwise addition of an aqueous solution (9.9 ml) of acetic acid (4.02 ml) at room temperature, the reaction solution was alkalified by adding piperidine and heated under reflux for 2 hours. The reaction solution was mixed with water (60.0 ml) at 0° C., stirred at the same temperature for 2 hours and then acidified with acetic acid to effect precipitation of crystals. The crystals were collected by filtration, washed with water and ether and then dried to obtain crude pyridone compound (29.07 g, 38.5%) as brown powder. The crude pyridone compound (29.00 g, 154.3 mmol) was added to phosphorus oxychloride (140.0 ml) at room temperature and. then heated under reflux for 15 hours. After cooling, excess phosphorus oxychloride was evaporated under reduced pressure, and the thus obtained residue was poured into ice water, adjusted to pH 7 to 8 with 40% sodium hydroxide aqueous solution at 0° C. and then extracted with methylene chloride. The thus obtained organic layer was washed with water and saturated brine in that order and dried over anhydrous sodium sulfate. The solvent was evaporated under reduced pressure, and the resulting residue was purified by a silica gel column chromatography (methylene chloride:hexane=1:1–5:1) to obtain the title compound (18.77 g, 58.9%) as white powder.

Melting point: 126–127° C. IR (KBr) ν$_{max}$: 3040, 2964, 2928, 2232, 1582, 1536, 1448, 1420, 1386, 1188, 1156, 1032, 934 cm$^{-1}$. $^1$H-NMR (CDCl$_3$) δ: 1.40–2.10 (6 H, m), 2.60–2.90 (2 H, m), 2.91–3.20 (2 H, m), 7.65 (1 H, s).

REFERENCE EXAMPLE 27

Methyl 2-chloro-6,7,8,9-tetrahydro-5H-cyclohepta[b]pyridine-3-carboxylate

2-Chloro-3-cyano-6,7,8,9-tetrahydro-5H-cyclohepta[b]pyridine (1.50 g, 7.26 mmol) was suspended in 5% sodium hydroxide aqueous solution (25.0 ml) and heated under reflux for 3.5 hours. The reaction solution was adjusted to pH 3 to 4 with concentrated hydrochloric acid and 5% hydrochloric acid at 0° C. and extracted with chloroform, and the thus obtained organic layer was washed with water and saturated brine in that order and dried over anhydrous sodium sulfate. The solvent was evaporated under reduced pressure, and the thus formed crude crystals were washed with ether to obtain crude carboxylic acid. The crude carboxylic acid was dissolved in chloroform (20.0 ml) to which was subsequently added dropwise ether solution of diazomethane at 0° C. until the material crude carboxylic acid disappeared. Formic acid was added dropwise to the reaction solution at 0° C. to effect decomposition of excess diazomethane, the resulting solution was mixed with saturated sodium bicarbonate aqueous solution and extracted with methylene chloride, and then the thus obtained organic layer was washed with water and saturated brine in that order and dried over anhydrous sodium sulfate. After evaporation of the solvent under reduced pressure, the resulting residue was purified by a silica gel column chromatography (ether:hexane=2:1) to obtain the title compound (1.50 g, 86.3%) as white powder.

Melting point: 148–149° C. IR (KBr) $v_{max}$: 3452, 2936, 2852, 1730, 1588, 1546, 1450, 1376, 1290, 1204, 1148, 1032, 964 cm$^{-1}$. $^1$H-NMR (CDCl$_3$) δ: 1.45–2.05 (6 H, m), 2.60–2.86 (2 H, m), 2.86–3.16 (2 H, m), 3.93 (3 H, s), 7.87 (1 H, s).

REFERENCE EXAMPLE 28

3-Cyano-2-methoxy-6,7,8,9-tetrahydro-5H-cyclohepta[b]pyridine

In an atmosphere of argon, metallic sodium (230.0 mg, 0.01 g atom) was dissolved in methanol (10.0 ml) at room temperature, a methanol solution (10.0 ml) of 2-chloro-3-cyano-6,7,8,9-tetrahydro-5H-cyclohepta[b]pyridine (1.03 g, 5.00 mmol) was added dropwise thereto at the same temperature and then the resulting mixture was stirred at 60° C. for 6 hours. After cooling, methanol was evaporated under reduced pressure, the thus obtained residue was mixed with water and extracted with chloroform, and the resulting organic layer was washed with water and saturated brine in that order and dried over anhydrous sodium sulfate. After evaporation of the solvent under reduced pressure, the resulting residue was purified by a silica gel column chromatography (methylene chloride:hexane=2:1) to obtain the title compound (933.8 mg, 92.5%) as white powder.

Melting point: 83.5–84° C. IR (KBr) $v_{max}$: 2946, 2920, 2856, 2224, 1596, 1472, 1422, 1358, 1226, 1166, 1000 cm$^{-1}$. $^1$H-NMR (CDCl$_3$) δ: 1.40–2.03 (6 H, m), 2.55–2.80 (2 H, m), 2.80–3.10 (2 H, m), 4.01 (3 H, s), 7.52 (1 H, s).

REFERENCE EXAMPLE 29

Methyl 2-methoxy-6,7,8,9-tetrahydro-5H-cyclohepta[b]pyridine-3-carboxylate

In the same manner as described in Reference Example 27, the title compound (521.9 mg, 49.8%) was obtained as colorless oil from 3-cyano-2-methoxy-6,7,8,9-tetrahydro-5H-cyclohepta[b]pyridine (900.0 mg, 4.46 mmol).

IR (neat) $v_{max}$: 3480, 2950, 2860, 1750, 1680, 1610, 1480, 1305, 1205, 1190, 1120, 1090 cm$^{-1}$. $^1$H-NMR (CDCl$_3$) δ: 1.40–2.05 (6 H, m), 2.55–2.83 (2 H, m), 2.83–3.06 (2 H, m), 3.87 (3 H, s), 7.86 (1 H, s).

REFERENCE EXAMPLE 30

Methyl 6,7,8,9-tetrahydro-5H-cyclohepta[b]pyridine-3-carboxylate

After suspending 10% palladium-carbon (600.0 mg) in methanol (15.0 ml), the suspension was stirred at room temperature for 30 minutes in an atmosphere of hydrogen. A methanol solution (30.0 ml) of methyl 2-chloro-6,7,8,9-tetrahydro-5H-cyclohepta[b]pyridine-3-carboxylate (3.00 g, 12.5 mmol) was added to the reaction solution and stirred at room temperature for 18 hours in an atmosphere of hydrogen. After removing the catalyst by filtration, the thus obtained residue was washed with methanol, the solvent was evaporated under reduced pressure and then the resulting residue was purified by a silica gel column chromatography (ether:hexane=1:1) to obtain the title compound (2.57 g, quantitative) as white powder Melting point: 129–131° C. IR (KBr) $v_{max}$: 2936, 2516, 1732, 1432, 1416, 1298, 1274, 1226, 990 cm$^{-1}$. $^1$H-NMR (CDCl$_3$) δ: 1.58–2.28 (6 H, m), 2.80–3.20 (2 H, m), 3.35–3.75 (2 H, m), 4.00 (3 H, s), 8.59 (1 H, d, J=2.0 Hz), 9.03 (1 H, d, J=2.0 Hz).

REFERENCE EXAMPLE 31

Methyl 6,7,8,9-tetrahdro-5H-cyclohepta[b]pyridine-3-carboxylate N-oxide

In the same manner as described in Reference Example 23, the title compound (2.15 g, 90.2%) was obtained as white powder from methyl 6,7,8,9-tetrahydro-5H-cyclohepta[b]pyridine-3-carboxylate (1.90 g, 9.27 mmol).

Melting point: 112–114° C. IR (KBr) $v_{max}$: 2920, 1722, 1450, 1406, 1340, 1308, 1270, 1226, 1194, 1106, 944 cm$^{-1}$. $^1$H-NMR (CDCl$_3$) δ: 1.45–2.10 (6 H, m), 2.70–2.96 (2 H, m), 3.25–3.56 (2 H, m), 3.93 (3 H, s), 7.56 (1 H, d, J=2.0 Hz), 8.71 (1 H, d, J=2.0 Hz).

REFERENCE EXAMPLE 32

Methyl 9-acetoxy-6,7,8,9-tetrahydro-5H-cyclohepta[b]pyridine-3-carboxylate

In the same manner as described in Reference Example 25, the title compound (1.60 g, 74.6%) was obtained as pale yellow powder from methyl 6,7,8,9-tetrahydro-5H-cyclohepta[b]pyridine-3-carboxylate N-oxide (2.10 g, 8.17 mmol).

Melting point: 112–114° C. IR (KBr) $v_{max}$: 2940, 1742, 1720, 1602, 1442, 1386, 1314, 1230, 1156, 1050, 1034, 996 cm$^{-1}$. $^1$H-NMR (CDCl$_3$) δ: 1.40–2.30 (6 H, m), 2.20 (3 H, s), 2.73–3.10 (2 H, m), 3.92 (3 H, s), 5.80 (1 H, br-s), 8.00 (1 H, d, J=2.0 Hz), 8.96 (1 H, d, J=2.0 Hz).

REFERENCE EXAMPLE 33

Ethyl 2-methyl-4-nitro-6,7,8,9-tetrahydro-5H-cyclohepta[b]pyridine-3-carboxylate N-oxide Fuming nitric acid (27.0 ml) was added dropwise to ethyl 2-methyl-6,7,8,9-tetrahydro-5H-cyclohepta[b]pyridine-3-carboxylate N-oxide (3.10 g, 12.4 mmol) at 0° C., and the mixture was stirred at 90° C. for 2 hours. After cooling, the reaction solution was poured into ice water, mixed with 2 N sodium hydroxide aqueous solution and extracted with chloroform, and the thus obtained organic layer was washed with water and saturated brine in that order and dried over anhydrous sodium sulfate. After evaporation of the solvent under reduced pressure, the resulting residue was purified by a silica gel column chromatography (chloroform:methanol=40:1) to obtain the title compound (3.38 g, 92.4%) as pale yellow powder.

Melting point: 91–93° C. IR (KBr) $v_{max}$: 2948, 1728, 1568, 1528, 1422, 1398, 1386, 1358, 1340, 1320, 1304, 1258, 1218, 1114, 1054, 1012 cm$^{-1}$. $^1$H-NMR (CDCl$_3$) δ: 1.35 (3 H, t, J=7.0 Hz), 1.70–1.95 (6 H, m), 2.56 (3 H, s), 2.77–3.10 (4 H, m), 4.38 (2 H, q, J=7.0 Hz).

REFERENCE EXAMPLE 34

Ethyl 2-methyl-4-nitro-6,7,8,9-tetrahydro-5H-cyclohepta[b]pyridine-3-carboxylate Phosphorus tribromide (3.51 g, 12.5 mmol) was dissolved in ethyl acetate (12.0 ml) to which was subsequently added dropwise ethyl acetate solution (10.0 ml) of ethyl 2-methyl-4-nitro-6,7,8,9-tetrahydro-5H-cyclohepta[b]pyridine-3-carboxylate N-oxide (1.47 g, 5.00 mmol) at room temperature, and the resulting mixture was stirred at the same temperature for 10 minutes and then at 80° C. for 15 minutes. After cooling, the reaction solution was poured into ice water, mixed with saturated sodium bicarbonate aqueous solution and extracted with ethyl acetate, and the thus obtained organic layer was washed with water and saturated brine in that order and dried over anhydrous sodium sulfate. After evaporation of the solvent under reduced pressure, the resulting residue was purified by a silica gel column chromatography (ethyl acetate:hexane=2:1) to obtain the title compound (1.36 g, 97.9%) as pale brown oil.

IR (neat) $v_{max}$: 2928, 2856, 1734, 1632, 1594, 1546, 1446, 1412, 1384, 1368, 1280, 1254, 1206, 1146, 1132, 1054, 860, 752 cm$^{-1}$. $^1$H-NMR (CDCl$_3$) δ: 1.33 (3 H, t, J=7.3 Hz), 1.58–1.99 (6 H, m), 2.61–2.73 (2 H, m), 2.67 (3 H, s), 3.07–3.18 (2 H, m), 4.34 (2 H, q, J=7.3 Hz).

REFERENCE EXAMPLE 35

2-Methyl-4-nitro-6,7,8,9-tetrahydro-5H-cyclohepta[b]pyridine-3-carboxylic acid

In the same manner as described in Reference Example 24, the title compound (1.04 g, 86.2%) was obtained as pale brown powder from ethyl 2-methyl-4-nitro-6,7,8,9-tetrahydro-5H-cyclohepta[b]pyridine-3-carboxylate (1.35 g, 4.84 mmol).

Melting point: 168–171° C. IR (KBr) $v_{max}$: 2936, 1720, 1592, 1546, 1386, 1288, 1258, 1240, 1210, 1188, 1152, 1132, 1048, 960, 866, 784, 766, 736, 698 cm$^{-1}$. $^1$H-NMR (CDCl$_3$) δ: 1.74–1.80 (6 H, m), 2.55–2.71 (2 H, m), 2.71 (3 H, s), 3.07–3.18 (3 H, m).

REFERENCE EXAMPLE 36

Methyl 4-methoxy-2-methyl-6,7,8,9-tetrahydro-5H-cyclohepta[b]pyridine-3-carboxylate N-oxide In an atmosphere of argon and at room temperature, metallic sodium (86.0 mg, 0.005 g atom) was dissolved in anhydrous methanol (8.0 ml) to which was subsequently added dropwise methanol solution (20.0 ml) of ethyl 2-methyl-4-nitro-6,7,8,9-tetrahydro-5H-cyclohepta[b]pyridine-3-carboxylate N-oxide (1.00 g, 3.40 mmol), and the resulting mixture was stirred at room temperature for 29 hours. After evaporation of the solvent under reduced pressure, the resulting residue was mixed with water and extracted with chloroform, and the thus obtained organic layer was washed with water and saturated brine in that order and dried over anhydrous sodium sulfate. After evaporation of the solvent under reduced pressure, the resulting residue was purified by a silica gel column chromatography (ethyl acetate:hexane=5:1—ethyl acetate:methanol=15:1) to obtain the title compound (777.9 mg, 86.3%) as pale yellow powder.

Melting point: 70–72° C. IR (KBr) $v_{max}$: 2920, 2856, 1734, 1434, 1348, 1298, 1228, 1060, 1024, 968, 956 cm$^{-1}$. $^1$H-NMR (CDCl$_3$) δ: 1.43–2.05 (6 H, m), 2.46 (3 H, s), 2.70–2.96 (2 H, m), 3.30–3.56 (2 H, m), 3.77 (3 H, s), 3.95 (3 H, s).

REFERENCE EXAMPLE 37

Methyl 4-methoxy-2-methyl-6,7,8,9-tetrahydro-5H-cyclohepta[b]pyridine-3-carboxylate Methanol (5.0 ml) was added to Raney nickel water suspension (0.2 ml) and stirred at room temperature for 30 minutes in an atmosphere of hydrogen. The reaction solution was mixed with methanol solution (6.0 ml) of methyl 4-methoxy-2-methyl-6,7,8,9-tetrahydro-5H-cyclohepta[b]pyridine-3-carboxylate N-oxide (607.9 mg, 2.29 mmol) and stirred at room temperature for 30 hours in an atmosphere of hydrogen. After removal of the catalyst by filtration, the resulting residue was washed with methanol, the solvent was evaporated under reduced pressure, and the thus obtained residue was dissolved in ethyl acetate and dried over anhydrous sodium sulfate. After evaporation of the solvent under reduced pressure, the resulting residue was purified by a silica gel column chromatography (ether:hexane=2:1) to obtain the title compound (567.8 mg, 99.6%) as colorless oil.

IR (neat) $v_{max}$: 2924, 2852, 1732, 1580, 1562, 1438, 1344, 1264, 1148, 1052, 968 cm$^{-1}$. $^1$H-NMR (CDCl$_3$) δ: 1.45–2.05 (6 H, m), 2.45 (3 H, s), 2.60–2.90 (2 H, m), 2.90–3.13 (2 H, m), 3.78 (3 H, s), 3.93 (3 H, s).

REFERENCE EXAMPLE 38

4-Methoxy-2-methyl-6,7,8,9-tetrahydro-5H-cyclohepta[b]pyridine-3-carboxylic acid In the same manner as described in Reference Example 24, the title compound (390.2 mg, 71.5%) was obtained as white powder from methyl 4-methoxy-2-methyl-6,7,8,9-tetrahydro-5H-cyclohepta[b]pyridine-3-carboxylate (546.5 mg, 2.32 mmol).

Melting point: 180–182° C. IR (KBr) $v_{max}$: 2924, 2852, 1604, 1466, 1448, 1404, 1372, 1344, 1272, 1198, 1146, 1100, 964, 926, 832, 768, 720, 602, 568 cm$^{-1}$. $^1$H-NMR (CDCl$_3$) δ: 1.55–1.79 (6 H, m), 2.70 (3 H, s), 2.79–2.90 (2 H, m), 3.12–3.14 (2 H, m), 4.26 (3 H, s).

REFERENCE EXAMPLE 39

Ethyl 2-methyl-5,6,7,8-tetrahydrocyclohexa[b]pyridine-3-carboxylate N-oxide

In the same manner as described in Reference Example 23, the title compound (8.78 g, 71.4%) was obtained as pale yellow amorphous from ethyl 2-methyl-5,6,7,8-tetrahydro-5H-cyclohexa[b]pyridine-3-carboxylate (11.36 g, 52.3 mmol).

IR (KBr) $v_{max}$: 2936, 2868, 1726, 1590, 1492, 1478, 1428, 1396, 1380, 1336, 1288, 1264, 1212, 1160, 1108, 1048, 1012, 912, 772 cm$^{-1}$. $^1$H-NMR (CDCl$_3$) δ: 1.40 (3 H, t, J=7.0 Hz), 1.65–1.98 (4 H, m), 2.78 (3 H, s), 2.78–3.04 (4 H, m), 4.38 (2 H, q, J=7.0 Hz), 7.47 (1 H, s).

REFERENCE EXAMPLE 40

Ethyl 8-acetoxy-2-methyl-5,6,7,8-tetrahydrocyclohexa[b]pyridine-3-carboxylate

In the same manner as described in Reference Example 25, the title compound (7.95 g, 76.9%) was obtained as yellow oil from ethyl 2-methyl-5,6,7,8-tetrahydrocyclohexa[b]pyridine-3-carboxylate N-oxide (8.78 g, 37.3 mmol).

IR (neat) $v_{max}$: 2940, 2872, 1734, 1600, 1560, 1448, 1414, 1370, 1306, 1268, 1232, 1176, 1150, 1086, 1064, 1018, 956, 788, 754 cm$^{-1}$. $^1$H-NMR (CDCl$_3$) δ: 1.39 (3 H, t, J=7.0 Hz), 1.79–2.18 (4 H, m), 2.11 (3 H, s), 2.76 (3 H, s), 2.76–2.86 (2 H, m), 4.37 (2 H, q, J=7.0 Hz), 5.86–5.96 (1 H, m)), 7.92 (1 H, s).

REFERENCE EXAMPLE 41

Ethyl 9-hydroxy-2-methyl-6,7,8,9-tetrahydro-5H-cyclohepta[b]pyridine-3-carboxylate Ethyl 9-acetoxy-2-methyl-6,7,8,9-tetrahydro-5H-cyclohepta[b]pyridine-3-carboxylate (4.90 g, 16.81 mmol)

was dissolved in ethanol (30 ml), and the solution was mixed with potassium carbonate (3.29 g) and stirred at from 0° C. to room temperature for 24 hours. There action solution was mixed with water and ethyl acetate, and the thus precipitated crystals were filtered. The resulting filtrate was extracted with ethyl acetate, and the thus obtained organic layer was washed with water and saturated brine in that order and dried over anhydrous sodium sulfate. By evaporating the solvent under reduced pressure, the title compound (3.31 g, 79.9%) was obtained as pale yellow amorphous.

IR (KBr) $v_{max}$: 2980, 2932, 2856, 1724, 1560, 1442, 1414, 1366, 1272, 1248, 1138, 1058, 754 cm$^{-1}$. $^1$H-NMR (CDCl$_3$) δ: 1.40 (3 H, t, J=7.0 Hz), 1.75–2.34 (6 H, m), 2.69–3.06 (2 H, m), 2.76 (3 H, s), 4.38 (2 H, q, J=7.0 Hz), 4.74 (1 H, d, J=10.3 Hz), 7.95 (1 H, s).

REFERENCE EXAMPLE 42

Ethyl 8-hydroxy-2-methyl-5,6,7,8-tetrahydrocyclohexa[b]pyridine-3-carboxylate

In the same manner as described in Reference Example 41, the title compound (2.92 g, 45.4%) was obtained as pale yellow amorphous from ethyl 8-acetoxy-2-methyl- 5,6,7,8-tetrahydrocyclohexa[b]pyridine-3-carboxylate (7.59 g, 27.4 mmol).

IR (KBr) $v_{max}$: 3176, 2984, 2936, 2888, 1720, 1562, 1446, 1400, 1296, 1270, 1246, 1234, 1176, 1150, 1080, 1058, 990 cm$^{-1}$. $^1$H-NMR (CDCl$_3$) δ: 1.40 (3 H, t, J=7.0 Hz), 1.65–2.38 (4 H, m), 2.78 (3 H, s), 2.78–2.89 (2 H, m), 4.08 (1 H, br-s), 4.37 (2 H, q, J=7.0 Hz), 4.56–4.71 (1 H, m), 7.92 (1 H, s).

REFERENCE EXAMPLE 43

Methyl 9-hydroxy-2-methyl-6,7,8,9-tetrahydro-5H-cyclohepta[b]pyridine-3-carboxylate 6,7,8,9-Tetrahydro-5H-cyclohepta[b]pyridine3,2-clfuran-3-one Ethyl 2-methyl-6,7,8,9-tetrahydro-5H-cyclohepta[b] pyridine-3-carboxylate N-oxide (8.00 g, 32.1 mmol) was dissolved in acetic anhydride (56.0 ml) and heated under reflux for 1.5 hours. After cooling, excess acetic anhydride was evaporated under reduced pressure, the thus obtained residue was mixed with ice water and 40% sodium hydroxide aqueous solution and extracted with ethyl acetate, and the resulting organic layer was washed with water and saturated brine in that order and dried over anhydrous sodium sulfate. The solvent was evaporated under reduced pressure, and the thus obtained reaction product (10.27 g, 32.1 mmol) was dissolved in methanol (40.0 ml), mixed with potassium carbonate (4.88 g) and stirred at 0° C. for 30 minutes. The reaction solution was mixed with water and ethyl acetate, and the thus precipitated crystals were collected by filtration to obtain pale yellow powder of 6,7,8,9-tetrahydro-5H-cyclohepta[b]pyrido[3,2-c]furan-3-one (2.69 g, 41.3%) as a low polar component The resulting filtrate was extracted with ethyl acetate, and the thus obtained organic layer was washed with water and saturated brine in that order and dried over anhydrous sodium sulfate. By evaporating the solvent under reduced pressure, methyl 9-hydroxy-2-methyl-6,7,8,9-tetrahydro-5H-cyclohepta[b] pyridine-3-carboxylate (4.20 g, 55.7%) was obtained in the form of white amorphous as a high polar component.
(Low polar component)

Melting point: 191–192° C. IR (KBr) $v_{max}$: 2936, 2860, 1764, 1606, 1590, 1450, 1436, 1416, 1354, 1172, 1134, 1110, 1092, 1018, 1004, 958, 942, 780, 758 cm$^{-1}$. $^1$H-NMR (CDCl$_3$) δ: 1.70–1.83 (6 H, m), 2.86–2.97 (2 H, m), 3.44–3.22 (2 H, m), 5.24 (2 H, s), 7.86 (1 H, s).
(High polar component)

IR (KBr) $v_{max}$: 3356, 2924, 2852, 1718, 1596, 1568, 1438, 1406, 1276, 1244, 1196, 1134, 1092, 1084, 1070, 786 cm$^{-1}$. $^1$H-NMR (CDCl$_3$) δ: 1.75–2.33 (6 H, m), 2.69–2.81 (2 H, m), 2.81 (3 H, s), 3.91 (3 H, s), 4.67–4.81 (1 H, dd, J=10.5, 2.0 Hz), 7.96 (1 H, s).

REFERENCE EXAMPLE 44

Methyl 8-hydroxy-2-methyl-5,6,7,8-tetrahydrocyclohexa[b]pyridine-3-carboxylate

Ethyl 8-acetoxy-2-methyl-5,6,7,8-tetrahydrocyclohexa[b] pyridine-3-carboxylate (6.12 g, 22.1 mmol) was dissolved in ethanol (30.0 ml), and the solution was mixed with potassium carbonate (3.68 g) and stirred at from 0° C. to room temperature for 14 hours. The solvent was evaporated under reduced pressure, and the thus obtained residue was mixed with water and ethyl acetate and extracted with ethyl acetate. The thus obtained organic layer was washed with water and saturated brine in that order and dried over anhydrous sodium sulfate. The solvent was evaporated under reduced pressure and the resulting residue was purified by a silica gel column chromatography (ether:hexane=1:1) to obtain the title compound (4.59 g, 93.9%) as white amorphous.

IR (KBr) $v_{max}$: 3168, 2944, 2908, 2836, 1724, 1566, 1454, 1432, 1270, 1248, 1236, 1186, 1172, 1148, 1086, 1060, 992 cm$^{-1}$. $^1$H-NMR (CDCl$_3$) δ: 1.75–2.38 (4 H, m), 2.73–2.89 (2 H, m), 2.78 (3 H, s), 3.90 (3 H, s), 4.62–4.72 (1 H, m), 7.93 (1 H, s).

REFERENCE EXAMPLE 45

Ethyl 9-methoxy-2-methyl-6,7,8,9-tetrahydro-5H-cyclohepta[b]pyridine-3-carboxylate In an atmosphere of argon, ethyl 9-hydroxy-2-methyl-6, 7,8,9-tetrahydro-5H-cyclohepta[b]pyridine-3-carboxylate (1.04 g, 4.16 mmol) was dissolved in anhydrous THF (8.0 ml), and the solution was mixed with sodium hydride (182.3 mg, 4.56 mmol) at 0° C. This was stirred at the same temperature for 1 hour, mixed with methyl iodide (0.33 ml, 4.76 mmol) by its dropwise addition and then stirred at room temperature for 1.5 hours. The reaction solution was mixed with water and extracted with ethyl acetate, and the thus obtained organic layer was washed with water and saturated brine in that order and dried over anhydrous magnesium sulfate. The solvent was evaporated under reduced pressure and the resulting residue was purified by a silica gel column chromatography (ether:hexane=1:1) to obtain the title compound (639.8 mg, 58.4%) as yellow oil.

IR (neat) $v_{max}$: 2980, 2928, 2856, 1724, 1596, 1560, 1444, 1412, 1262, 1204, 1136, 1114, 1092, 1072, 1052 cm$^{-1}$. $^1$H-NMR (CDCl$_3$) δ: 1.40 (3 H, t, J=7.0 Hz), 1.67–2.24 (4 H, m), 2.47–2.77 (2 H, m), 2.77 (3 H, s), 3.06–3.27 (2 H, m), 3.27 (3 H, s), 4.37 (2 H, q, J=7.0 Hz), 4.52 (1 H, d, J=6.8 Hz), 7.87 (1 H, s).

REFERENCE EXAMPLE 46

Ethyl 9-chloro-2-methyl-6,7,8,9-tetrahydro-5H-cyclohepta[b]pyridine-3-carboxylate Ethyl 9-hydroxy-2-methyl-6,7,8,9-tetrahydro-5H-cyclohepta[b]pyridine-3-carboxylate (3.92 g, 15.7mmol) was dissolved in chloroform (12.0 ml) to which was subsequently added dropwise thionyl chloride (4.4 ml) at −11° C. This was stirred at room temperature for 21 hours, and the reaction solution was poured into ice water, adjusted to pH 8 with 2 N sodium hydroxide aqueous solution and then extracted with chloroform. The thus obtained organic layer was washed with water and saturated brine in that order and dried over anhydrous sodium sulfate. The solvent was evaporated under reduced pressure and the resulting residue was purified by a silica gel column chromatography (ether:hexane=1:2) to obtain the title compound (3.35 g, 79.8%) as pale yellow oil.

IR (neat) $v_{max}$: 2980, 2932, 1720, 1440, 1310, 1264, 1230, 1206, 1138, 1108, 1066, 1050, 754, 712 cm$^{-1}$. $^1$H-NM (CDCl$_3$) δ: 1.39 (3 H, t, J=7.0 Hz), 1.81–2.41 (6 H, m), 2.75 (3 H, s), 3.06–3.42 (2 H, m), 4.37 (2 H, q, J=7.0 Hz), 5.41 (1 H, d, J=4.4 Hz), 7.92 (1 H, s).

REFERENCE EXAMPLE 47

Ethyl 8-chloro-2-methyl-5,6,7,8-tetrahydrocyclohexa[b]pyridine-3-carboxylate

In the same manner as described in Reference Example 46, the title compound (1.86 g, 94.0%) was obtained as pale yellow oil from ethyl 8-hydroxy-2-methyl-5,6,7,8-tetrahydrocyclohexa[b]pyridine-3-carboxylate (1.83 g, 7.78 mmol).

IR (neat) $v_{max}$: 2948, 1724, 1556, 1446, 1302, 1266, 1232, 1172, 1142, 1080, 1064, 652 cm$^{-1}$. $^1$H-NMR (CDCl$_3$) δ: 1.39 (3 H, t, J=7.0 Hz), 1.89–2.32 (4 H, m), 2.78 (3 H, s), 2.78–2.89 (2 H, m), 4.37 (2 H, q, J=7.0 Hz), 5.23 (1 H, br-s), 7.93 (1 H, s).

REFERENCE EXAMPLE 48

Methyl 9-chloro-2-methyl-6,7,8,9-tetrahydro-5H-cyclohepta[b]pyridine-3-carboxylate In the same manner as described in Reference Example 46, the title compound (3.00 g, 92.3%) was obtained as white powder from methyl 9-hydroxy-2-methyl-6,7,8,9-tetrahydro-5H-cyclohepta[b]pyridine-3-carboxylate (3.02 g, 12.8 mmol).

Melting point: 61° C. IR (KBr) $v_{max}$: 2932, 2856, 1730, 1558, 1436, 1310, 1266, 1224, 1208, 1140, 1108, 1068, 1052, 752, 628 cm$^{-1}$. $^1$H-NMR (CDCl$_3$) δ: 1.81–2.45 (3 H, m), 2.57 (3 H, s), 3.12–3.42 (2 H, m), 3.90 (3 H, s), 5.41 (1 H, d, J=4.8 Hz), 7.93 (1 H, s).

REFERENCE EXAMPLE 49

(3-Ethoxycarbonyl-2-methyl-6,7,8,9-tetrahydro-5H-cyclohepta[b]pyridin-9-yl)nitrate Ethyl 9-chloro-2-methyl-6,7,8,9-tetrahydro-5H-cyclohepta[b]pyridine-3-carboxylate (1.86 g, 6.95 mmol) was dissolved in acetonitrile (8.0 ml) and the solution was mixed with silver nitrate (2.11 g, 12.4 mmol) at 0° C. This was stirred at 50° C. for 6 days under shading. The reaction solution was diluted with ethyl acetate, the insoluble matter was removed by celite filtration, the resulting residue was washed with ethyl acetate, and then the solvent was evaporated under reduced pressure and the resulting residue was purified by a silica gel column chromatography (ether:hexane=1:1) to obtain the title compound (1.51 g, 73.9%) as pale yellow oil.

IR (neat) $v_{max}$: 2936, 1724, 1638, 1598, 1562, 1442, 1306, 1280, 1246, 1196, 1130, 1058, 1012, 1000, 866 cm$^{-1}$. $^1$H-NMR (CDCl$_3$) δ: 1.39 (3 H, t, J=7.3 Hz), 1.73–2.20 (6 H, m), 2.75 (3 H, s), 2.75–2.97 (2 H, m), 4.37 (2 H, q, J=7.3 Hz), 5.98–6.05 (1 H, m), 7.94 (1 H, s).

REFERENCE EXAMPLE 50

(3-Carboxy-2-methyl-6,7,8,9-tetrahydro-5H-cyclohepta[b]pyridin-9-yl) nitrate (3-Ethoxycarbonyl-2-methyl-6,7,8,9-tetrahydro-5H-cyclohepta[b]pyridin-9-yl) nitrate (1.51 g, 5.12 mmol) was dissolved in methanol (24.0 ml) to which was subsequently added dropwise 10% sodium hydroxide aqueous solution (6.0 ml) at 0° C. After 1.5 hours of stirring at room temperature, the solvent was evaporated and the thus obtained residue was washed with ethyl acetate, adjusted to pH 6 with 2 N hydrochloric acid and then extracted with chloroform:methanol (5:1). The thus obtained organic layer was washed with saturated brine and dried over anhydrous sodium sulfate. By evaporating the solvent under reduced pressure, the title compound (1.07 g, 78.5%) was obtained as pale yellow amorphous.

IR (KBr) $v_{max}$: 2936, 2860, 1706, 1636, 1598, 1560, 1442, 1368, 1306, 1280, 1194, 1142, 1000, 860, 792, 748, 698 cm$^{-1}$. $^1$H-NMR (CDCl$_3$) δ: 1.77–2.18 (6 H, m), 2.82 (3 H, s), 2.82–2.91 (2 H, m), 6.01–6.07 (1 H, br-s), 8.08 (1 H, s).

REFERENCE EXAMPLE 51

Ethyl 2-methyl-6,7-dihydro-5H-cyclohepta[b]pyridine-3-carboxylate

In an atmosphere of argon, ethyl 9-chloro-2-methyl-6,7,8,9-tetrahydro-5H-cyclohepta[b]pyridine-3-carboxylate (3.35 g, 12.5 mmol) was dissolved in toluene (12.0 ml), and the solution was mixed with 1,8-diazabicyclo[5.4.0]-7-undecene (DBU) (2.9 ml, 18.9 mmol) at 0° C. and then heated under reflux for 23 hours. The solvent was evaporated under reduced pressure, and the thus obtained residue was dissolved in ethyl acetate, mixed with water and then extracted with ethyl acetate. The thus obtained organic layer was washed with water and saturated brine in that order and dried over anhydrous sodium sulfate. The solvent was evaporated under reduced pressure and the resulting residue was purified by a silica gel column chromatography (ether:hexane=1:2) to obtain the title compound (2.82 g, 97.5%) as pale yellow oil.

IR (neat) $v_{max}$: 2980, 2928, 1722, 1592, 1552, 1446, 1416, 1254, 1204, 1140, 1058 cm$^{-1}$. $^1$H-NMR (CDCl$_3$) δ: 1.40 (3 H, t, J=7.0 Hz), 1.67–2.09 (3 H, m), 2.47–2.60 (1 H, m), 2.77 (3 H, s), 2.77–3.09 (2 H, m), 4.36 (2 H, q, J=7.0 Hz), 6.23 (1 H, dt, J=12.5, 4.4 Hz), 6.67 (1 H, d, J=12.5 Hz), 7.88 (1 H, s).

REFERENCE EXAMPLE 52

Methyl 2-methyl-6,7-dihydro-5H-cyclohepta[b]pyridine-3-carboxylate

In the same manner as described in Reference Example 51, the title compound (8.72 g, 67.9%) was obtained as fluorescent yellow oil from methyl 9-chloro-2-methyl-6,7,8,9-tetrahydro-5H-cyclohepta[b]pyridine-3-carboxylate (14.99 g, 59.1 mmol) and DBU (13.6 ml, 88.7 mmol).

IR (neat) $v_{max}$: 3024, 2932, 1726, 1592, 1552, 1434, 1382, 1268, 1210, 1140, 1062, 798 cm$^{-1}$. $^1$H-NMR (CDCl$_3$) δ: 1.85–2.09 (2 H, m), 2.33–2.60 (2 H, m), 2.77 (3 H, s), 2.77–2.87 (2 H, m), 3.90 (3 H, s), 6.24 (1 H, dt, J=12.5, 4.4 Hz), 6.67 (1 H, d, J=12.5 Hz), 7.89 (1 H, s).

REFERENCE EXAMPLE 53

Ethyl 2-methyl-5,6-dihydrocyclohexa[b]pyridine-3-carboxylate

In the same manner as described in Reference Example 51, the title compound (422.1 mg, 49 8%) was obtained as yellow oil from methyl 8-chloro-2-methyl-5,6,7,8-tetrahydrocyclohexa[b]pyridine-3-carboxylate (990.0 mg, 3.90 mmol) and DBU (0.66 ml, 4.30 mmol).

IR (neat) $v_{max}$: 2980, 2936, 1720, 1596, 1554, 1448, 1410, 1274, 1250, 1216, 1200, 1168, 1064 cm$^{-1}$. $^1$H-NMR (CDCl$_3$) δ: 1.40 (3 H, t, J=7.3 Hz), 2.28–2.48 (2 H, m), 2.77 (3 H, s), 2.86–2.99 (2 H, m), 4.36 (2 H, q, J=7.3 Hz), 6.42 (1 H, dt, J=10.3, 3.7 Hz), 6.66 (1 H, d, J=10.3 Hz), 7.88 (1 H, s).

REFERENCE EXAMPLE 54

Methyl 2-methyl-8-oxo-5,6,7,8-tetrahydrocyclohexa[b]pyridine-3-carboxylate

Methyl 8-hydroxy-2-methyl-5,6,7,8-tetrahydrocyclohexa[b]pyridine-3-carboxylate (3.95 g, 17.9 mmol) was dissolved in dichloromethane (80.0 ml), and the solution was mixed with activated manganese dioxide (23.29 g) and stirred at room temperature for 30 minutes. The reaction solution was diluted with ethyl acetate and then purified by a short column chromatography (ethyl acetate) and recrystallization (ethyl acetate-ether) to obtain the title compound (975.1 mg, 24.9%) as pale yellow needle crystals.

Melting point: 180–181° C. IR (KBr) $v_{max}$: 1724, 1698, 1548, 1444, 1428, 1400, 1286, 1270, 1232, 1196, 1184, 1058, 912, 900, 786, 582 cm$^{-1}$. $^1$H-NMR (CDCl$_3$) δ: 2.12–2.33 (2 H, m), 2.74–3.09 (4 H, m), 2.87 (3 H, s), 3.94 (3 H, s), 8.12 (1 H, s).

REFERENCE EXAMPLE 55

Methyl 2-methyl-9-oxo-6,7,8,9-tetrahydro-5H-cyclohepta[b]pyridine-3-carboxylate

In the same manner as described in Reference Example 54, the title compound (157.4 mg, 63.7%) was obtained as white powder from methyl 9-hydroxy-2-methyl-6,7,8,9-tetrahydro-5H-cyclohepta[b]pyridine-3-carboxylate (248.5 mg, 1.06 mmol).

Melting point: 58–61° C. IR (KBr) $v_{max}$: 2948, 2868, 1728, 1692, 1550, 1430, 1396, 1272, 1244, 1190, 1132, 1110, 1056, 1040, 894, 782 cm$^{-1}$. $^1$H-NMR (CDCl$_3$) δ: 1.86–1.93 (4 H, m), 2.72–2.90 (4 H, m), 2.85 (3 H, s), 3.94 (3 H, s), 8.06 (1 H, s).

REFERENCE EXAMPLE 56

Methyl 8-hydoroxyimino-2-methyl-5,6,7,8-tetrahydrocryclohexa[b]pyridine-3-carboxylate Methyl 2-methyl-8-oxo-5,6,7,8-tetrahydrocyclohexa[b]pyridine-3-carboxylate (570.3 mg, 2.60 mmol) was suspended in methanol (10.0 ml) and water (4.0 ml), and the suspension was mixed with hydroxyamine hydrochloride (206.1 mg) and potassium carbonate (434.5 mg, 3.13 mmol) and stirred at room temperature for 2 hours. The reaction solution was diluted with ethyl acetate, mixed with water and then extracted with ethyl acetate. The thus obtained organic layer was washed with saturated brine and dried over anhydrous sodium sulfate. The solvent was evaporated under reduced pressure and the thus formed crude crystals were recrystallized (ethyl acetate) to obtain the title compound (555.0 mg, 91.1%) as yellow powder.

Melting point: 195–197° C. (decomp.) IR (KBr) $v_{max}$: 3228, 2944, 1720, 1552, 1438, 1266, 1238, 1186, 1176, 1120, 1060, 1028, 1008, 962, 882, 800, 790 cm$^{-1}$. $^1$H-NMR (CDCl$_3$) δ: 1.69–2.05 (2 H, m), 2.75–3.04 (4 H, m), 2.84 (3 H, s), 3.91 (3 H, s), 8.00 (1 H, s), 9.43–9.63 (1 H, br-s).

REFERENCE EXAMPLE 57

Methyl 8-methoxyimino-2-methyl-5,6,7,8-tetrahydrocyclohexa[b]pyridine-3-carboxylate In an atmosphere of argon, methyl 8-hydroxyimino-2-methyl-5,6,7,8-tetrahydrocyclohexa[b]pyridine-3-carboxylate (1.01 g, 4.33 mmol) was suspended in a mixed solution of THF (5.0 ml) and dimethylformamide (DMF) (1.5 ml) at 0° C., and the suspension was mixed with sodium hydride (192.0 mg, 4.80 mmol) and stirred at room temperature for 1.5 hours. To this was added dropwise methyl iodide (192.0 mg, 4.80 mmol) at room temperature, followed by 2 hours of stirring. The reaction solution was diluted with ethyl acetate, mixed with water and then extracted with ethyl acetate. The thus obtained organic layer was washed with water and saturated brine in that order and dried over anhydrous sodium sulfate. The solvent was evaporated under reduced pressure and the resulting residue was purified by a silica gel column chromatography (ethyl acetate:hexane=1:3) to obtain the title compound (801.4 mg, 74.5%) as pale yellow powder.

Melting point: 124–125° C. IR (KBr) $v_{max}$: 2976, 2944, 2880, 1724, 1572, 1542, 1432, 1260, 1240, 1186, 1114, 1064, 1034, 992, 938, 870, 784 cm$^{-1}$. $^1$H-NMR (CDCl$_3$) δ: 1.80–2.00 (2 H, m), 2.71–2.92 (4 H, m), 2.86 (3 H, s), 3.91 (3 H, s), 4.14 (3 H, s), 7.99 (1 H, s).

REFERENCE EXAMPLE 58

Ethyl 9-hydoroxymethyl-2-methyl-6,7,8,9-tetrahydro-5H-cyclohepta[b]pyridine-3-carboxylate Ethyl 2-methyl-6,7,8,9-tetrahydro-5H-cyclohepta[b]pyridine-3-carboxylate (11.90 g, 48.2 mmol) and 80% p-formaldehyde (9.18 g) were sealed in a tube and heated at 12.0° C. for 48 hours. After cooling, the reaction solution was mixed with 16% hydrochloric acid, washed with ether, adjusted to pH 9 to 10 with 40% sodium hydroxide aqueous solution while cooling in an ice bath and then extracted with ethyl acetate. The organic layer was washed with water and saturated brine and dried over anhydrous sodium sulfate. The solvent was evaporated under reduced pressure and the resulting residue was purified by a silica gel column chromatography (ether:hexane=1:5–1:1) to obtain the title compound (3.34 g, 26.3%) as white powder.

Melting point: 47–48° C. IR (KBr) $v_{max}$: 3456, 2976, 2924, 1726, 1596, 1558, 1442, 1366, 1248, 1186, 1128, 1096, 1052 cm$^{-1}$. $^1$H-NMR (CDCl$_3$) δ: 1.40 (3 H, t, J=7.0Hz), 1.50–2.20 (4 H, m), 2.70–2.90 (2 H, m), 2.78 (3 H, s), 2.97–3.27 (1 H, m), 3.99 (2 H, d, J=5.5 Hz), 4.37 (2 H, q, J=7.0 Hz), 7.92 (1 H, s).

REFERENCE EXAMPLE 59

Ethyl 9-(E)-benzylidene-2-methyl-6,7,8,9-tetrahydro-5H-cyclohepta[b]pyridine-3-carboxylate Ethyl 2-methyl-6,7,8,9-tetrahydro-5H-cyclohepta[b]pyridine-3-carboxylate (1.07 g, 4.40 mmol) and benzaldehyde (583.6 mg, 5.50 mmol) were dissolved in acetic anhydride (2.0 ml), and the solution was mixed with zinc chloride (40.0 mg, 0.30 mmol) at room temperature and then heated under reflux for 36 hours. After cooling, acetic anhydride was evaporated under reduced pressure, and the thus obtained residue was mixed with water and extracted with ethyl acetate. The organic layer was washed with water and saturated brine and dried over anhydrous sodium sulfate and then the solvent was evaporated under reduced pressure and the resulting residue was purified by a silica gel column chromatography (ether:hexane=1:6–1:5) to obtain the title compound (471.4 mg, 33.4%) as pale yellow oil.

IR (neat) $v_{max}$: 3032, 2932, 1760, 1722, 1588, 1494, 1408, 1312, 1200, 1094, 1046, 970 cm$^{-1}$. $^1$H-NMR (CDCl$_3$) δ: 1.41 (3 H, t, J=7.0 Hz), 1.75–2.00 (4 H, m), 2.12 (4 H, s), 2.63–3.00 (2 H, m), 2.86 (3 H, s), 4.38 (2 H, q, J=7.0 Hz), 7.20–7.65 (5 H, m), 7.68 (1 H, s), 7.93 (1 H, s).

REFERENCE EXAMPLE 60

Ethyl 9-bromomethyl-2-methyl-6,7,8,9-tetrahydro-5H-cyclohepta[b]pyridine-3-carboxylate In an atmosphere of argon, ethyl 9-hydroxymethyl-2-methyl-6,7,8,9-tetrahydro-5H-cyclohepta[b]pyridine-3-carboxylate (263.0 mg, 1.00 mmol) was dissolved in methylene chloride (5.0 ml), the solution was mixed with triphenylphosphine (393.0 mg, 1.50 mmol) at 0° C. and then with carbon tetrabromide (663.3 mg, 2.00 mmol) and the mixture was stirred at room temperature for 3 hours. The reaction solution was mixed with saturated sodium bicarbonate aqueous solution and water and extracted with ethyl acetate, and the resulting organic layer was washed with water and saturated brine. After drying with anhydrous sodium sulfate, the solvent was evaporated under reduced pressure and the resulting residue was purified by a silica gel column chromatography (ether:hexane=1:5) to obtain the title compound (349.1 mg, quantitative) as white powder.

Melting point: 50–51° C. IR (KBr) $v_{max}$: 2976, 2928, 2852, 1720, 1596, 1536, 1454, 1408, 1366, 1278, 1228, 1168, 1096, 1053, 786 cm$^{-1}$. $^1$H-NMR (CDCl$_3$) δ: 1.39 (3 H, t, J=7.0Hz), 1.62–2.33 (6 H, m), 2.60–2.90 (2 H, m), 2.78 (3 H, s), 3.20–3.50 (1 H, m), 3.71 (1 H, dd, J=each 9.1 Hz), 4.05–4.26 (1 H, m), 4.36 (2 H, q, J=7.0 Hz), 7.86 (1 H, s).

REFERENCE EXAMPLE 61

(3-Ethoxycarbonyl-2-methyl-6,7,8,9-tetrahydro-5H-cyclohepta[b]pyridin-9-yl)methyl nitrate In an atmosphere of argon, the title compound (244.4 mg, 84.0%) was obtained as white powder from ethyl 9-bromomethyl-2-methyl-6,7,8,9-tetrahydro-5H-cycloheptat[b]pyridine-3-carboxylate (305.0 mg, 1.00 mmol) in the same manner as described in Reference Example 49.

Melting point: 88–89° C. IR (KBr) $v_{max}$: 2984, 2856, 1712, 1620, 1596, 1556, 1436, 1382, 1334, 1302, 1248, 1194, 1044, 992 cm$^{-1}$. $^1$H-NMR (CDCl$_3$) δ: 1.39 (3 H, t, J=7.0 Hz), 1.73–2.16 (6 H, m), 2.56–2.90 (2 H, m), 2.73 (3 H, s), 3.10–3.50 (1 H, m), 4.36 (2 H, q, J=7.0 Hz), 4.73 (1 H, dd, J=11.0, 2.6 Hz), 5.31 (1 H, dd, J=11.0, 5.3 Hz), 7.88 (1 H, s).

REFERENCE EXAMPLE 62

(3-Carboxy-2-methyl-6,7,8,9-tetrahydro-5H-cyclohepta[b]pyridin-9-yl)methyl nitrate In the same manner as described in Reference Example 50, the title compound (321.0 mg, 99.7%) was obtained as white powder from (3-ethoxycarbonyl-2-methyl-6,7,8,9-tetrahydro-5H-cyclohepta[b]pyridin-9-yl)methyl nitrate (354.0 mg, 1.22 mmol).

Melting point: 157–159° C. IR (Br) $v_{max}$: 2932, 2854, 2800, 1728, 1641, 1602, 1434, 1368, 1254, 1215, 945 cm$^{-1}$. $^1$H-NMR (CDCl$_3$) δ: 1.70–2.30 (6 H, m), 2.95–3.10 (1 H, m), 3.18 (3 H, s), 3.25–3.50 (2 H, m), 4.94 (2 H, d, J=5.9 Hz), 8.59 (1 H, s).

REFERENCE EXAMPLE 63

Ethyl 2-chloromethyl-6,7,8,9-tetrahydro-5H-cyclohepta[b]pyridine-3-carboxylate 6,7,8,9-Tetrahydro-5H-cyclohepta[b]pyrido[3,2-c]furan-3-one (5.01 g, 24.7 mmol) was dissolved in ethanol (25.0.0 ml), hydrogen chloride gas was bubbled into the solution at 0° C. for 22 hours and then the resulting solution was stirred at room temperature for 22 hours. The reaction solution was poured into ice water, neutralized by adding 40% sodium hydroxide aqueous solution at 0° C. and then extracted with chloroform. The thus obtained organic layer was washed with water and saturated brine in that order and dried over anhydrous sodium sulfate. The solvent was evaporated under reduced pressure and the resulting residue was purified by a silica gel column chromatography (ethyl acetate:hexane=1:3) to obtain the title compound (5.09 g, 77.1%) as white powder.

Melting point: 81–82° C. IR (KBr) $v_{max}$: 2916, 2848, 1708, 1594, 1454, 1440, 1412, 1290, 1280, 1260, 1240, 1204, 1188, 1154, 1092, 1052, 952, 720, 712 cm$^{-1}$. $^1$H-NMR (CDCl$_3$) δ: 1.42 (3 H, t, J=7.0 Hz), 1.69–1.95 (6 H, m), 2.78–2.88 (2 H, m), 3.03–3.14 (2 H, m), 4.40 (2 H, q, J=7.0 Hz), 5.05 (2 H, s), 7.94 (1 H, s).

REFERENCE EXAMPLE 64

Ethyl 2-(3-pyridylmethyloxymethyl)-6,7,8,9-tetrahydro-5H-cyclohepta[b]pyridine-3-carboxylate In an atmosphere of argon, 3-pyridinemethanol (0.41 ml, 4.20 mmol) was dissolved in anhydrous THF (4.0 ml), and the solution was mixed with sodium hydride (173.6 mg, 4.34 mmol) at 0° C. and stirred at the same temperature for 1 hour. To this was added dropwise THF solution (4.0 ml) of ethyl 2-chloromethyl-6,7,8,9-tetrahydro-5H-cyclohepta[b]pyridine-3-carboxylate (1.07 g, 3.98 mmol) at 0° C., and the mixture was stirred at from 0° C. to room temperature for 20 hours. The reaction solution was diluted with ethyl acetate, mixed with water and then extracted with ethyl acetate. Thethus obtainedorganiclayer was washed with water and saturated brine in that order and dried over anhydrous sodium sulfate. The solvent was evaporated under reduced pressure and the resulting residue was purified by a silica gel column chromatography (ethyl acetate:hexane=1:3—chloroform:methanol=40:1) to obtain the title compound (287.8 mg, 20.1%) as yellow oil.

IR (neat) $v_{max}$: 2980, 2924, 2852, 1726, 1594, 1578, 1564, 1454, 1444, 1428, 1368, 1280, 1200, 1146, 1116, 1052 cm$^{-1}$. $^1$H-NMR (CDCl$_3$) δ: 1.35 (3 H, t, J=7.0 Hz), 1.59–2.00 (6 H, m), 2.76–2.86 (2 H, m), 3.04–3.14 (2 H, m), 4.33 (2 H, q, J=7.0 Hz), 4.64 (2 H, s), 4.98 (2 H, s), 7.16–7.30 (1 H, m), 7.67–7.85 (1 H, m), 7.85 (1 H, s), 8.48–8.59 (2 H, m).

REFERENCE EXAMPLE 65

Ethyl 2-(4-formylphenoxymethyl)-6,7,8,9-tetrahydro-5H-cyclohepta[b]pyridine-3-carboxylate Ethyl 2-chloromethyl-6,7,8,9-tetrahydro-5H-cyclohexa[b]pyridine-3-carboxylate (2.30 g, 8.60 mmol) was suspended in DMF, and the suspension was mixed with 4-hydroxybenzaldehyde (1.08 g, 8.64 mmol) and potassium carbonate (2.63 g, 18.9 mmol) and stirred at room temperature for 22 hours The solvent was evaporated under reduced pressure, and the thus obtained residue was dissolved in ethyl acetate, mixed with water and then extracted with ethyl acetate. The thus obtained organic layer was washed with water and saturated brine in that order and dried over anhydrous sodium sulfate. The solvent was evaporated under reduced pressure and the resulting residue was purified by a silica gel column chromatography (ethyl acetate:hexane=1:3) to obtain the title compound (3.06 g, quantitative) as white powder.

Melting point: 83–84° C. IR (KBr) $v_{max}$: 2932, 1720, 1696, 1602, 1578, 1560, 1454, 1298, 1278, 1262, 1244, 1228, 1146, 1118, 1056, 1016, 866, 832, 782 cm$^{-1}$. $^1$H-NMR (CDCl$_3$) δ: 1.28 (3 H, t, J=7.0 Hz), 1.64–1.90 (6 H, m), 2.79–2.90 (2 H, m), 3.03–3.14 (2 H, m), 4.32 (2 H, q, J=7.0 Hz), 5.54 (2 H, s), 7.08 (2 H, d, J=8.8 Hz), 7.82 (2 H, J=8.8 Hz), 7.95 (1 H, s), 9.88 (1 H, s).

REFERENCE EXAMPLE 66

Ethyl 2-(4-carboxyphenoxymethyl)-6,7,8,9-tetrahydro-5H-cyclohepta[b]pyridine-3-carboxylate Ethyl 2-(4-formylphenoxymethyl)-6,7,8,9-tetrahydro-5H-cyclohepta[b]pyridine-3-carboxylate (3.05 g, 8.63 mmol) was dissolved in a mixed solution of 2-methyl-2-propanol (33.0 ml) and 2-methyl-2-butene (10.0 ml), and to the solution was added dropwise aqueous solution (26.0 ml) of sodium chlorite (80%, 4.88 g, 43.2 mmol) and sodium dihydrogenphosphate dihydrate (4.46 g, 28.6 mmol). Chloroform was added until insoluble matter was dissolved and then the solution was stirred at room temperature for 3.5 hours. The reaction solution was diluted with chloroform, mixed with water and then extracted with chloroform-methanol mixed solution (5:1). The thus obtained organic layer was washed with saturated brine and dried over anhydrous sodium sulfate. The solvent was evaporated under reduced pressure and the resulting residue was purified by a silica gel column chromatography (chloroform:methanol=10:1) to obtain the title compound (2.84 g, 89.1%) as white powder.

Melting point: 135–136° C. IR (KBr) $v_{max}$: 2920, 1708, 1680, 1604, 1578, 1454, 1428, 1376, 1320, 1264, 1246, 1222, 1200, 1172, 1148, 1054, 1002, 774 cm$^{-1}$. $^1$H-NMR (CDCl$_3$) δ: 1.27 (3 H, t, J=7.0 Hz), 1.69–1.93 (6 H, m), 2.79–2.89 (2 H, m), 3.04–3.14 (2 H, m), 4.31 (2 H, q, J=7.0 Hz), 5.52 (2 H, s), 7.01 (2 H, d, J=8.8 Hz), 7.95 (1 H, s), 7.03 (2 H, d, J=8.8 Hz).

REFERENCE EXAMPLE 67

Ethyl 2-{4-[2-(N,N-dimethylamino)ethylaminocarbonyl]phenoxymethyl}-6,7,8,9-tetrahydro-5H-cyclohepta[b]pyridine-3-carboxylate In an atmosphere of argon, ethyl 2-(4-carboxyphenoxymethyl)-6,7,8,9-tetrahydro-5H-cyclohepta[b]pyridine-3-carboxylate (1.22 g, 3.31 mmol) was dissolved in methylene chloride (5.0 ml), and the solution was mixed with N,N-dimethylethylenediamine hydrochloride (0.44 ml, 4.01 mmol) and 1-ethyl-3-(3-dimethylaminopropyl)carbodiimide (EDC) hydrochloride (954.2 mg, 4.98 mmol) at 0° C. and then stirred at room temperature for 15 hours. The reaction solution was diluted with chloroform, mixed with saturated sodium bicarbonate aqueous solution and then extracted with chloroform. The thus obtained organic layer was washed with water and saturated brine in that order and dried over anhydrous sodium sulfate. The solvent was evaporated under reduced pressure and the resulting residue was purified by a silica gel column chromatography (chloroform:methanol=10:1) to obtain the title compound (767.2 mg, 52.7%) as pale yellow amorphous.

IR (KBr) $v_{max}$: 3348, 2928, 2852, 2820, 2776, 1724, 1642, 1606, 1548, 1504, 1456, 1376, 1268, 1200, 1148, 1056 cm$^{-1}$. $^1$H-NMR (CDCl$_3$) δ: 1.26 (3 H, t, J=7.0 Hz), 1.68–1.79 (6 H, m), 2.27 (6 H, s), 2.50 (2 H, t, J=5.7 Hz), 2.78–2.89 (2 H, m), 3.03–3.14 (2 H, m), 3.41–3.59 (2 H, m), 4.30 (2 H, q, J=7.0 Hz), 5.47 (2 H, s), 6.62–6.68 (1 H, br-s), 6.98 (2 H, d, J=8.8 Hz), 7.73 (2 H, d, J=8.8 Hz), 7.92 (1 H, s).

REFERENCE EXAMPLE 68

Ethyl 2-(N,N-dimethylaminomethyl)-6,7,8,9-tetrahydro-5H-cyclohepta[b]pyridine-3-carboxylate In an atmosphere of argon, ethyl 2-chgloromethyl-6,7,8,9-tetrahydro-5H-cyclohepta[b]pyridine-3-carboxylate (614.3 mg, 2.29 mmol) was dissolved in dioxane (6.0 ml), and the solution was mixed with 80% dimethylamine aqueous solution (12.0 ml) at 0° C. and then stirred at room temperature for 1 hour. The solvent was evaporated under reduced pressure and the resulting residue was purified by a silica gel columnchromatography (chloroform:methanol=5:1) to obtain the title compound (567.3 mg, 89.6%) as white powder.

Melting point: 179–180° C. IR (KBr) $v_{max}$: 2976, 2928, 2852, 2816, 2772, 1718, 1596, 1454, 1436, 1416, 1342, 1282, 1270, 1242, 1200, 1162, 1146, 1054 cm$^{-1}$. $^1$H-NMR (CDCl$_3$) δ: 1.41 (3 H, t, J=7.0 Hz), 1.68–1.90 (6 H, m), 2.68 (6 H, s), 2.78–2.88 (2 H, m), 3.07–3.18 (2 H, m), 4.35 (2 H, s), 4.39 (2 H, q, J=7.0 Hz), 7.91 (1 H, s).

REFERENCE EXAMPLE 69

Ethyl 2-methyl-5-oxo-6,7,8,9-tetrahydro-5H-cyclohepta[b]pyridine-3-carboxylate

Ethyl methyl-6,7,8,9-tetrahydro-5H-cyclohepta[b]pyridine-3-carboxylate (2.50 g, 10.1 mmol) was dissolved in acetic acid (7.0 ml), the solution was mixed with concentrated sulfuric acid (1.4 ml), and then 11% acetic acid aqueous solution (4.8 ml) of chromic anhydride (1.41 g, 14.1 mmol) was added thereto at 10 to 15° C. spending about 1 hour. After 6 hours of stirring at room temperature, water was added to the reaction solution to which was subsequently added dropwise 2-propanol at 0° C. to decompose excess chromic acid. The solvent was evaporated under reduced pressure, the thus obtained residue was neutralized with 20% sodium hydroxide aqueous solution at 0° C. and mixed with chloroform, and then the insoluble matter was removed by celite filtration and washed with chloroform. The resulting filtrate was extracted with chloroform, washed with water and saturated brine in that order and then dried over anhydrous sodium sulfate. The solvent was evaporated under reduced pressure and the resulting residue was purified by a silica gel column chromatography (ether:hexane=1:1) to obtain the title compound (284.7 mg, 10.8%) as colorless oil.

IR (neat) $v_{max}$: 2940, 2868, 1728, 1682, 1588, 1454, 1390, 1342, 1234, 1160, 1096 cm$^{-1}$. $^1$H-NMR (CDCl$_3$) δ: 1.40 (3 H, t, J=7.3 Hz), 1.70–2.20 (4 H, m), 2.85 (3 H, s), 2.70–3.00 (2 H, m), 3.19 (2 H, t, J=5.9 Hz), 4.38 (2 H, q, J=7.3 Hz), 8.25 (1 H, s).

REFERENCE EXAMPLE 70

Ethyl 5-hydroxy-2-methyl-6,7,8,9-tetrahydro-5H-cyclohepta[b]pyridine-3-carboxylate In an atmosphere of argon, ethyl 2-methyl-5-oxo-6,7,8,9-tetrahydro-5H-cyclohepta[b]pyridine-3-carboxylate (400.0 mg, 1.62 mmol) was dissolved in methanol (5.0 ml), and the solution was mixed with sodium borohydride (91.9 mg, 2.43 mmol) at 0° C. and stirred at the same temperature for 1 hour. Acetone was added dropwise to the reaction solution at 0° C. to decompose excess sodium borohydride and then the thus treated reaction solution was mixed with saturated ammonium chloride aqueous solution, extracted with ethyl acetate and washed with water and saturated brine. After drying with anhydrous sodium sulfate, the solvent was evaporated under reduced pressure and the resulting residue was purified by a silica gel column chromatography (ether:hexane=2:1) to obtain the title compound (387.7 mg, 96.1%) as colorless oil.

IR (neat) $v_{max}$: 3524, 3436, 3160, 2924, 2856, 1722, 1594, 1568, 1440, 1342, 1282, 1242, 1128, 1096 cm$^{-1}$. $^1$H-NMR (CDCl$_3$) δ: 1.39 (3 H, t, J=7.0 Hz), 1.63–2.25 (6 H, m), 2.78 (3 H, s), 2.80–3.35 (2 H, m), 4.37 (2 H, q, J=7.0 Hz), 4.70–5.00 (1 H, m), 8.24 (1 H, s).

REFERENCE EXAMPLE 71

Ethyl 5-tert-butyldimethylsilyloxy-2-methyl-6,7,8,9-tptrahydro-5H-cyclohepta[b]pyridine-3-carboxylate In an atmosphere of argon, ethyl 5-hydroxy-2-methyl-6,7,8,9-tetrahydro-5H-cyclohepta[b]pyridine-3-carboxylate (291.0 mg, 1.10 mmol) was dissolved in methylene chloride (10.0 ml) to which were subsequently added dropwise 2,6-lutidine (0.82 ml, 7.02 mmol) and tert-butyldimethylsilyl trifluoromethanesulfonate (0.54 ml, 2.34 mmol) in that order at 0° C., and the resulting mixture was stirred at the same temperature for 1 hour. The reaction solution was mixed with saturated sodium bicarbonate aqueous solution and water at 0° C., extracted with ethyl acetate and then washed with water and saturated brine in that order. After drying with anhydrous sodium sulfate, the solvent was evaporated under reduced pressure and the resulting residue was purified by a silica gel column chromatography (ether:hexane=1:3) to obtain the title compound (284.9 mg, 92.8%) as colorless oil.

IR (neat) $v_{max}$: 2932, 2856, 1722, 1596, 1560, 1440, 1406, 1372, 1280, 1204, 1180, 1006, 836 cm$^{-1}$. $^1$H-NMR (CDCl$_3$) δ: 0.77 (6 H, s), 0.93 (9 H, s), 1.42 (3 H, t, J=7.0 Hz), 1.60–2.15 (6 H, m), 2.76 (3 H, s), 2.80–3.30 (2 H, m), 4.40 (2 H, q, J=7.0 Hz), 4.70–4.90 (1 H, m), 8.22 (1 H, s).

REFERENCE EXAMPLE 72

5-tert-Butyldimethylsilyloxy-2-methyl-6,7,8,9-tetrahydro-5H-cyclohepta[b]pyridine-3-carboxylic acid In the same manner as described in Reference Example 50, the title compound (272.3 mg, 85.4%) was obtained as colorless amorphous from ethyl 5-tert-butyldimethylsilyloxy-2-methyl-6,7,8,9-tetrahydro-5H-cyclohepta[b]pyridine-3-carboxylate (380.0 mg, 1.00 mmol).

IR (KBr) $v_{max}$: 2932, 2860, 1716, 1598, 1472, 1446, 1254, 1146, 1020, 886 cm$^{-1}$. $^1$H-NMR (CDCl$_3$) δ: 0.09 (6 H, s), 0.92 (9 H, 5), 1.40–2.15 (6 H, m), 2.87 (3 H, s), 2.90–3.40 (2 H, m), 4.65–4.90 (1 H, m), 8.39 (1 H, s).

REFERENCE EXAMPLE 73

Ethyl 5-chloro-2-methyl-6,7,8,9-tetrahydro-5H-cyclohepta[b]pyridine-3-carboxylate In the same manner as described in Reference Example 46, the title compound (356.2 mg, 97.2%) was obtained as colorless oil from ethyl 5-hydroxy-2-methyl-6,7,8,9-tetrahydro-5H-cyclohepta[b]pyridine-3-carboxylate (340.0 mg, 1.37 mmol).

IR (neat) $v_{max}$: 2980, 2932, 1724, 1598, 1412, 1366, 1284, 1232, 1170, 1118, 1068, 850 cm$^{-1}$. $^1$H-NMR (CDCl$_3$) δ: 1.40 (3 H, t, J=7.3 Hz), 1.65–2.50 (6 H, m), 2.79 (3 H, s), 2.90–3.56 (2 H, m), 4.37 (2 H, q, J=7.3 Hz), 5.24 (1 H, br-d, J=5.5 Hz), 8.08 (1 H, s).

REFERENCE EXAMPLE 74

5-Chloro-2-methyl-6,7,8,9-tetrahydro-5H-cyclohepta[b]pyridine-3-carboxylic acid

In the same manner as described in Reference Example 50, the title compound (217.3 mg, quantitative) was obtained as colorless oil from ethyl 5-chloro-2-methyl-6,7,8,9-tetrahydro-5H-cyclohepta[b]pyridine-3-carboxylate (1.83 g, 7.78 mmol).

IR (neat) $v_{max}$: 2936, 2860, 1710, 1596, 1560, 1446, 1374, 1212, 1145, 1106, 1044 cm$^{-1}$. $^1$H-NMR (CDCl$_3$) δ: 1.50–2.60 (6 H, m), 2.86 (3 H, s), 3.00–3.60 (2 H, m), 5.26 (1 H, br-d, J=4.6 Hz), 6.50–6.90 (1 H, m), 8.23 (1 H, s).

REFERENCE EXAMPLE 75

Ethyl 2-methyl-8,9-dihydro-7H-cyclohepta[b]pyridine-3-carboxylate

In the same manner as described in Reference Example 51, the title compound (525.7 mg, 88.5%) was obtained as colorless oil from ethyl 5-chloro-2-methyl-6,7,8,9-tetrahydro-5H-cyclohepta[b]pyridine-3-carboxylate (687.0 mg, 2.57 mmol).

IR (neat) $v_{max}$: 2980, 2932, 1722, 1590, 1550, 1448, 1390, 1320, 1272, 1204, 1136, 1060 cm$^{-1}$. $^1$H-NMR (CDCl$_3$) δ: 1.39(3 H, t, J=7.0 Hz), 1.80–2.16 (2 H, m), 2.30–2.62 (2 H, m), 2.76 (3 H, s), 2.93–3.20 (2 H, m), 4.37 (2 H, q, J=7.0 Hz), 6.00 (1 H, ddd, J=12.0, 5.1, 5.1 Hz), 7.93 (1 H, s).

REFERENCE EXAMPLE 76

Ethyl 2-methyl-9-exomethylene-6,7,8,9-tetrahydro-5H-cyclohepta[b]pyridine-3-carboxylate In the same manner as described in Reference Example 51, the title compound (245.0 mg, quantitative) was obtained as colorless oil from ethyl 9-bromomethyl-2-methyl-6,7,8,9-tetrahydro-5H-cyclohepta[b]pyridine-3-carboxylate (263.0 mg, 1.00 mmol).

IR (neat) $v_{max}$: 2980, 2932, 2856, 1720, 1590, 1544, 1444, 1366, 1300, 1288, 1216, 1142, 1094, 1048, 910 cm$^{-1}$. $^1$H-NMR (CDCl$_3$) δ: 1.40 (3 H, t, J=7.0 Hz), 1.60–2.00 (4 H, m), 2.35–2.60 (2 H, m), 2.79 (3 H, s), 4.37 (2 H, q, J=7.0 Hz), 5.33 (1 H, br-s), 5.43 (1 H, d, J=1.98 Hz), 7.90 (1 H, s).

REFERENCE EXAMPLE 77

Ethyl 2-methyl-9-(E)-(3-pyridylmethylene)-6,7,8,9-tetrahydro-5H-cyclohepta[b]pyridine-3-carboxylate In the same manner as described in Reference Example 59, the title compound (516.2 mg, 39.5%) was obtained as pale yellow powder from ethyl 2-methyl-6,7,8,9-tetrahydro-5H-cyclohepta[b]pyridine-3-carboxylate (1.0 g, 4.04 mmol).

Melting point: 84–86° C. IR (KBr) $v_{max}$: 2980, 2936, 2860, 1720, 1590, 1544, 1442, 1368, 1262, 1190, 1094, 1024, 786 cm$^{-1}$. $^1$H-NMR (CDCl$_3$) δ: 1.42 (3 H, t, J=7.0 Hz), 1.50–2.00 (4 H, m), 4.50–2.95 (4 H, m), 2.85 (3 H, s), 4.39 (2 H, q, J=7.0 Hz), 7.08 (1 H, s), 7.27 (1 H, dd, J=8.1 Hz), 7.78 (1 H, d, J=8.1 Hz), 8.50 (1 H, d, J=4.2 Hz), 8.74 (1 H, s).

REFERENCE EXAMPLE 78

Ethyl 2-methyl-9-(3-pyridylmethyl)-6,7,8,9-tetrahydro-5H-cyclohepta[b]pyridine-3-carboxylate In the same manner as described in Reference Example 30, the title compound (504.8 mg, quantitative) was obtained as yellow oil from ethyl 2-methyl-9(E)-(3-pyridylmethyl)-6,7,8,9-tetrahydro-5H-cyclohepta[b]pyridine-3-carboxylate (500.0 mg, 1.54 mmol).

IR (neat) $v_{max}$: 2980, 2928, 2852, 1724, 1596, 11574, 1556, 1454, 1368, 1248, 1170, 1076, 1026, 752 cm$^{-1}$. $^1$H-NMR (CDCl$_3$) δ: 1.39 (3 H, t, J=7.0 Hz), 1.60–2.10 (6 H, m), 2.50–3.05 (2 H, m), 2.76 (3 H, s), 4.35 (2 H, q, J=7.0 Hz), 7.05–7.30 (1 H, m), 7.59 (1 H, d, J=7.7 Hz), 7.84 (1 H, s), 8.38 (1 H, dd, J=3.3, 1.5 Hz), 8.53 (1 H, d, J=1.5 Hz).

REFERENCE EXAMPLE 79

Ethyl 9-(4-formylphenoxymethyl)-2-methyl-6,7,8,9-tetrahydro-5H-cyclohepta[b]pyridine-3-carboxylate In an atmosphere of argon, ethyl 9-hydroxymethyl-2-methyl-6,7,8,9-tetrahydro-γ-cyclohepta[b]pyridine-3-carboxylate (263 mg, 1.00 mmol) and p-hydroxybenzaldehyde (183.3 mg, 1.50 mmol) were dissolved in THF (8.0 ml), the solution was mixed with triphenylphosphine (393.4 mg, 1.50 mmol) and then with diethyl azodicarboxylate (0.24 ml, 1.50 mmol) by its dropwise addition both at 0° C., and the resulting mixture was stirred at room temperature for 3 hours. The reaction solution was mixed with water, extracted with ethyl acetate and then washed with water and saturated brine in that order. After drying with anhydrous sodium sulfate, the solvent was evaporated under reduced pressure and the resulting residue was purified by a silica gel column chromatography (ether:hexane=1:3) to obtain the title compound (191.1 mg, 52.1%) as white powder.

Melting point: 145–146° C. IR (Br) $v_{max}$: 2920, 1726, 1694, 1606, 1580, 1446, 1270, 1218, 1168, 1132, 1046, 826 cm$^{-1}$. $^1$H-NMR (CDCl$_3$) δ: 1.40 (3 H, t, J=7.3 Hz), 1.70–2.38 (6 H, m), 2.58–2.96 (2 H, m), 2.73 (3 H, s), 3.30–3.70 (1 H, m), 4.30–4.50 (1 H, m), 4.39 (2 H, q, J=7.3 Hz), 4.76 (1 H, dd, J=9.9, 4.8 Hz), 7.10 (2 H, d, J=8.6 Hz), 7.53 (2 H, d, J=8.6 Hz), 7.90 (1 H, s), 9.90 (1 H, s).

REFERENCE EXAMPLE 80

Ethyl 9-(4-carboxyphenoxymethyl)-2-methyl-6,7,8,9-tetrahydro-5H-cyclohepta[b]pyridine-3-carboxylate In the same manner as described in Reference Example 66, the title compound (352.3 mg, 92. 0%) was obtained as colorless powder from ethyl 9-(4-formylphenoxymethyl)-2-methyl-6,7,8,9-tetrahydro-5H-cyclohepta[b]pyridine-3-carboxylate (367.0 mg, 1.00 mmol).

Melting point: 211–212° C. IR (KBr) $v_{max}$: 2976, 2856, 1720, 1680, 1606, 1580, 1514, 1400, 1330, 1294, 1252, 1180, 1144, 1048, 942 cm$^{-1}$. $^1$H-NMR (CDCl$_3$) δ: 1.40 (3 H, t, J=7.3 Hz), 1.70–2.20 (6 H, m), 2.60–3.00 (2 H, m), 2.74 (3 H, s), 3.30–3.63 (1 H, m), 4.15–4.50 (1 H, m), 4.45 (2 H, q, J=7.3 Hz), 4.73 (1 H, dd, J=9.9, 5.1 Hz), 7.02 (1 H, d, J=8.8 Hz), 7.89 (1 H, s), 8.02 (2 H, d, J=8.8 Hz).

REFERENCE EXAMPLE 81

Ethyl 2-methyl-9-{4-[2-(N,N-dimethylamino) ethylaminocarbonyl]phenoxymethyl}-6,7,8,9-tetrahydro-5H-cyclohepta[b]pyridine-3-carboxylate In the same manner as described in Reference Example 67, the title compound (354.0 mg, 85.9%) was obtained as colorless powder from ethyl 9-(4-carboxyphenoxymethyl)-2-methyl-6,7,8,9-tetrahydro-5H-cyclohepta[b]pyridine-3-carboxylate (350.0 mg, 0.91 mmol).

Melting point: 125–127° C. IR (KBr) $v_{max}$: 3276, 1506, 1454, 1334, 1278, 1220, 1176, 1142, 1080, 1046, 1010 cm$^{-1}$. $^1$H-NMR (CDCl$_3$) δ: 1.39 (3 H, t, J=7.0 Hz), 1.80–2.35 (6 H, m), 2.27 (6 H, s), 2.51 (2 H, t, J=6.2 Hz), 2.60–2.93 (2 H, m), 2.73 (3 H, s), 3.26–3.65 (3 H, m), 4.10–4.50 (1 H, m), 4.36 (2 H, q, J=7.0 Hz), 4.72 (1 H, dd, J=9.6, 4.6 Hz), 7.01 (1 H, d, J=8.8 Hz), 7.77 (2 H, d, J=8.8 Hz), 7.88 (1 H, s).

REFERENCE EXAMPLE 82

3-Hydroxymethyl-2-methyl-6,7,8,9-tetrahydro-5H-cyclohepta[b]pyridine

In an atmosphere of argon, ethyl 2-methyl-6,7,8,9-tetrahydro-5H-cyclohepta[b]pyridine-3-carboxylate (586.6 mg, 2.51 mmol) was dissolved in anhydrous THF (5.0 ml), lithium aluminum hydride THF solution (1.0 M, 5.0 ml) was added dropwise to the solution at 0° C., and the mixture was stirred at the same temperature for 2 hours. The reaction solution was mixed with sodium sulfate decahydrate at 0° C. and subjected to celite filtration. The resulting filtrate was mixed with water and extracted with ethyl acetate. The thus obtained organic layer was washed with water and saturated brine in that order and dried over anhydrous sodium sulfate. The solvent was evaporated under reduced pressure and the resulting residue was purified by a silica gel column chromatography (ethyl acetate:hexane=2:1) to obtain the title compound (349.5 mg, 72.8%) as white powder.

Melting point: 79–80° C. IR (KBr) $v_{max}$: 3314, 2924, 2848, 2688, 1574, 1434, 1378, 1348, 1186, 1084, 1046, 996, 962, 918, 870, 828, 770, 724 cm$^{-1}$. $^1$H-NMR (CDCl$_3$) δ: 1.65–1.75 (6 H, m), 2.49 (3 H, s), 2.69–2.80 (2 H, m), 2.94–3.05 (2 H, m), 4.66 (2 H, s), 7.35 (1 H, s).

REFERENCE EXAMPLE 83

2-Methyl-6,7,8,9-tetrahydro-5H-cyclohepta[b] pyridine-3-carbaldehyde

In an atmosphere of argon, 3-hydroxymethyl-2-methyl-6,7,8,9-tetrahydro-5H-cyclohepta[b]pyridine (5.24 g, 27.4 mmol) was dissolved in methylene chloride (150.0 ml), and the solution was mixed with manganese dioxide (15.88 g, 137.0 mmol) at room temperature and stirred at the same temperature for 4 hours. The reaction solution was diluted with ethyl acetate and then filtered. The solvent in the resulting filtrate was evaporated under reduced pressure and the resulting residue was purified by a silica gel column chromatography (ethyl acetate:hexane=1:1) to obtain the title compound (3.76 g, 74.0%) as white powder.

Melting point: 38–40° C. IR (KBr) $v_{max}$: 2928, 2852, 2740, 1700, 1596, 1556, 1444, 1412, 1388, 1256, 1244, 1226, 1190, 758 cm$^{-1}$. $^1$H-NMR (CDCl$_3$) δ: 1.72–1.79 (6 H, m), 2.80 (3 H, s), 2.80–2.88 (2 H, m), 3.02–3.13 (2 H, m), 7.76 (1 H, s), 10.28 (1 H, s).

REFERENCE EXAMPLE 84

Methyl 3-(2-methyl-6,7,8,9-tetrahydro-5H-cyclohepta[b]pyridin-3-yl)-2-acrylate

2-Methyl-6,7,8,9-tetrahydro-5H-cyclohepta[b]pyridine-3-carbaldehyde (1.23 g, 6.48 mmol) was dissolved in toluene (8.0 ml), and the solution was mixed with methyl (triphenylphosphoranilidene)acetate (2.76 g, 8.09 mmol) at room temperature and stirred at 60° C. for 22 hours. The solvent was evaporated under reduced pressure and the resulting residue was purified by a silica gel column chromatography (ethyl acetate:hexane=1:1) to obtain the title compound (1.49 g, 93.5%) as pale yellow oil.

IR (neat) ν$_{max}$: 2924, 2852, 1720, 1632, 1596, 1438, 1312, 1272, 1192, 1170, 978 cm$^{-1}$. $^1$H-NMR (CDCl$_3$) δ: 1.65–1.87 (6 H, m), 2.59 (3 H, s), 2.71–2.81 (2 H, m), 2.96–3.07 (2 H, m), 3.81 (3 H, s), 6.33 (1 H, d, J=16.0 Hz), 7.49 (1 H, s), 7.89 (1 H, d, J=16.0 Hz).

INVENTIVE EXAMPLE 1

2-Methyl-6,7,8,9-tetrahydro-5H-cyclohepta[b] pyridine-3-carbonylguanidine

In an atmosphere of argon, metallic sodium (325.2 mg, 0.014 g atom) was dissolved in anhydrous methanol (20.0 ml) at room temperature, and the solution was mixed with guanidine hydrochloride (1.35 g, 14.1 mmol) at 0° C. After 1 hour of stirring at room temperature, the thus precipitated sodium chloride was removed by filtration using a glass filter and the resulting filtrate was evaporated under reduced pressure to obtain free guanidine. Guanidine and ethyl 2-methyl-6,7,8,9-tetrahydro-5H-cyclohepta[b]pyridine-3-carboxylate (500.0 mg, 2.02 mmol) were suspended in 2-propanol (12.0 ml) and heated under reflux for 18 hours. After cooling, the solvent was evaporated under reduced pressure, and the resulting residue was mixed with water and extracted with ethyl acetate. The thus obtained organic layer was dried over anhydrous sodium sulfate, the solvent was evaporated under reduced pressure and then the thus formed crystals were washed with ether to obtain the title compound (165.1 mg, 31.2%) as white powder.

Melting point: 230–232° C. IR (KBr) ν$_{max}$: 3388, 3320, 3080, 1652, 1600, 1526, 1454, 1438, 1402, 1344, 892 cm$^{-1}$. $^1$H-NMR (CDCl$_3$-CD$_3$OD) δ: 1.40–2.00 (6 H, m), 2.66 (3 H, s), 2.45–2.90 (2 H, m), 2.90–3.10 (2 H, m), 7.66 (1 H, s).

INVENTIVE EXAMPLE 2

2-Methyl-5,6,7,8-tetrahydrocyclohexa[b]pyridine-3-carbonylguanidine

In the same manner as described in Inventive Example 1, the title compound (46.6 mg, 8.5%) was obtained as white powder from ethyl 2-methyl-5,6,7,8-tetrahydrocyclohexa[b]pyridine-3-carboxylate (514.4 mg, 2.35 mmol) and guanidine hydrochloride (1.72 g, 18.0 mmol).

Melting point: 235–237° C. IR (KBr) ν$_{max}$: 3384, 3192, 2944, 1650, 1620, 1530, 1452, 1434, 1406, 1372, 1342, 1304, 1262, 1192, 662, 634 cm$^{-1}$. $^1$H-NMR (CDCl$_3$-CD$_3$OD) δ: 1.26–1.96 (4 H, m), 1.99–2.07 (4 H, m), 2.74 (3 H, s), 2.74–2.87 (4 H, m), 7.67 (1 H, s).

INVENTIVE EXAMPLE 3

2-Methyl-5,6,7,8,9,10-hexahydrocyclooocta[b] pyridine-3-carbonylguanidine

In the same manner as described in Inventive Example 1, the title compound (238.6 mg, 44.4%) was obtained as white powder from ethyl 2-methyl-5,6,7,8,9,10-hexahydrocyclooocta[b]pyridine-3-carboxylate (500.0 mg, 2.02 mmol) and guanidine hydrochloride (1.35 g, 14.1 mmol).

Melting point: 208–211° C. IR (KBr) ν$_{max}$: 3356, 3176, 2924, 1680, 1596, 1524, 1444, 1412, 1374, 1352 cm$^{-1}$. $^1$H-NMR (CDCl$_3$-DMSO-d$_6$) δ: 1.15–1.90 (6 H, m), 2.20–2.50 (2 H, m), 2.71 (3 H, s), 2.55–2.80 (2 H, m), 2.80–3.05 (2 H, m), 7.76 (1 H, s).

INVENTIVE EXAMPLE 4

2-Phenyl-6,7,8,9-tetrahydro-5H-cyclohepta[b] pyridine-3-carbonylguanidine

In the same manner as described in Inventive Example 1, the title compound (261.1 mg, 39.8%) was obtained as white amorphous from ethyl 2-phenyl-5,6,7,8,9-tetrahydro-5H-cyclohepta[b]pyridine-3-carboxylate (629.8 mg, 2.13 mmol) and guanidine hydrochloride (2.04 g, 21.3 mmol).

IR (KBr) ν$_{max}$: 3400, 2924, 2852, 1594, 1522, 1432, 1402, 1364, 1348, 1266, 1242, 1210, 894, 758, 698 cm$^{-1}$. $^1$H-NMR (CDCl$_3$-CD$_3$OD) δ: 1.70–1.98 (6 H, m), 2.78–2.88 (2 H, m), 3.05–3.14 (2 H, m), 7.28–7.37 (3 H, m), 7.58–7.66 (3 H, m).

INVENTIVE EXAMPLE 5

2-Isopropyl-6,7,8,9-tetrahydro-5H-cyclohepta[b] pyridine-3-carbonylguanidine

In the same manner as described in Inventive Example 1, the title compound (43.1 mg, 5.7%) was obtained as white powder from ethyl 2-isopropyl-6,7,8,9-tetrahydro-5H-cyclohepta[b]pyridine-3-carboxylate (721.0 mg, 2.76 mmol) and guanidine hydrochloride (2.65 g, 27.7 mmol).

Melting point: 198–199° C. IR (KBr) ν$_{max}$: 3432, 2928, 1656, 1568, 1520, 1452, 1414, 1376, 1350, 1312, 1276, 1238, 898, 814, 512 cm$^{-1}$. $^1$H-NMR (CDCl$_3$-CD$_3$OD) δ: 1.27 (6 H, d, J=6.8 Hz), 1.64–1.94 (6 H, m), 2.68–2.79 (2 H, m), 2.96–3.07 (2 H, m), 3.45–3.66 (1 H, m), 7.50 (1 H, s).

INVENTIVE EXAMPLE 6

2-Ethyl-6,7,8,9-tetrahydro-5H-cyclohepta[b] pyridine-3-carbonylguanidine (Compound C)

In the same manner as described in Inventive Example 1, the title campound (117.2 mg, 16.6%) was obtained as white powder from ethyl 2-ethyl-6,7,8,9-tetrahydro-5H-cyclohepta[b]pyridine-3-carboxylate (672.4 mg, 2.72 mmol) and guanidine hydrochloride (2.61 g, 27.3 mmol).

Melting point: 211–214° C. IR (KBr) ν$_{max}$: 3372, 3172, 2968, 2928, 2852, 1654, 1596, 1562, 1526, 1454, 1438, 1402, 1342, 1162 cm$^{-1}$. $^1$H-NMR (CDCl$_3$-CD$_3$OD) δ: 1.26 (3 H, t, J=7.5 Hz), 1.66–1.84 (6 H, m), 2.45 (4 H, br-s), 2.70–2.81 (2 H, m), 2.89–3.13 (2 H, m), 3.02 (2 H, q, J=7.5 Hz), 7.61 (1 H, s).

INVENTIVE EXAMPLE 7

2-Trifluoromethyl-6,7,8,9-tetrahydro-5H-cyclohepta [b]pyridine-3-carbonylguanidine (Compound G)

In the same manner as described in Inventive Example 1, the title compound (517.4 mg, 34.7%) was obtained as white powder from ethyl 2-trifluoromethyl-6,7,8,9-tetrahydro-5H-cyclohepta[b]pyridine-3-carboxylate (1.43 g, 4.97 mmol) andguanidine hydrochloride (3.86 g, 40.4 mmol).

Melting point: 226–229° C. IR (KBr) $v_{max}$: 3432, 1658, 1604, 1560, 1526, 1460, 1410, 1370, 1350, 1312, 1186, 1140, 1122 cm$^{-1}$. $^1$H-NMR (CDCl$_3$-CD$_3$OD) δ: 1.67–1.92 (6 H, m), 2.78–2.88 (2 H, m), 3.04–3.15 (2 H, m), 7.62 (1 H, s).

INVENTIVE EXAMPLE 8

2-Chloro-6,7,8,9-tetrahydro-5H-cyclohepta[b]pyridine-3-carbonylguanidine (Compound H)

In the same manner as described in Inventive Example 1, the title compound (242.5 mg, 57.6%) was obtained as white powder from methyl 2-chloro-6,7,8,9-tetrahydro-5H-cyclohepta[b]pyridine-3-carboxylate (400.0 mg, 1.58 mmol) and guanidine hydrochloride (1.06 g, 11.1 mmol).

Melting point: 228–230° C. IR (KBr) $v_{max}$: 3416, 3320, 2928, 1656, 1604, 1524, 1450, 1422, 1378, 1312 cm$^{-1}$. $^1$H-NMR (CDCl$_3$-CD$_3$OD) δ: 1.40–2.10 (6 H, m), 2.50–2.90 (2 H, m), 2.90–3.20 (2 H, m), 7 64 (1 H, s).

INVENTIVE EXAMPLE 9

9-Hydroxy-2-methyl-6,7,8,9-tetrahydro-5H-cyclohepta[b]pyridine-3-carbonylguanidine When the method of Inventive Example 1 was repeated using ethyl 9-acetoxy-2-methyl-6,7,8,9-tetrahydro-5H-cyclohepta[b]pyridine-3-carboxylate (450.0 mg, 1.55 mmol) and guanidine hydrochloride (2.67 g, 28.0 mmol), hydrolysis of the acetoxy group occurred at the same time, and the title compound (237.8 mg, 58.9%) was obtained as white powder.

Melting point: 207–210° C. IR (KBr) $v_{max}$: 3348, 2928, 1650, 1600, 1528, 1446, 1410, 1344, 1294, 1046 cm$^{-1}$. $^1$H-NMR (CDCl$_3$-CD$_3$OD) δ: 1.70–2.35 (6 H, m), 2.70 (3 H, s), 2.75–3.30 (2 H, m), 4.55–4.80 (1 H, m), 7.74 (1 H, s).

INVENTIVE EXAMPLE 10

6,7,8,9-Tetrahydro-5H-cyclohepta[b]pyridine-3-carbonylguanidine

In the same manner as described in Inventive Example 1, the title compound (270.6 mg, 58.3%) was obtained as white powder from methyl 6,7,8,9-tetrahydro-5H-cyclohepta[b]pyridine-3-carboxylate (410.0 mg, 2.00 mmol) and guanidine hydrochloride (1.34 g, 14.0 mmol).

Melting point: 235–237° C. IR (KBr) $v_{max}$: 3444, 3328, 3172, 2932, 1654, 1580, 1524, 1410, 1364 cm$^{-1}$. $^1$H-NMR (CDCl$_3$-CD$_3$OD) δ: 1.40–2.00 (6 H, m), 2.70–2.93 (2 H, m), 2.93–3.20 (2 H, m), 8.06 (1 H, d, J=2.0 Hz), 8.91 (1 H, d, J=2.0 Hz).

INVENTIVE EXAMPLE 11

9-Hydroxy-6,7,8,9-tetrahydro-5H-acyclohepta[b]pyridine-3-carbonylguanidine

In the same manner as described in Inventive Example 1, the title compound (202.6 mg, 53.7%) was obtained as white powder from methyl 9-acetoxy-6,7,8,9-tetrahydro-5H-cyclohepta[b]pyridine-3-carboxylate (400.0 mg, 1.52 mmol) and guanidine hydrochloride (1.02 g, 10.6 mmol).

Melting point: 193–195° C. IR (KBr) $v_{max}$: 3388, 2924, 1658, 1596, 1562, 1532, 1444, 1362 cm$^{-1}$. $^1$H-NMR (CDCl$_3$-CD$_3$OD) δ: 1.65–2.40 (6 H, m), 2.63–2.90 (2 H, m), 4.79 (1 H, dd, J=10.8, 2.0 Hz), 8.12 (1 H, d, J=1.8 Hz), 9.03 (1 H, d, J=1.8 Hz).

INVENTIVE EXAMPLE 12

2-Methoxy-6,7,8,9-tetrahydro-5H-cyclohepta[b]pyridine-3-carbonylguanidine (Compound I)

In the same manner as described in Inventive Example 1, the title compound (378.1 mg, 65.0%) was obtained as white powder from methyl 2-methoxy-6,7,8,9-tetrahydro-5H-cyclohepta[b]pyridine-3-carboxylate (521.9 mg, 2.22 mmol) and guanidine hydrochloride (1.48 g, 15.5 mmol).

Melting point: 213–215° C. IR (KBr) $v_{max}$: 3408, 2924, 1658, 1600, 1562, 1462, 1426, 1364, 1290, 1224, 1194 cm$^{-1}$. $^1$H-NMR (CDCl$_3$-CD$_3$OD) δ: 1.30–2.10 (6 H, m), 2.40–2.86 (2 H, m), 2.86–3.00 (2 H, m), 4.01 (3 H, s), 7.81 (1 H, s).

INVENTIVE EXAMPLE 13

2-Methoxymethyl-6,7,8,9-tetrahydro-5H-cyclohepta[b]pyridine-3-carbonylguanidine

In the same manner as described in Inventive Example 1, the title compound (34.1 mg, 3.4%) was obtained as white powder from methyl 2-methoxymethyl-6,7,8,9-tetrahydro-5H-cyclohepta[b]pyridine-3-carboxylate (910.3 mg, 3.65 mmol) and guanidine hydrochloride (3.70 g, 38.8 mmol).

Melting point: 196–198° C. IR (KBr) $v_{max}$: 3404, 3300, 1646, 1600, 1530, 1450, 1404, 1362, 1338, 1108, 628 cm$^{-1}$. $^1$H-NMR (CDCl$_3$-CD$_3$OD) δ: 1.58–1.88 (6 H, m), 2.76–2.86 (2 H, m), 3.01–3.12 (2 H, m), 3.41 (3 H, s), 4.81 (2 H, s), 7.76 (1 H, s).

INVENTIVE EXAMPLE 14

2-(3-Pyridyl)-6,7,8 9-tetrahydro-5H-cyclohepta[b]pyridine-3-carbonylguanidine (Compound J)

In the same manner as described in Inventive Example 1, the title compound (168.7 mg, 10.8%) was obtained as white amorphous from ethyl 2-(3-pyridyl)-6,7,8,9-tetrahydro-5H-cyclohepta[b]pyridine-3-carboxylate (1.49 g, 5.03 mmol) and guanidine hydrochloride (4.78 g, 50.1 mmol).

IR (KBr) $v_{max}$: 3332, 3160, 2924, 2848, 1592, 1524, 1442, 1408, 1362, 1346, 1314, 894, 750, 716 cm$^{-1}$. $^1$H-NMR (CDCl$_3$-CD$_3$OD) δ: 1.59–1.90 (6 H, m), 2.81–2.91 (2 H, m), 3.06–3.16 (2 H, m), 7.37 (1 H, dd, J=7.7, 5.1 Hz), 7.75 (1 H, s), 8.07 (1 H, br-d, J=7.7 Hz), 8.46–8.51 (1 H, m), 8.75 (1 H, br-s).

INVENTIVE EXAMPLE 15

2-(1-Methylpyrrolylmethyl-2-yl)-6,7,8,9-tetrahydro-5H-cyclohepta[b]pyridine-3-carbonylguanidine In the same manner as described in Inventive Example 1, the title compound (156.0 mg, 11.8%) was obtained as white powder from ethyl 2-(1-methylpyrrolylmethyl-2-yl)-6,7,8,9-tetrahydro-5H-cyclohepta[b]pyridine-3-carboxylate (1.27 g, 4.06 mmol) andguanidine hydrochloride (3.91 g, 40.9 mmol).

Melting point: 193–194° C. IR (KBr) $v_{max}$: 3400, 3288, 3108, 2924, 2852, 1644, 1586, 1514, 1452, 1416, 1364, 1352, 1318, 1288, 892, 754 cm$^{-1}$. $^1$H-NMR (CDCl$_3$-CD$_3$OD) δ: 1.58–1.90 (6 H, m), 2.15–2.35 (4 H, m), 2.71–2.81 (2 H, m), 2.95–3.05 (2 H, m), 3.56 (3 H, s), 4.41 (2 H, s), 5.06 (1 H, br-s), 5.90–5.93 (1 H, m), 6.47 (1 H, br-s), 7.68 (1 H, s)

INVENTIVE EXAMPLE 16

2-(2-Thienyl)-6,7,8,9-tetrahydro-5H-cyclohepta[b]pyridine-3-carbonylguanidine

In the same manner as described in Inventive Example 1, the title compound (400.1 mg, 15.5%) was obtained as white powder from ethyl 2-(2-thienyl)-6,7,8,9-tetrahydro-5H-cyclohepta[b]pyridine-3-carboxylate (2.47 g, 8.20 mmol) and guanidine hydrochloride (7.82 g, 81.8 mmol)

Melting point: 210–213° C. IR (KBr) $v_{max}$: 3428, 2928, 1660, 1608, 1532, 1438, 1394, 1356, 1346, 1330, 890, 828, 704 cm$^{-1}$. $^1$H-NMR (CDCl$_3$-CD$_3$OD) δ: 1.59–1.78 (6 H, m), 2.73–2.83 (2 H, m), 3.00–3.10 (2 H, m), 7.00 (1 H, dd, J=4.8, 4.0 Hz), 7.29–7.46 (3 H, m).

INVENTIVE EXAMPLE 17

2-Methyl-6,7,8,9-tetrahydro-5H-cyclohepta[b]pyridine-3-carbonylguanidine

In an atmosphere of argon, metallic sodium (588.8 mg, 0.026 g atom) was dissolved in anhydrous methanol (20.0 ml) at room temperature, and the solution was mixed with guanidine hydrochloride (2.45 g, 25.6 mmol) at 0° C. After 30 minutes of stirring at room temperature, the thus precipitated sodium chloride was removed by filtration using a glass filter and the resulting filtrate was evaporated under reduced pressure to obtain free guanidine. In an atmosphere of argon, 2-methyl-6,7,8,9-tetrahydro-5H-cyclohepta[b]pyridine-3-carboxylic acid (525.6 mg, 2.56 mmol) was suspended in dichloromethane (4.0 ml) and mixed with oxalyl chloride (0.56 ml, 6.36 mmol) at 0° C. by its dropwise addition. After addition of DMF (1 drop), the mixture was stirred at the same temperature for 2 hours. The residue obtained by evaporating the solvent was suspended in THF (12.0 ml) and added dropwise to guanidine THF suspension (8.0 ml), and the mixture was stirred at 60° C. for 17 hours. After cooling, the solvent was evaporated under reduced pressure, and the resulting residue was mixed with water and extracted with ethyl acetate. The thus obtained organic layer was washed with saturated sodium bicarbonate aqueous solution and saturated brine in that order and dried over anhydrous sodium sulfate. The solvent was evaporated under reduced pressure and the thus formed crystals were washed with ether to obtain the title compound (172.0 mg, 27.3%) as white powder.

INVENTION EXAMPLE 18

2-Methyl-6,7,8,9-tetrahydro-5H-cyclohepta[b]pyridine-3-carbonylguanidine

In an atmosphere of argon, metallic sodium (446.6 mg, 0.019 g atom) was dissolved in anhydrous methanol (15.0 ml) at room temperature, and the solution was mixed with guanidine hydrochloride (1.89 g, 19.7 mmol) at 0° C. After 30 minutes of stirring at room temperature, the thus precipitated sodium chloride was removed by filtration using a glass filter and the resulting filtrate was evaporated under reduced pressure to obtain free guanidine. In an atmosphere of argon, 2-methyl-6,7,8,9-tetrahydro-5H-cyclohepta[b]pyridine-3-carboxylic acid (406.3 mg, 1.98 mmol) was suspended in THF (8.0 ml) and mixed with CDI (491.5 mg, 2.97 mmol) at room temperature. This was stirred at room temperature for 2 hours and then at 50° C. for 1 hour, mixed with the previously obtained guanidine THF suspension (6.0 ml) by its dropwise addition and then stirred at room temperature for 18 hours After evaporation of the solvent under reduced pressure, the thus obtained residue was mixed with waterandextractedwith ethyl acetate. The thus obtained organic layer was washed with saturated brine and dried over anhydrous sodium sulfate. The solvent was evaporated under reduced pressure and the thus formed crystals were washed with ether to obtain the title compound (192.5 mg, 39.5%) as white powder.

INVENTIVE EXAMPLE 19

4-Chloro-2-methyl-6,7,8,9-tetrahydro-5H-cyclohepta[b]pyridine- 3-carbonylguanidine When the method of Inventive Example 17 was repeated using 2-methyl-4-nitro-6,7,8,9-tetrahydro-5H-cyclohepta[b]pyridine-3-carboxylic acid (750.1 mg, 3.00 mmol) and guanidine hydrochloride (2.77 g, 29.0 mmol), chlorination of the nitro group occurred at the same time and the title compound (134.5 mg, 16.0%) was obtained as white powder.

Melting point: 210–212° C. IR (KBr) $v_{max}$: 3280, 3040, 2924, 1676, 1588, 1532, 1410, 1348, 904 cm$^{-1}$. $^1$H-NMR (CDCl$_3$-CD$_3$OD) δ: 1.62–1.76 (6 H, m), 2.48 (3 H, s), 2.48–2.58 (2 H, m), 2.97–3.05 (2 H, m). MS (FAB: m/z): 281 (M$^+$+1).

INVENTIVE EXAMPLE 20

2-Methyl-4-nitro-6,7,8,9-tetrahydro-5H-cyclohepta[b]pyridine-3-carbonylguanidine In the same manner as described in Inventive Example 18, the title compound (193.1 mg, 53.9%) was obtained as pale yellow powder from 2-methyl-4-nitro-6,7,8,9-tetrahydro-5H-cyclohepta[b]pyridine-3-carboxylic acid (308.9 mg, 1.23 mmol) and guanidine hydrochloride (1.19 g, 12.5 mmol).

Melting point: 220–222° C. (decomp.) IR (KBr) $v_{max}$: 3400, 3208, 2932, 1672, 1596, 1536, 1442, 1422, 1406, 1380, 1346, 1022, 754 cm$^{-1}$. $^1$H-NMR (CDCl$_3$-CD$_3$OD) δ: 1.64–1.78 (6 H, m), 2.63 (3 H, s), 2.63–2.70 (2 H, m), 3.04–3.15 (2 H, m). MS (FAB: m/z): 292 (M$^+$+1).

INVENTIVE EXAMPLE 21

4-Methoxy-2-methyl-6,7,8,9-tetrahydro-5H-cyclohepta[b]pyridine-3-carbonylguanidine In the same manner as described in Inventive Example 18, the title compound (350.2 mg, 41.3%) was obtained as white powder from 4-methoxy-2-methyl-6,7,8,9-tetrahydro-5H-cyclohepta[b]pyridine-3-carboxylic acid (721.9 mg, 3.07 mmol) and guanidine hydrochloride (2.93 g, 30.7 mmol).

Melting point: >290° C. IR (KBr) $v_{max}$: 3392, 2984, 2920, 2852, 1666, 1592, 1528, 1446, 1414, 1362, 1342, 1294, 1266, 1206, 1078, 906, 634 cm$^{-1}$. $^1$H-NMR (CDCl$_3$-CD$_3$OD) δ: 1.61–1.86 (6 H, m), 2.46 (3 H, s), 2.75–2.85 (2 H, m), 2.92–3.03 (2 H, m), 3.81 (3 H, s).

INVENTIVE EXAMPLE 22

2-Fluoromethyl-6,7,8,9-tetrahydro-5H-cyclohepta[b]pyridine-3-carbonylguanidine

By a method similar to that of Inventive Example 1, the title compound (291.0 mg, 32.1%) was obtained as white powder from ethyl 2-fluoromethyl-6,7,8,9-tetrahydro-5H-cyclohepta[b]pyridine-3-carboxylate (862.0 mg, 3.43 mmol) and guanidine hydrochloride (3.29 g, 34.4 mmol).

Melting point: 128–130° C. IR (KBr) $v_{max}$: 3452, 3316, 3144, 2924, 1852, 1704, 1650, 1596, 1562, 1524, 1456, 1406, 1364, 1346, 1290, 1274, 894, 756 cm$^{-1}$. $^1$H-NMR (CDCl$_3$-CD$_3$OD) δ: 1.58–1.94 (6 H, m), 2.78–2.88 (2 H, m), 3.03–3.14 (2 H, m), 5.49 (1 H, s), 6.02 (1 H, s), 7.90 (1 H, s). MS (FAB: m/z): 265 (M$^+$+1).

INVENTIVE EXAMPLE 23

9-Methoxy-2-methyl-6,7,8,9-tetrahydro- 5H-cyclohepta[b]pyridine-3-carbonylguanidine
(Compound F)

By a method similar to that of Inventive Example 1, the title compound (275.0 mg, 41.4%) was obtained as white amorphous from ethyl 9-methoxy-2-methyl-6,7,8,9-tetrahydro-5H-cyclohepta[b]pyridine-3-carboxylate (632.8 mg, 2.40 mmol) and guanidine hydrochloride (2.32 g, 24.3 mmol).

IR (KBr) $v_{max}$: 3336, 3192, 2928, 2852, 1598, 1524, 1438, 1412, 1336, 1194, 1160, 1150, 1094, 1074, 1044, 898, 750, 580 cm$^{-1}$. $^1$H-NMR (CDCl$_3$) δ: 1.69–2.16 (4 H, m), 2.39–2.71 (2 H, m), 2.71 (3 H, s), 2.75–3.09 (2 H, m), 3.30 (3 H, s), 4.52 (1 H, d, J=6.8 Hz), 7.75 (1 H, s). MS (FAB: m/z): 277 (M$^+$+1).

INVENTIVE EXAMPLE 24

(3-Carbonylguanidino-2-methyl-6,7,8,9-tetrahydro-5H-cyclohepta[b]pyridin-9-yl) nitrate In the same manner as described in Inventive Example 18, the title compound (350.8 mg, 25.0%) was obtained as white amorphous from (3-carboxy-2-methyl-6,7,8,9-tetrahydro-5H-cyclohepta[b]pyridin-9-yl) nitrate (1.21 g, 4.56 mmol) and guanidine hydrochloride (4.43 g, 46.4 mmol).

IR (KBr) $v_{max}$: 3392, 2932, 1636, 1600, 1524, 1440, 1416, 1352, 1304, 1280, 1216, 1198, 1162, 996, 862, 800, 752, 664, 556, 508 cm$^{-1}$. $^1$H-NMR (CDCl$_3$-CD$_3$OD) δ: 1.69–2.30 (6 H, m), 2.67 (3 H, s), 2.67–2.93 (2 H, m), 6.00–6.08 (1 H, br-s), 7.28 (1 H, s). MS (FAB: m/z): 308 (M$^+$+1).

INVENTIVE EXAMPLE 25

9-Chloro-2-methyl-6,7,8,9-tetrahydro-5H-cyclohepta[b]pyridine-3-carbonylguanidine In an atmosphere of argon, guanidine hydrochloride (4.08 g, 42.7 mmol) was added to 28% sodium methoxide methanol solution (8.0 ml, 41.5 mmol) at 0° C. After 30 minutes of stirring at the same temperature, the thus precipitated sodium chloride was removed by filtration using a glass filter and the resulting filtrate was evaporated under reduced pressure to obtain free guanidine. Guanidine and ethyl 9-chloro-2-methyl-6,7,8,9-tetrahydro-5H-cyclohepta[b]pyridine-3-carboxylate (1.10 g, 4.12 mmol) were suspended in 2-propanol (6.0 ml) and stirred at room temperature for 5 hours. The solvent was evaporated under reduced pressure, and the resulting residue was mixed with water and extracted with ethyl acetate. The thus obtained organic layer was washed with saturated brine and dried over anhydrous sodium sulfate. The solvent was evaporated under reduced pressure and the resulting residue was purified by a silica gel column chromatography (chloroform:methanol=10:1–5:1) to obtain the title compound (494.0 mg, 42.7%) as white powder.

Melting point: 153–156° C. IR (KBr) $v_{max}$: 3404, 3300, 3096, 2932, 1658, 1598, 1526, 1442, 1400, 1344, 1300, 1256, 1222, 1200, 892, 870, 800 cm$^{-1}$. $^1$H-NMR (CDCl$_3$-CD$_3$OD) δ: 1.80–2.78 (6 H, m), 2.66 (3 H, s), 3.10–3.44 (2 H, m), 5.41 (1 H, d, J=4.6 Hz), 7.72 (1 H, s) MS (FAB: m/z): 281 (M++1).

INVENTIVE EXAMPLE 26

2,8-Dimethyl-5,6,7,8-tetrahydrocyclohexa[b]pyridine-3-carbonylguanidine

In the same manner as described in Inventive Example 25, the title compound (512.5 mg, 41.4%) was obtained as white powder from ethyl 2,8-dimethyl-5,6,7,8-tetrahydrocyclohexa[b]pyridine-3-carboxylate (1.17 g, 5.02 mmol) and guanidine hydrochloride (4.79 g, 50.1 mmol).

Melting point: 209–210° C. IR (KBr) $v_{max}$: 3360, 3048, 2968, 2936, 1650, 1602, 1556, 1522, 1444, 1428, 1404, 1372, 1338, 1328, 1288, 1196, 878 cm$^{-1}$. $^1$H-NMR (CDCl$_3$-CD$_3$OD) δ: 1.30 (3 H, d, J=7.0 Hz), 2.04 (4 H, m), 2.04–3.02 (2 H, m), 7.67 (1 H, s). MS (FAB: m/z): 247 (M$^+$+1).

INVENTIVE EXAMPLE 27

2,6-Dimethyl-5,6,7,8-tetrahydrocyclohexa[b]pyridine-3-carbonylguanidine (Compound B)

In the same manner as described in Inventive Example 25, the title compound (534.3 mg, 39.9%) was obtained as white powder from ethyl 2,6-dimethyl-5,6,7,8-tetrahydrocyclohexa[b]pyridine-3-carboxylate (1.27 g, 5.43 mmol) and guanidine hydrochloride (5.22 g, 54.6 mmol).

Melting point: 247–248° C. IR (KBr) $v_{max}$: 3392, 3052, 2956, 2924, 1740, 1654, 1600, 1562, 1526, 1446, 1406, 1352, 1320, 1238, 1190, 874 cm$^{-1}$. $^1$H-NMR (CDCl$_3$-CD$_3$OD) δ: 1 07 (3 H, d, J=5.9 Hz), 1.90–2.50 (4 H, m), 2.66 (3 H, s), 2.66–2.83 (1 H, m), 2.83–2.97 (2 H, m), 7.65 (1 H, s). MS (FAB: m/z): 247 (M$^+$+1).

INVENTIVE EXAMPLE 28

8-Methoxy-2-methyl-5,6,7,8-tetrahydrocyclohexa[b]pyridine-3-carbonylguanidine

In the same manner as described in Inventive Example 25, the title compound (209.5 mg, 16.5%) was obtained as white powder from ethyl 8-methoxy-2-methyl-5,6,7,8-tetrahydrocyclohexa[b]pyridine-3-carboxylate (1.21 g, 4.84 mmol) and guanidine hydrochloride (4.63 g, 48.5 mmol).

Melting point: 231–232° C. (decomp.) IR (KBr) $v_{max}$: 3400, 3340, 3044, 2948, 1656, 1604, 1534, 1454, 1420, 1376, 1342, 1288, 1188, 1092, 1076, 1052, 796, 532 cm$^{-1}$. $^1$H-NMR (CDCl$_3$-CD$_3$OD) δ: 1.71–2.13 (4 H, m), 2.69 (3 H, s), 2.69–2.73 (2 H, m), 3.52 (3 H, s), 4.30–4.37 (1 H, m), 7.55 (1 H, s). MS (FAB: m/z): 263 (M$^+$+1).

INVENTIVE EXAMPLE 29

6-Ethylenedioxy-2-methyl-5,6,7,8-tetrahydrocyclohexa[b]pyridine-3-carbonylguanidine In the same manner as described in Inventive Example 25; the title compound (119 mg, 38.9%) was obtained as white needle crystals from ethyl 6-ethylenedioxy-2-methyl-5,6,7,8-tetrahydrocyclohexa[b]pyridine-3-carboxylate (500 mg, 1.80 mmol) and guanidine hydrochloride (1.21 g, 12.6 mmol).

Melting point: 196–199° C. IR (KBr) $v_{max}$: 3334, 2968, 1650, 1599, 1530, 1449, 1410, 1374, 1350, 1290, 1110, 1062 cm$^{-1}$. $^1$H-NMR (CDCl$_3$-CD$_3$OD) δ: 2.03 (2 H, t, J=6.8 Hz), 1.87–2.60 (2 H, m), 2.67 (3 H, s), 2.83–3.23 (2 H, m), 4.03 (4 H, s), 7.56 (1 H, br-s). MS (FAB: m/z): 291 (M$^+$+1).

INVENTIVE EXAMPLE 30

8-Hydroxy-2-methyl-5,6,7,8-tetrahydrocyclohexa[b]pyridine-3-carbonylguanidine (Compound A)

In the same manner as described in Inventive Example 25, the title compound (224.3 mg, 21.1%) was obtained as white amorphous from ethyl 8-hydroxy-2-methyl-5,6,7,8-tetrahydrocyclohexa[b]pyridine-3-carboxylate (1.01 g, 4.29 mmol) and guanidine hydrochloride (4.10 g, 43.0 mmol).

IR (KBr) $v_{max}$: 3352, 2936, 2864, 1602, 1524, 1414, 1340, 1196, 1070, 1046, 866, 752, 608 cm$^{-1}$. $^1$H-NMR (CDCl₃-CD₃OD) δ: 1.70–2.53 (4 H, m), 2.68 (3 H, s), 2.75–2.90 (2 H, m), 4.59–4.71 (1 H, m), 7.72 (1 H, s). MS (FAB: m/z): 249 (M⁺+1).

INVENTIVE EXAMPLE 31

8-Chloro-2-zethyl-5,6,7,8-tetrahydrocyclohexa[b]pyridine-3-carbonylauanidine

In the same manner as described in Inventive Example 25, the title compound (621.6 mg, 73.1%) was obtained as white powder from ethyl 8-chloro-2-methyl-5,6,7,8-tetrahydrocyclohexa[b]pyridine-3-carboxylate (809.6 mg, 3.19 mmol) and guanidine hydrochloride (3.08 g, 32.2 mmol).

Melting point: 177–179° C. (decomp.) IR (KBr) $v_{max}$: 3460, 3372, 3052, 2956, 1650, 1604, 1560, 1520, 1444, 1408, 1364, 1346, 1332, 1288, 1194, 888, 656 cm⁻¹. ¹H-NMR (CDCl₃-CD₃OD) δ: 2.24–2.84 (6 H, m), 2.52 (3 H, s), 5.23 (1 H, m), 7.70 (1 H, s). MS (FAB: m/z): 267 (M⁺+1).

INVENTIVE EXAMPLE 32

2-Methyl-5,6-dihydrocyclohexa[b]pyridine-3-carbonylguanidine

In the same manner as described in Inventive Example 25, the title compound (165.8 mg, 37.3%) was obtained as pale yellow powder from ethyl 2-methyl-5,6-dihydrocyclohexa[b]pyridine-3-carboxylate (419.7 mg, 1.93 mmol) and guanidine hydrochloride (1.86 g, 19.4 mmol).

Melting point: 216–219° C. (decomp.) IR (KBr) $v_{max}$: 3388, 3316, 3044, 2932, 1658, 1595, 1526, 1436, 1408, 1388, 1370, 1340, 1250, 1198, 868, 812, 752 cm⁻¹. ¹H-NMR (CDCl₃-CD₃OD) δ: 1.71–2.56 (2 H, m), 2.65 (3 H, s), 2.65–2.88 (2 H, m), 6.36 (1 H, dt, J=10.5, 4.0 Hz), 6.59 (1 H, d, J=10.5 Hz), 7.70 (1 H, s). MS (FAB: m/z): 231 (M⁺+1).

INVENTIVE EXAMPLE 33

2-Methyl-6,7-dihydro-5H-cyclohepta[b]pyridine-3-carbonylguanidine (Compound K)

In the same manner as described in Inventive Example 25, the title compound (329.5 mg, 35.7%) was obtained as white powder from ethyl 2-methyl-6,7-dihydro-5H-cyclohepta[b]pyridine-3-carboxylate (874.6 mg, 3.78 mmol) and guanidine hydrochloride (3.71 g, 38.9 mmol).

Melting point: 196–198° C. (decomp.) IR (KBr) $v_{max}$: 3368, 3024, 2928, 1650, 1598, 1522, 1436, 1416, 1388, 1336, 1256, 1230, 1198, 1168, 922, 876, 800 cm⁻¹. ¹H-NMR (CDCl₃-CD₃OD) δ: 1.78–2.07 (2 H, m), 2.37–2.49 (2 H, m), 2.69 (3 H, s), 2.75–2.85 (2 H, m), 6.18 (1 H, dt, J=12.5, 4.2 Hz), 6.64 (1 H, d, J=12.5 Hz), 7.75 (1 H, s). MS (FAB: m/z): 245 (M⁺+1).

INVENTIVE EXAMPLE 34

2-Methyl-6,7-dihydro-5H-cyclohepta[b]pyridine-3-carbonylguanidine (Compound K)

In the same manner as described in Inventive Example 25, the title compound (2.87 g, 29.3%) was obtained as white powder from methyl 2-methyl-6,7-dihydro-5H-cyclohepta[b]pyridine-3-carboxylate (8.72 g, 40.1 mmol) and guanidine hydrochloride (26.92 g, 282.0 mmol).

INVENTIVE EXAMPLE 35

2-Methyl-6-oxa-7,8-dihydrocyclohexa[b]pyridine-3-carbonylruanidine

In the same manner as described in Inventive Example 25, the title compound (453 mg, 60.7%) was obtained as white powder from ethyl 2-methyl-6-oxa-7,8-dihydrocyclohexa[b]pyridine-3-carboxylate (705 mg, 3.19 mmol) and guanidine hydrochloride (2.13 g, 22.3 mmol).

Melting point: 218° C. IR (KBr) $v_{max}$: 3400, 3316, 3034, 2968, 1656, 1602, 1527, 1443, 1407, 1341, 1308, 1194 cm⁻¹. ¹H-NMR (CDCl₃-CD₃OD) δ: 2.71 (3 H, s), 2.97 (2 H, t, J=5.7 Hz), 4.06 (2 H, t, J=5.7 Hz), 4.74 (2 H, s), 7.65 (1 H, br-s). MS (FAB: m/z): 235 (M⁺+1).

INVENTIVE EXAMPLE 36

2,9-Dimethyl-6,7,8,9-tetrahydro-5H-cyclohepta[b]pyridine-3-carbonylguanidine (Compound E)

In the same manner as described in Inventive Example 25, the title compound (320.1 mg, 28.9%) was obtained as white powder from ethyl 2,9-dimethyl-6,7,8,9-tetrahydro-5H-cyclohepta[b]pyridine-3-carboxylate (1.05 g, 4.26 mmol) and guanidine hydrochloride (4.07 g, 42.6 mmol).

Melting point: 201–203° C. IR (KBr) $v_{max}$: 3408, 3092, 2968, 2928, 2852, 1654, 1600, 1526, 1442, 1402, 1342, 1306, 1196, 1164 cm⁻¹. ¹H-NMR (CDCl₃-CD₃OD) δ: 1.35 (3 H, d, J=7.3 Hz), 1.51–1.89 (6 H, m), 2.67 (3 H, s), 2.74–2.90 (2 H, m), 3.11–3.25 (1 H, m), 7.63 (1 H, s). MS (FAB: m/z): 261 (M⁺+1).

INVENTIVE EXAMPLE 37

2-Methyl-9-oxo-6,7,8,9-tetrahydro-5H-cyclohepta[b]pyridine-3-carbonylguanidine

In the same manner as described in Inventive Example 25, the title compound (94.5 mg, 13.2%) was obtained as white powder from methyl 2-methyl-9-oxo-6,7,8,9-tetrahydro-5H-cyclohepta[b]pyridine-3-carboxylate (993.7 mg, 4.26 mmol) and guanidine hydrochloride (4.07 g, 42.6 mmol).

Melting point: 203–205° C. (decomp.) IR (KBr) $v_{max}$: 3404, 3144, 2936, 1688, 1654, 1602, 1524, 1456, 1402, 1336, 1280, 1242, 1188, 1118, 928, 860, 750, 596 cm⁻¹. ¹H-NMR (CDCl₃-CD₃OD) δ: 1.84–2.03 (4 H, m), 2.74 (3 H, s), 2.74–2.89 (2 H, m), 7.81 (1 H, s) MS (FAB: m/z): 261 (M⁺+1).

INVENTIVE EXAMPLE 38

2,8,8-Trimethyl-5,6,7,8-tetrahydrocyclohexa[b]pyridine-3-carbonylguanidine

In the same manner as described in Inventive Example 25, the title compound (186.0 mg, 24.0%) was obtained as white powder from ethyl 2,8,8-trimethyl-5,6,7,8-tetrahydrocyclohexa[b]pyridine-3-carboxylate (737.6 mg, 2.98 mmol) and guanidine hydrochloride (2.85 g, 29.9 mmol).

Melting point: 223–225° C. IR (KBr) $v_{max}$: 3424, 3088, 2940, 1658, 1598, 1580, 1530, 1432, 1400, 1380, 1350, 872 cm⁻¹. ¹H-NMR (CDCl₃-CD₃OD) δ: 1.30 (6 H, s), 1.72–1.75 (4 H, m), 2.66 (3 H, s), 2.66–2.72 (2 H, m), 7.56 (1 H, s). MS (FAB: m/z): 261 (M⁺+1).

INVENTIVE EXAMPLE 39

8-Hydroxyimino-2-methyl-5,6,7,8-tetrahydrocyclohexa[b]pyridine-3-carbonylguanidine In the same manner as described in Inventive Example 25, the title compound (65.5 mg, 10.7%) was obtained as white powder from methyl 8-hydroxyimino-2-methyl-5,6,7,8-tetrahydrocyclohexa[b]pyridine-3-carboxylate (551.2 mg, 2.35 mmol) and guanidine hydrochloride (2.25 g, 23.5 mmol).

Melting point: 196–199° C. (decomp.) IR (KBr) $v_{max}$: 3444, 3300, 1712, 1694, 1588, 1544, 1432, 1412, 1362, 1342, 1276, 946 cm$^{-1}$. $^1$H-NMR (CDCl$_3$-CD$_3$OD) δ: 1.83–2.05 (2 H, m), 2.58–2.98 (4 H, m), 2.72 (3 H, s), 7.95 (1 H, s). MS (FAB: m/z): 262 (M$^+$+1)

INVENTIVE EXAMPLE 40

9-Hydroxymethyl-2-methyl-6,7,8,9-tetrahydro-5H-cyclohepta[b]pyridine-3-carbonylguanidine In the same manner as described in Inventive Example 25, the title compound (114.7 mg, 27.3%) was obtained as white powder from ethyl 9-hydroxymethyl-2-methyl-6,7,8,9-tetrahydro-5H-cyclohepta[b]pyridine-3-carboxylate (400.0 mg, 1.52 mmol) and guanidine hydrochloride (1.02 g, 10.64 mmol).

Melting point: 230–232° C. IR (KBr) $v_{max}$: 3412, 3300, 3128, 2924, 1656, 1598, 1440, 1370, 1184, 1164, 1048, 960, 796 cm$^{-1}$. $^1$H-NMR (CDCl$_3$-CD$_3$OD) δ: 1.10–2.25 (6 H, m), 2.67 (3 H, s), 2.60–3.30 (3 H, m), 3.98 (2 H, d, J=5.7 Hz), 7.70 (1 H, s). MS (FAB: m/z): 277 (M$^+$+1).

INVENTIVE EXAMPLE 41

2-Methyl-9-exomethylene-6,7,8,9-tetrahydro-5H-cyclohepta[b]pyridine-3-carbonylguanidine In the same manner as described in Inventive Example 25, the title compound (127.1 mg, 30.2%) was obtained as white powder from ethyl 2-methyl-9-exomethylene-6,7,8,9-tetrahydro-5H-cyclohepta[b]pyridine-3-carboxylate (400.0 mg, 1.63 mmol) and guanidine hydrochloride (1.09 g, 11.41 mmol).

Melting point: 208–211° C. IR (KBr) $v_{max}$: 3356, 3176, 2924, 1680, 1596, 1524, 1444, 1412, 1374, 1352 cm$^{-1}$. $^1$H-NMR (CDCl$_3$-DMSO-d$_6$) δ: 1.15–1.90 (6 H, m), 2.20–2.50 (2 H, m), 2.71 (3 H, s), 2.55–2.80 (2 H, m), 2.80–3.05 (2 H, m), 7.76 (1 H, s) MS (FAB: m/z): 259 (M$^+$+1).

INVENTIVE EXAMPLE 42

9-(E)-Benzylidene-2-methyl-6,7,8,9-tetrahydro-5H-cyclohepta[b]pyridine-3-carbonylcuanidine In the same manner as described in Inventive Example 25, the title compound (87.7 mg, 17.9%) was obtained as pale yellow powder from ethyl 9-(E)-benzylidene-2-methyl-6,7,8,9-tetrahydro-5H-cyclohepta[b]pyridine-3-carboxylate (983.0 mg, 10.29 mmol) and guanidine hydrochloride (983.0 mg, 10.29 mmol).

Melting point: 134–138° C. IR (KBr) $v_{max}$: 3364, 2928, 2856, 1704, 1588, 1530, 1444, 1374, 1264, 752 cm$^{-1}$. $^1$H-NMR (CDCl$_3$-CD$_3$OD) δ: 1.60–1.96 (4 H, m), 2.04 (4 H, s), 2.45–2.90 (2 H, m), 2.76 (3 H, s), 7.03 (1 H, s), 7.10–7.56 (5 H, m), 7.81 (1 H, s). MS (FAB: m/z): 335 (M$^+$+1).

INVENTIVE EXAMPLE 43

(3-Carbonylguanidino-2-methyl-6,7,8,9-tetrahydro-5H-cyclohepta[b]pyridin-9-yl)methyl nitrate In an atmosphere of argon, 28% sodium methoxide methanol solution (1.58 ml, 8.19 mmol) was dissolved in anhydrous methanol (8.0 ml) at room temperature, and the solution was mixed with guanidine hydrochloride (782.4 mg, 8.19 mmol) at 0° C. and stirred at the same temperature for 1 hour. The thus precipitated sodium chloride was removed by filtration using a glass filter and the resulting filtrate was evaporated under reduced pressure to obtain free guanidine. In an atmosphere of argon, (3-carboxy-2-methyl-6,7,8,9-tetrahydro-5H-cyclohepta[b]pyridin-9-yl)methyl nitrate (310.0 mg, 1.17 mmol) were suspended in anhydrous THF (8.0 ml), mixed with CDI (291.2 mg, 1.76 mmol) at room temperature and then stirred at 50° C. for 1 hour. The reaction solution was added dropwise to the previously obtained guanidine THF suspension (5.0 ml), and the mixture was stirred at room temperature for 2.5 hours. The solvent was evaporated under reduced pressure, and the resulting residue was mixed with water and extracted with ethyl acetate. The thus obtained organic layer was washed with saturated sodium bicarbonate aqueous solution, water and saturated brine in that order and dried over anhydrous sodium sulfate. The solvent was evaporated under reduced pressure, the resulting residue was purified by a silica gel column chromatography (chloroform:methanol=20:1) and then the thus obtained crystals were washed with ether to obtain the title compound (192.1 mg, 51.1%) as white powder.

Melting point: 120–121° C. IR (KBr) $v_{max}$: 3416, 2932, 1632, 1520, 1420, 1374, 1352, 1276, 904, 866 cm$^{-1}$. $^1$H-NMR (CDCl$_3$-CD$_3$OD) δ: 1.20–2.20 (6 H, m), 2.63 (3 H, s), 2.73–2.96 (2 H, m), 3.20–3.46 (1 H, m), 4.74 (1 H, dd, J=10.8, 2.4 Hz), 5.24 (1 H, dd, J=10.8, 5.3 Hz), 7.61 (1 H, s). MS (FAB: m/z): 322 (M$^+$+1).

INVENTIVE EXAMPLE 44

8-Methoxyimino-2-methyl-5,6,7,8-tetrahydrocyclohexa[b]pyridine-3-carbonylguanidine In the same manner as described in Inventive Example 25, the title compound (369.4 mg, 43.1%) was obtained as white powder from methyl 8-methoxyimino-2-methyl-5,6,7,8-tetrahydrocyclohexa[b]pyridine-3-carboxylate (772.9 mg, 3.11 mmol) and guanidine hydrochloride (3.18 g, 33.3 mmol).

Melting point: 238–240° C. (decomp.) IR (KBr) $v_{max}$: 3384, 3128, 2936, 1656, 1594, 1532, 1422, 1342, 1288, 1186, 1046, 926, 882, 802, 746, 574 cm$^{-1}$. $^1$H-NMR (CDCl$_3$-CD$_3$OD) δ: 1.78–1.91 (2 H, m), 2.57–2.89 (4 H, m), 2.73 (3 H, s), 4.10 (3 H, s), 7.73 (1 H, s). MS (FAB: m/z): 276 (M$^+$+1)

INVENTIVE EXAMPLE 45

2-(3-Pyridylmethyloxymethyl)-6,7,8,9-tetrahydro-5H-cyclohepta[b]pyridine-3-carbonylguanidine In the same manner as described in Inventive Example 25, the title compound (20.0 mg, 6.7%) was obtained as pale orange powder from ethyl 2-(3-pyridylmethyloxymethyl)-6,7,8,9-tetrahydro-5H-cyclohepta[b]pyridine-3-carboxylate (284.7 mg, 0.84 mmol) and guanidine hydrochloride (799.8 mg, 8.37 mmol).

Melting point: 99–100° C. IR (KBr) $v_{max}$: 3376, 2920, 2852, 1702, 1596, 1526, 1442, 1346, 1088, 796, 712 cm$^{-1}$. $^1$H-NMR (CDCl$_3$-CD$_3$OD) δ: 1.68–1.76 (6 H, m), 2.74–2.84 (2 H, m), 3.00–3.10 (2 H, m), 4.56 (2 H, s), 4.94 (2 H, s), 7.18–7.32 (1 H, m), 7.67–7.74 (2 H, m), 8.39–8.51 (2 H, m). MS (FAB: m/z): 354 (M$^+$+1).

INVENTIVE EXAMPLE 46

2-{4-[2-(N,N-Dimethylamino)ethylaminocarbonyl]phenoxymethyl}-6,7,8,9-tetrahydro-5H-cyclohepta[b]pyridine-3-carbonylguanidine In the same manner as described in Inventive Example 25, the title compound (268.0 mg, 34.6%) was obtained as white powder from ethyl 2-{4-[2-(N,N-dimethylamino)ethylaminocarbonyl]phenoxymethyl}-6,7,8,9-tetrahydro-5H-cyclohepta[b]pyridine-3-carboxylate (752.5 mg, 1.71 mmol) and guanidine hydrochloride (1.65 g, 17.31 mmol).

Melting point: 193–195° C. IR (KBr) $v_{max}$: 3396, 2928, 1666, 1638, 1612, 1526, 1454, 1402, 1376, 1358, 1324, 1240, 1174, 1034 cm$^{-1}$. $^1$H-NMR (CDCl$_3$-CD$_3$OD) δ: 1.67–1.77 (6 H, m)), 2.30 (6 H, s), 2.54 (2 H, dd, J=6.2, 5.7 Hz), 2.77–2.88 (2 H, m), 3.03–3.13 (2 H, m), 3.41–3.50 (2 H, m), 5.46 (2 H, s), 6.99 (2 H, d, J=8.8 Hz), 7.73 (2 H, d, J=8.8 Hz), 7.76 (1 H, s). MS (FAB: m/z): 453 (M$^+$+1).

INVENTIVE EXAMPLE 47

2-(N,N-Dimethylaminomethyl)-6,7,8,9-tetrahydro-5H-cyclohepta[b]pyridine-3-carbonylguanidine In the same manner as described in Inventive Example 25, the title compound (149.1 mg, 21.5%) was obtained as white powder from ethyl 2-(N,N-dimethylaminomethyl)-6,7,8,9-tetrahydro-5H-cyclohepta[b]pyridine-3-carboxylate (663.2 mg, 2.40 mmol) and guanidine hydrochloride (2.31 g, 24.19 mmol).

Melting point: 210–212° C. IR (KBr) $v_{max}$: 3308, 3064, 2928, 2856, 2824, 1652, 1602, 1526, 1464, 1444, 1412, 1370, 1340, 1314, 1276, 896, 816 cm$^{-1}$. $^1$H-NMR (CDCl$_3$-CD$_3$OD) δ: 1.65–1.76 (6 H, m), 2.25 (6 H, s), 2.75–2.84 (2 H, m), 2.99–3.09 (2 H, m), 3.85 (2 H, s), 7.67 (1 H, s). MS (FAB: m/z): 290 (M$^+$+1).

INVENTIVE EXAMPLE 48

2-Methyl-5-oxo-6,7,8,9-tetrahydro-5H-cyclohepta[b]pyridine-3-carbonylguanidine

In the same manner as described in Inventive Example 25, the title compound (75.2 mg, 26.1%) was obtained as white powder from ethyl 2-methyl-5-oxo-6,7,8,9-tetrahydro-5H-cyclohepta[b]pyridine-3-carboxylate (274.7 mg, 742.3 mmol) and guanidine hydrochloride (742.3 mg, 7.77 mmol).

Melting point: 213–215° C. IR (KBr) $v_{max}$: 3416, 3332, 3092, 2944, 1680, 1658, 1600, 1526, 1454, 1400, 1336, 1268, 878 cm$^{-1}$. $^1$H-NMR (CDCl$_3$-CD$_3$OD) δ: 1.70–2.03 (4 H, m), 2.55–2.90 (2 H, m) 2.77 (3 H, s), 3.15 (2 H, t, J=5.9 Hz), 8.35 (1 H, s) Ms (FAB: m/z): 2 61 (M$^+$+1).

INVENTIVE EXAMPLE 49

5-tert-Butyldimethylsilyloxy-2-methyl-6,7,8,9-tetrahydro-5H-cyclohepta[b]pyridine-3-carbonylguanidine In the same manner as described in Inventive Example 18, the title comupound (262.5 mg, 85.1%) was obtained as white powder from 5-tert-butyldimethylsilyloxy2-methyl-6,7,8,9-tetrahydro-5H-cyclohepta[b]pyridine-3-carboxylic acid (262.3 mg, 0.82 mmol) and guanidine hydrochloride (548.0 mg, 5.74 mmol).

Melting point: 198–200° C. IR (KBr) $v_{max}$: 3352, 3164, 2954, 1650, 1598, 1408, 1356, 1318, 1254, 31096, 1018, 886 cm$^{-1}$. $^1$H-NMR (CDCl$_3$-CD$_3$OD) δ: 0.09 (6 H, s), 0.93 (9 H, s), 1.40–1.95 (6 H, m), 2.75–3.00 (2 H, m), 2.68 (3 H, s), 4.80 (1 H, br-s), 7.95 (1 H, s).

Inventive Examnple 50

5-Hydroxy-2-methyl-6,7,8,9-tetrahydro-5H-cyclohepta[b]pridine-3-carbonylguanidine (Compound D)

5-tert-Butyldirnethylsilyloxy-2-methyl-6,7,8,9-tetrahydro-5H-cyclohepta[b]pyridine-3-carbonylguanidine (252.5 mg, 0.37 mmol) was dissolved in 5% hydrochloric acid methanol solution (10.1 ml) at 0° C. and stirred at room temperature for 14 hours. The solvent was evaporated under reduced pressure, and the thus obtained residue was mixed with chloroform:methanol (4:1), adjusted to pH 9 to 10 with 5% sodium hydroxide aqueous solution and then extracted with chloroform:methanol (4:1). The thus obtained organic layer was washed with water and saturated brine in that order and dried over anhydrous sodium sulfate. The solvent was evaporated under reduced pressure, and the resulting residue was crystallized from chloroform-ether to obtain the title compound (131.0 mg, 74.9%) as white powder.

Melting point: 225–226° C. IR (KBr) $v_{max}$: 3484, 3368, 3188, 2920, 2840, 1635, 1534, 1434, 1364, 1322, 1058, 1042, 890 cm$^{-1}$. $^1$H-NMR (DMSO-d$_6$) δ: 1.30–2.15 (6 H, m), 2.70 (3 H, s), 2.80–3.20 (2 H, m), 4.70–4.95 (1 H, m), 8.10 (1 H, s). MS (FAB: m/z): 263 (M$^+$+1).

INVENTIVE EXAMPLE 51

5-Chloro-2-methyl-6,7,8,9-tetrahydro-5H-cyclohepta[b]pyridine-3-carbonylguanidine In the same manner as described in Inventive Example 18, the title compound (70.0 mg, 35.7%) was obtained as white powder from 5-chloro-2-methyl-6,7,8,9-tetrahydro-5H-cyclohepta[b]pyridine-3-carboxylic acid (217.3 mg, 0.70 mmol) and guanidine hydrochloride (468.1 mg, 4.90 mmol).

Melting point: 122–124.5° C. IR (KBr) $v_{max}$: 3384, 2932, 1630, 1596, 1526, 1440, 1354, 1264, 1212, 1164, 870 cm$^{-1}$. $^1$H-NMR (CDCl$_3$-CD$_3$OD) δ: 1.75–2.55 (6 H, m), 2.70 (3 H, s), 3.00–3.53 (2 H, m), 5.24 (1 H, br-d, J=5.5 Hz), 7.92 (1 H, s). MS (FAB: m/z): 281 (M$^+$+1).

INVENTIVE EXAMPLE 52

2-Methyl-8,9-dihydro-7H-cyclohepta[b]pyridine-3-carbonylguanidine

In the same manner as described in Inventive Example 25, the title compound (91.8 mg, 37.6%) was obtained as white powder from ethyl 2-methyl-8,9-dihydro-7H-cyclohepta[b]pyridine-3-carboxylate (231.0 mg, 1.00 mmol) and guanidine hydrochloride (668.7 mg, 7.00 mmol).

Melting point: 225–227° C. IR (KBr) $v_{max}$: 3388, 3304, 3056, 1652, 1600, 1526, 1454, 1390, 1348, 1312, 880 cm$^{-1}$. $^1$H-NMR (CDCl$_3$-CD$_3$OD) δ: 1.80–2.15 (2 H, m), 2.30–2.60 (2 H, m), 2.75 (3 H, s), 2.95–3.16 (2 H, m), 5.95 (1 H, ddd, J=12.0, 5.1, 5.1 Hz), 6.33 (1 H, d, J=12.0 Hz), 7.73 (1 H, s). MS (FAB: m/z): 245 (M$^+$+1).

INVENTIVE EXAMPLE 53

2-Methyl-9(E)-(3-pyridylmethylene)-6,7,8,9-tetrahydro-5H-cyclohepta[b]pyridine-3-carbonylguanidine In the same manner as described in Inventive Example 25, the title compound (139.8 mg, 41.7%) was obtained as white powder from ethyl 2-methyl-9(E)-(3-pyridylmethylene)-6,7,8,9-tetrahydro-5H-cyclohepta[b]pyridine-3-carboxylate (324.0 mg, 1.00 mmol) and guanidine hydrochloride (668.7 mg, 7.00 mmol)

Melting point: 216–219° C. IR (KBr) $v_{max}$: 3408, 3028, 2932, 1702, 1656, 1596, 1512, 1478, 1414, 1374, 1350 cm$^{-1}$. $^1$H-NMR (CDCl$_3$-CD$_3$OD) δ: 1.60–2.06 (4 H, m), 2.20–3.00 (4 H, m), 2.73 (3 H, s), 6.92 (1 H, s), 7.39 (1 H, d, J=5.1 Hz), 7.84 (1 H, s), 8.45 (1 H, d, J=5.1 Hz), 8.68 (1 H, s) MS (FAB: m/z): 336 (M$^+$+1).

INVENTIVE EXAMPLE 54

2-Methyl-9-(3-pyridylmethyl)-6,7,8,9-tetrahydro-5H-cyclohepta[b]pyridine-3-carbonylguanidine In the same manner as described in Inventive Example 25, the title compound (103.7 mg, 20.1%) was obtained as pale brown powder from ethyl 2-methyl-9-(3-pyridylmethyl)-6,7,8,9-tetrahydro-5H-cyclohepta[b]pyridine-3-carboxylate (500.0 mg, 1.53 mmol) and guanidine hydrochloride (1.02 g, 10.7 mmol).

Melting point: 160–162° C. IR (KBr) $v_{max}$: 3472, 3320, 3036, 2924, 2852, 1656, 1604, 1532, 1414, 1372, 1364, 716 cm$^{-1}$. $^1$H-NMR (CDCl$_3$-CD$_3$OD) δ: 1.30–2.00 (6 H, m), 2.76 (3 H, s), 2.63–3.06 (2 H, m), 3.10–3.60 (3 H, m), 7.05–7.26 (1 H, m), 7.45–7.70 (1 H, m), 7.60 (1 H, s), 8.34 (2 H, s). MS (FAB: m/z): 338 (M$^+$+1).

INVENTIVE EXAMPLE 55

2-Methyl-9-{4-[2-(N,N-dimethylamino)ethylaminocarbonyl]phenoxymethyl}-6,7,8,9-tetrahydro-5H-cyclohepta[b]pyridine-3-carbonylguanidine In the same manner as described in Inventive Example 25, the title compound (68.8 mg, 18.9%) was obtained as white powder from ethyl 2-methyl-9-{4-[2-(N,N-dimethylamino)ethylaminocarbonyl]phenoxymethyl}-6,7,8,9-tetrahydro-5H-cyclohepta[b]pyridine-3-carboxylate (354.0 mg, 0.78 mmol) and guanidine hydrochloride (521.6 mg, 5.46 mmol).

Melting point: 202–204° C. IR (KBr) $v_{max}$: 3396, 2928, 2852, 2784, 1632, 1608, 1532, 1504, 1440, 1376, 1300, 1188, 1104 cm$^{-1}$. $^1$H-NMR (CDCl$_3$-CD$_3$OD) δ: 1.30–2.10 (6 H, m), 2.30 (6 H, s), 2.65 (3 H, s), 3.20–3.65 (3 H, m), 4.31 (1 H, t, J=9.2 Hz), 4.64 (1 H, dd, J=9.2, 4.8 Hz), 7.01 (2 H, d, J=8.8 Hz), 7.66 (1 H, s), 7.78 (2 H, d, J=8.8 Hz). MS (FAB: m/z): 453 (M$^+$+1).

INVENTIVE EXAMPLE 56

3-(2-Methyl-6,7,8,9-tetrahydro-5H-cyclohepta[b]pyridin-3-yl)-2-propenoylguanidine In the same manner as described in Inventive Example 25, the title compound (190.8 mg, 17.4%) was obtained as white powder from methyl 3-(2-methyl-6,7,8,9-tetrahydro-5H-cyclohepta[b]pyridin-3-yl)-2-acrylate (985.3mg, 4.02 mmol) andguanidinehydrochloride (3.84 g, 40.1 mmol).

Melting point: 197–200° C. IR (KBr) $v_{max}$: 3336, 2924, 2852, 1638, 1578, 1524, 1454, 1434, 1352, 1278, 1250, 1192, 974, 750 cm$^{-1}$. $^1$H-NMR (CDCl$_3$-CD$_3$OD) δ: 1.70–1.86 (6 H, m), 2.59 (3 H, s), 2.71–2.81 (2 H, m), 2.94–3.05 (2 H, m), 6.49 (1 H, d, J=15.6 Hz), 7.56 (1 H, s), 7.82 (1 H, d, J=15.6 Hz). MS (FAB: m/z): 273 (M$^+$+1).

INVENTIVE EXAMPLE 57

2-Methyl-6,7,8 9-tetrahydro-5H-cyclohepta[b]pyridine-3-carbonylguanidine maleate 2-Methyl-6,7,8,9-tetrahydro-5H-cyclohepta[b]pyridine-3-carbonylguanidine (26.1 mg, 0.11 mmol) was dissolved in methanol (2.0 ml) and mixed with maleic acid (12.8mg, 0.11 mmol) at room temperature. After heating the reaction solution, the solvent was evaporated under reduced pressure and the thus formed crystals were washed with ether to obtain the title compound (30.2 mg, 75.8%) as white powder.

Melting point: 158–160° C. IR (KBr) $v_{max}$: 3360, 2924, 1706, 1652, 1580, 1554, 1386, 1148, 1118, 1062, 866 cm$^{-1}$. $^1$H-NMR (CDCl$_3$-CD$_3$OD) δ: 1.43–2.03 (6 H, m), 2.67 (3 H, s), 2.70–2.90 (2 H, m), 2.90–3.20 (2 H, m), 6.26 (2 H, s), 7.72 (1 H, s). MS (FAB: m/z): 247 (M$^+$+1−C$_4$H$_5$O$_4$).

INVENTIVE EXAMPLE 58

2,8-Dimethyl-5,6,7,8-tetrahydrocyclohexa[b]pyridine-3-carbonylguanidine maleate

In the same manner as described in Inventive Example 57, the title compound (327.0 mg, 65.9%) was obtained as white powder from 2,8-dimethyl-5,6,7,8-tetrahydrocyclohexa[b]pyridine-3-carbonylguanidine (336.8 mg, 1.37 mmol) and maleic acid (159.7 mg, 1.36 mmol).

Melting point: 172–173° C. IR (KBr) $v_{max}$: 3372, 3208, 1708, 1592, 1548, 1482, 1386, 1362, 1158, 1076, 1006, 866, 724, 666, 564, 502 cm$^{-1}$. $^1$H-NMR (CDCl$_3$-CD$_3$OD) δ: 1.35 (3 H, d, J=7.0 Hz), 1.75–3.13 (7 H, m), 2.65 (3 H, s), 6.26 (2 H, s), 7.61 (1 H, s).

INVENTIVE EXAMPLE 59

2,8-Dimethyl-5,6,7,8-tetrahydrocyclohexa[b]pyridine-3-carbonylguanidine fumarate In the same manner as described in Inventive Example 57, the title compound (413.6 mg, 85.8%) was obtained as white powder from 2,8-dimethyl-5,6,7,8-tetrahydrocyclohexa[b]pyridine-3-carbonylguanidine (327.3 mg, 1.33 mmol) and fumaric acid (156.0 mg, 1.33 mmol).

Melting point: 218–220° C. (decomp.) IR (KBr) $v_{max}$: 3392, 3112, 2928, 2864, 1702, 1608, 1558, 1446, 1360, 1298, 1280, 1168, 784, 586 cm$^{-1}$. $^1$H-NMR (CDCl$_3$-CD$_3$OD) δ: 1.24 (3 H, d, J=7.0 Hz), 1.49–2.00 (4 H, m), 2.33–2.91 (3 H, m), 2.65 (3 H, s), 6.46 (2 H, s), 7.70 (1 H, s).

INVENTIVE EXAMPLE 60

2,8-Dimethyl-5,6,7,8-tetrahydrocyclohexa[b]pyridine-3-carbonylguanidine tartarate In the same manner as described in Inventive Example 57, the title compound (5.63 g, 97.2%) was obtained as white powder from 2,8-dimethyl-5,6,7,8-tetrahydrocyclohexa[b]pyridine-3-carbonylguanidine (3.60 g, 14.6 mmol) and L-(+)-tartaric acid (2.21 g, 14.6 mmol).

Melting point: 114–1170° C. IR (KBr) $v_{max}$: 3384, 2936, 1714, 1598, 1404, 1274, 1214, 1160, 1120, 1076, 678, 618 cm$^{-1}$. $^1$H-NMR (CDCl$_3$-CD$_3$OD) δ: 1.30 (3 H, d, J=6.6 Hz), 1.72–2.03 (4 H, m), 2.61–2.82 (3 H, m), 2.71 (3 H, s), 4.40 (2 H, s), 7.73 (1 H,

INVENTIVE EXAMPLE 61

2-Methyl-6,7-dihydro-5H-cyclohepta[b]pyridine-3-carbonylguanidine maleate

In the same manner as described in Inventive Example 57, the title compound (1.45 g, 87.8%) was obtained as white powder from 2-methyl-6,7-dihydro-5H-cyclohepta[b]pyridine-3-carbonylguanidine (1.12 g, 4.57 mmol) and maleic acid (536.6 mg, 4.58 mmol).

Melting point: 172–173° C. (decomp.) IR (KBr) $v_{max}$: 3360, 3160, 2936, 1708, 1592, 1544, 1476, 1384, 1358, 1268, 1210, 1144, 1072, 1008, 866, 716, 682, 656, 568 cm$^{-1}$. $^1$H-NMR (DMSO-d$_6$) δ: 1.94–2.11 (2 H, m), 2.50–2.57 (2 H, m), 2.67 (3 H, s), 2.74–2.89 (2 H, m), 6.25 (2 H, s), 6.32 (1 H, dt, J=12.5, 4.2 Hz), 6.66 (1 H, d, J=12.5 Hz), 7.68 (1 H, s).

INVENTIVE EXAMPLE 62

2-Methyl-6,7-dihydro-5H-cyclohepta[b]pyridine-3-carbonylguanidine tartarate

In the same manner as described in Inventive Example 57, the title compound (161.8 mg, 82.1%) was obtained as white amorphous from 2-methyl-6,7-dihydro-5H-cyclohepta[b]pyridine-3-carbonylguanidine (123.3 mg, 0.50 mmol) and L-(+)-tartaric acid (76.7 mg, 0.51 mmol).

IR (KBr) $v_{max}$: 3384, 1712, 1592, 1398, 1280, 1214, 1122, 1070, 676, $^1$H-NMR (CDCl$_3$-CD$_3$OD) δ: 1.90–2.10 (2 H, m), 2.45–2.55 (2 H, m), 2.66 (3 H, s), 2.81–2.91 (2 H, m), 4.45 (2 H, s), 6.32 (1 H, dt, J=12.5, 4.0 Hz), 6.65 (1 H, d, J=12.5 Hz), 7.84 (1 H, s).

INVENTIVE EXAMPLE 63

Tablets

| | |
|---|---|
| Maleate of compound K | 10 g |
| Lactose (DMV 200) | 61 g |
| Crystalline cellulose | 10 g |
| Corn Starch | 10 g |
| Hydroxypropylcellulose | 3 g |
| Carboxymethylcellulose calcium | 5 g |
| Magnesium stearate | 0.5 g |
| Talc | 0.5 g |
| Total | 100 g |

Among the above components, maleate of compound K, lactose, crystalline cellulose, corn starch and hydroxypropylcellulose were uniformly mixed, and the mixture was mixed with purified water and made into granules in a mortar. The granules were dried, reduced in size and then mixed with carboxymethylcellulose calcium, magnesium stearate and talc. Using a single punch press, uncoated tablets, each having 7 mm in diameter and weighing 100 mg, were prepared. Each of the uncoated tablets contains 10 mg of the maleate of compound K.

INVENTIVE EXAMPLE 64

Hard Capsules

| | |
|---|---|
| Maleate of compound K | 10 g |
| Lactose (Dai Lactose) | 79 g |
| Corn Starch | 10 g |
| Magnesium stearate | 0.5 g |
| Talc | 0.5 g |
| Total | 100 g |

Among the above components, maleate of compound K, lactose and corn starch were uniformly mixed, and the mixture was further mixed with magnesium stearate and talc. Using a bench type capsule filler, each of No. 4 gelatin capsules was filled with 100 mg of the resulting powder. Each of the thus prepared hard capsules contains 10 mg of the maleate of compound K.

INVENTIVE EXAMPLE 65

Injections

| | |
|---|---|
| Maleate of compound K | 10 g |
| Sodium chloride | 8.5 g |
| Disodium hydrogenphosphate | 1.8 g |
| Crystalline sodium dihydrogenphosphate | 0.2 g |
| Distilled water for injection use | balance |
| Total | 1,000 ml |

According to the above composition, maleate of compound K and each of the additives were dissolved in order in distilled water for injection use. The resulting solution was passed through a membrane filter of 0.22 μm in pore size and dispensed in 1 ml portions into glass anpuls using an automatic dispenser. Each of the resulting ampuls was sealed by melting with a gas burner and then subjected to high pressure steam sterilization using an autoclave, thereby preparing injections. The thus prepared injections contain 10 mg of the maleate of compound K in one ampul.

INVENTIVE EXAMPLE 66

Suppositories

| | |
|---|---|
| Maleate of compound K | 1 g |
| Hard fat (Witepsol H-15) | 49 g |
| Hard fat (Witepsol E-75) | 49 g |
| Total | 100 g |

The above components were put into an aluminum beaker and melted by heating in a hot water bath of 45° C. The melted mixture was distributed, while hot, in 1 g portions into suppository mold plastic packages and then solidified by spontaneous cooling. Each of the thus prepared suppositories contains 10 mg of the maleate of compound K.

INDUSTRIAL APPLICABILITY

The cycloalka[b]pyridine-3-carbonylguanidine derivatives of the present invention having a novel chemical structure or salts thereof can provide a medicament having sodium/proton (Na$^+$/H$^+$) exchange transport inhibitory action.

What is claimed is:

1. A cycloalka[b]pyridine-3-carbonylguanidine derivative represented by the following formula (1):

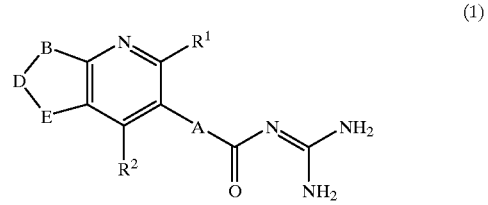

(1)

(wherein R$^1$ represents a halogen atom, a lower alkyl group, a lower alkoxylalkyl group; A represents a single bond; B represents a vinylene group or

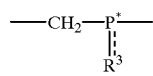

(wherein $R^3$ represents a hydrogen atom, a halogen atom, a hydroxy group, a lower alkyl group, a lower alkylidene group, a lower alkoxyl group, a hydroxyower alkyl group, an aralkyl group, an aralkylidene group, a phenoxy lower alkyl group, a hydroxyimino group, a lower alkoxyimino group, an oxo group or a $(CH_2)_nONO_2$ group (n is 0 or an integer of 1), and P* represents a tertiary carbon group or a carbon atom); D represents a single bond, a methylene group or an ethylene group; and E represents

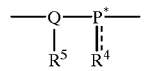

(wherein $R^4$ represents a hydrogen atom, a halogen atom, which may be protected or an oxo group, $R^5$ represents unsubstitution, a hydrogen atom or a lower alkyl group, P* represents a tertiary carbon group or a carbon atom, and Q represents a methine group or an oxygen atom)) or a salt thereof.

2. A sodium/proton ($Na^+/H^+$) exchange transport inhibitor which comprises a cycloalka[b]pyridine-3carbonylguanidine derivative or a salt thereof as claimed in claim 1 as the active ingredient.

3. A method for treating arrhythmia or organ disorders due to ischemia or ischemia reperfusion which comprises administering to a human in need of such prevention or treatment an effective amount of cycloalka[b]pyridine-3-carbonylguanidine derivative or salt thereof as claimed in claim 1 as the active ingredient, together with a pharmaceutical acceptable carrier.

4. A method for treating angina pectoris which comprises administering to a human in need of such treatment an effective amount of a cycloalka[b]pyridine-3carbonylguanidine derivative or salt thereof as claimed in claim 1 as the active ingredient, together with a pharmaceutical acceptable carrier.

5. A method for treating cardiac hypertrophy which comprises administering to a human in need of such treatment an effective amount of a cydoalka[b]pyridine-3-carbonylguanidine derivative or salt thereof as claimed in claim 1 as the active ingredient, together with a pharmaceutical acceptable carrier.

6. A method for treating cerebral ischemic disorders comprises administering to human in need of such treatment an effective amount of a cycloalka[b]pyridine-3-carbonylguanidine derivative or salt thereof as claimed in claim 1 as the active ingredient, together with a pharmaceutical acceptable carrier.

7. A method for treating diseases due to endothelial cell damage comprises administering to human in need of such prevention or treatment an effective amount of a cycloalka[b]pyridine-3-carbonylguanidine derivative or salt thereof as claimed in claim 1 as the active ingredient, together with a pharmaceutical acceptable carrier.

* * * * *